United States Patent
Capecchi et al.

(10) Patent No.: US 7,915,218 B2
(45) Date of Patent: Mar. 29, 2011

(54) POLYPEPTIDES FOR OLIGOMERIC ASSEMBLY OF ANTIGENS

(75) Inventors: Barbara Capecchi, Siena (IT); Vega Masignani, Siena (IT); Rino Rappuoli, Castelnuovo Berardenga (IT); Maria Scarselli, Siena (IT)

(73) Assignee: Novartis AG, Basel (CH)

( * ) Notice: Subject to any disclaimer, the term of this patent is extended or adjusted under 35 U.S.C. 154(b) by 574 days.

(21) Appl. No.: 11/632,385

(22) PCT Filed: Jul. 22, 2005

(86) PCT No.: PCT/IB2005/002528
§ 371 (c)(1),
(2), (4) Date: Feb. 1, 2008

(87) PCT Pub. No.: WO2006/011060
PCT Pub. Date: Feb. 2, 2006

(65) Prior Publication Data
US 2008/0260769 A1   Oct. 23, 2008

Related U.S. Application Data

(60) Provisional application No. 60/590,648, filed on Jul. 23, 2004.

(51) Int. Cl.
*C07K 14/00* (2006.01)
(52) U.S. Cl. .......................................... 514/2; 530/350
(58) Field of Classification Search ........................ None
See application file for complete search history.

(56) References Cited

U.S. PATENT DOCUMENTS
6,716,429 B1    4/2004   Sodroski et al.

FOREIGN PATENT DOCUMENTS
EP    1 365 027     11/2003
WO   WO 96/23881    8/1996

OTHER PUBLICATIONS

Roggenkamp et al. Jul. 2003; Molecular analysis of transport and oligomerization of the *Yersinia enterocolitica* adhesin YadA. J. Bacteriol. 185(13): 3735-3744.*
Comanducci, et al. 2002; NadA, a novel vaccine candidate of *Neisseria meningitides*. J. Exp. Med. 195(11): 1445-1454.*
Collins, P. "O Glycosylation of Glycoprotein G of Human Respiratory Syncytial Virus Is Specified within the Divergent Ectodomain," Journal of Virology, 64(8): 4007-4012 (1990).
Liu, S. et al. "Cell Surface Tumor Endothelium Market 8 Cytoplasmic Tail-independent Anthrax Toxin Binding . . . " The Journal of Biological Chemistry, 278(7): 5227-5234 (2003).
Capecchi, B. et al. "The Genome Revolution in Vaccine Research," Curr Issues Mol Biol, 6: 17-28 (2004).
Hoiczyk, E. et al. "Structure and sequence analysis of *Yersinia* YadA and *Moraxella* UspAs reveal a novel class of . . . " The EMBO Journal, vol. 19, No. 22, pp. 5989-5999 (2000).

* cited by examiner

*Primary Examiner* — Karen Cochrane Carlson
(74) *Attorney, Agent, or Firm* — Helen Lee; Otis Littlefield

(57) ABSTRACT

A system for expressing antigenic polypeptides in oligomeric form fuses the antigenic polypeptide to an oligomerisation polypeptide such that the oligomerisation polypeptide can interact with other oligomerisation polypeptides and bring multiple copies of the antigenic polypeptide into close proximity in the form of an oligomer. Expressing the polypeptides in oligomeric form in this way can improve their immunogenicity compared to a monomeric form.

23 Claims, 7 Drawing Sheets

*Figure 1*

SEQ ID NO:

E.coli/pET + CD4

E.coli/gp140-NadA + [CD4-gp140]

E.coli/gp140-NadA + CD4

Retention time (min)

SEQUENCE LISTING

<160> NUMBER OF SEQ ID NOS: 58

<210> SEQ ID NO 1
<211> LENGTH: 1255
<212> TYPE: PRT
<213> ORGANISM: SARS coronavirus

<400> SEQUENCE: 1

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365
```

```
Val Ser Ala Thr Lys Leu Asn Asp Leu Cys Phe Ser Asn Val Tyr Ala
    370                 375                 380

Asp Ser Phe Val Val Lys Gly Asp Val Arg Gln Ile Ala Pro Gly
385                 390                 395                 400

Gln Thr Gly Val Ile Ala Asp Tyr Asn Tyr Lys Leu Pro Asp Asp Phe
                    405                 410                 415

Met Gly Cys Val Leu Ala Trp Asn Thr Arg Asn Ile Asp Ala Thr Ser
                420                 425                 430

Thr Gly Asn Tyr Asn Tyr Lys Tyr Arg Tyr Leu Arg His Gly Lys Leu
            435                 440                 445

Arg Pro Phe Glu Arg Asp Ile Ser Asn Val Pro Phe Ser Pro Asp Gly
        450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                    485                 490                 495

Val Val Leu Ser Phe Glu Leu Leu Asn Ala Pro Ala Thr Val Cys Gly
                500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
        530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
                580                 585                 590

Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
        610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
        690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
        770                 775                 780

Ser Gln Ile Leu Pro Asp Pro Leu Lys Pro Thr Lys Arg Ser Phe Ile
```

```
                785                 790                 795                 800
        Glu Asp Leu Leu Phe Asn Lys Val Thr Leu Ala Asp Ala Gly Phe Met
                        805                 810                 815
        Lys Gln Tyr Gly Glu Cys Leu Gly Asp Ile Asn Ala Arg Asp Leu Ile
                        820                 825                 830
        Cys Ala Gln Lys Phe Asn Gly Leu Thr Val Leu Pro Pro Leu Leu Thr
                        835                 840                 845
        Asp Asp Met Ile Ala Ala Tyr Thr Ala Ala Leu Val Ser Gly Thr Ala
                        850                 855                 860
        Thr Ala Gly Trp Thr Phe Gly Ala Gly Ala Ala Leu Gln Ile Pro Phe
        865                 870                 875                 880
        Ala Met Gln Met Ala Tyr Arg Phe Asn Gly Ile Gly Val Thr Gln Asn
                        885                 890                 895
        Val Leu Tyr Glu Asn Gln Lys Gln Ile Ala Asn Gln Phe Asn Lys Ala
                        900                 905                 910
        Ile Ser Gln Ile Gln Glu Ser Leu Thr Thr Thr Ser Thr Ala Leu Gly
                        915                 920                 925
        Lys Leu Gln Asp Val Val Asn Gln Asn Ala Gln Ala Leu Asn Thr Leu
                        930                 935                 940
        Val Lys Gln Leu Ser Ser Asn Phe Gly Ala Ile Ser Ser Val Leu Asn
        945                 950                 955                 960
        Asp Ile Leu Ser Arg Leu Asp Lys Val Glu Ala Glu Val Gln Ile Asp
                        965                 970                 975
        Arg Leu Ile Thr Gly Arg Leu Gln Ser Leu Gln Thr Tyr Val Thr Gln
                        980                 985                 990
        Gln Leu Ile Arg Ala Ala Glu Ile Arg Ala Ser Ala Asn Leu Ala Ala
                        995                 1000                1005
        Thr Lys Met Ser Glu Cys Val Leu Gly Gln Ser Lys Arg Val Asp Phe
                        1010                1015                1020
        Cys Gly Lys Gly Tyr His Leu Met Ser Phe Pro Gln Ala Ala Pro His
        1025                1030                1035                1040
        Gly Val Val Phe Leu His Val Thr Tyr Val Pro Ser Gln Glu Arg Asn
                        1045                1050                1055
        Phe Thr Thr Ala Pro Ala Ile Cys His Glu Gly Lys Ala Tyr Phe Pro
                        1060                1065                1070
        Arg Glu Gly Val Phe Val Phe Asn Gly Thr Ser Trp Phe Ile Thr Gln
                        1075                1080                1085
        Arg Asn Phe Phe Ser Pro Gln Ile Ile Thr Thr Asp Asn Thr Phe Val
                        1090                1095                1100
        Ser Gly Asn Cys Asp Val Val Ile Gly Ile Ile Asn Asn Thr Val Tyr
        1105                1110                1115                1120
        Asp Pro Leu Gln Pro Glu Leu Asp Ser Phe Lys Glu Glu Leu Asp Lys
                        1125                1130                1135
        Tyr Phe Lys Asn His Thr Ser Pro Asp Val Asp Phe Gly Asp Ile Ser
                        1140                1145                1150
        Gly Ile Asn Ala Ser Val Val Asn Ile Gln Lys Glu Ile Asp Arg Leu
                        1155                1160                1165
        Asn Glu Val Ala Lys Asn Leu Asn Glu Ser Leu Ile Asp Leu Gln Glu
                        1170                1175                1180
        Leu Gly Lys Tyr Glu Gln Tyr Ile Lys Trp Pro Trp Tyr Val Trp Leu
        1185                1190                1195                1200
        Gly Phe Ile Ala Gly Leu Ile Ala Ile Val Met Val Thr Ile Leu Leu
                        1205                1210                1215
```

-continued

```
Cys Cys Met Thr Ser Cys Ser Cys Leu Lys Gly Ala Cys Ser Cys
            1220            1225            1230

Gly Ser Cys Cys Lys Phe Asp Glu Asp Asp Ser Glu Pro Val Leu Lys
        1235                1240                1245

Gly Val Lys Leu His Tyr Thr
    1250                1255

<210> SEQ ID NO 2
<211> LENGTH: 649
<212> TYPE: PRT
<213> ORGANISM: SARS coronavirus

<400> SEQUENCE: 2

Ser Asp Leu Asp Arg Cys Thr Thr Phe Asp Asp Val Gln Ala Pro Asn
1               5                   10                  15

Tyr Thr Gln His Thr Ser Ser Met Arg Gly Val Tyr Tyr Pro Asp Glu
            20                  25                  30

Ile Phe Arg Ser Asp Thr Leu Tyr Leu Thr Gln Asp Leu Phe Leu Pro
        35                  40                  45

Phe Tyr Ser Asn Val Thr Gly Phe His Thr Ile Asn His Thr Phe Gly
50                  55                  60

Asn Pro Val Ile Pro Phe Lys Asp Gly Ile Tyr Phe Ala Ala Thr Glu
65                  70                  75                  80

Lys Ser Asn Val Val Arg Gly Trp Val Phe Gly Ser Thr Met Asn Asn
                85                  90                  95

Lys Ser Gln Ser Val Ile Ile Ile Asn Asn Ser Thr Asn Val Val Ile
            100                 105                 110

Arg Ala Cys Asn Phe Glu Leu Cys Asp Asn Pro Phe Phe Ala Val Ser
        115                 120                 125

Lys Pro Met Gly Thr Gln Thr His Thr Met Ile Phe Asp Asn Ala Phe
    130                 135                 140

Asn Cys Thr Phe Glu Tyr Ile Ser Asp Ala Phe Ser Leu Asp Val Ser
145                 150                 155                 160

Glu Lys Ser Gly Asn Phe Lys His Leu Arg Glu Phe Val Phe Lys Asn
                165                 170                 175

Lys Asp Gly Phe Leu Tyr Val Tyr Lys Gly Tyr Gln Pro Ile Asp Val
            180                 185                 190

Val Arg Asp Leu Pro Ser Gly Phe Asn Thr Leu Lys Pro Ile Phe Lys
        195                 200                 205

Leu Pro Leu Gly Ile Asn Ile Thr Asn Phe Arg Ala Ile Leu Thr Ala
    210                 215                 220

Phe Ser Pro Ala Gln Asp Ile Trp Gly Thr Ser Ala Ala Ala Tyr Phe
225                 230                 235                 240

Val Gly Tyr Leu Lys Pro Thr Thr Phe Met Leu Lys Tyr Asp Glu Asn
                245                 250                 255

Gly Thr Ile Thr Asp Ala Val Asp Cys Ser Gln Asn Pro Leu Ala Glu
            260                 265                 270

Leu Lys Cys Ser Val Lys Ser Phe Glu Ile Asp Lys Gly Ile Tyr Gln
        275                 280                 285

Thr Ser Asn Phe Arg Val Val Pro Ser Gly Asp Val Val Arg Phe Pro
    290                 295                 300

Asn Ile Thr Asn Leu Cys Pro Phe Gly Glu Val Phe Asn Ala Thr Lys
305                 310                 315                 320

Phe Pro Ser Val Tyr Ala Trp Glu Arg Lys Lys Ile Ser Asn Cys Val
                325                 330                 335
```

```
Ala Asp Tyr Ser Val Leu Tyr Asn Ser Thr Phe Phe Ser Thr Phe Lys
            340                 345                 350

Cys Tyr Gly Val Ser Ala Thr Lys Leu Asn Asp Leu Cys Phe Ser Asn
            355                 360                 365

Val Tyr Ala Asp Ser Phe Val Lys Gly Asp Val Arg Gln Ile
            370                 375                 380

Ala Pro Gly Gln Thr Gly Val Ile Ala Asp Tyr Asn Tyr Lys Leu Pro
385                 390                 395                 400

Asp Asp Phe Met Gly Cys Val Leu Ala Trp Asn Thr Arg Asn Ile Asp
                405                 410                 415

Ala Thr Ser Thr Gly Asn Tyr Asn Tyr Lys Tyr Arg Tyr Leu Arg His
            420                 425                 430

Gly Lys Leu Arg Pro Phe Glu Arg Asp Ile Ser Asn Val Pro Phe Ser
            435                 440                 445

Pro Asp Gly Lys Pro Cys Thr Pro Pro Ala Leu Asn Cys Tyr Trp Pro
        450                 455                 460

Leu Asn Asp Tyr Gly Phe Tyr Thr Thr Thr Gly Ile Gly Tyr Gln Pro
465                 470                 475                 480

Tyr Arg Val Val Val Leu Ser Phe Glu Leu Leu Asn Ala Pro Ala Thr
                485                 490                 495

Val Cys Gly Pro Lys Leu Ser Thr Asp Leu Ile Lys Asn Gln Cys Val
            500                 505                 510

Asn Phe Asn Phe Asn Gly Leu Thr Gly Thr Gly Val Leu Thr Pro Ser
        515                 520                 525

Ser Lys Arg Phe Gln Pro Phe Gln Gln Phe Gly Arg Asp Val Ser Asp
    530                 535                 540

Phe Thr Asp Ser Val Arg Asp Pro Lys Thr Ser Glu Ile Leu Asp Ile
545                 550                 555                 560

Ser Pro Cys Ser Phe Gly Gly Val Ser Val Ile Thr Pro Gly Thr Asn
                565                 570                 575

Ala Ser Ser Glu Val Ala Val Leu Tyr Gln Asp Val Asn Cys Thr Asp
            580                 585                 590

Val Ser Thr Ala Ile His Ala Asp Gln Leu Thr Pro Ala Trp Arg Ile
        595                 600                 605

Tyr Ser Thr Gly Asn Asn Val Phe Gln Thr Gln Ala Gly Cys Leu Ile
    610                 615                 620

Gly Ala Glu His Val Asp Thr Ser Tyr Glu Cys Asp Ile Pro Ile Gly
625                 630                 635                 640

Ala Gly Ile Cys Ala Ser Tyr His Thr
                645

<210> SEQ ID NO 3
<211> LENGTH: 824
<212> TYPE: PRT
<213> ORGANISM: Artificial Sequence
<220> FEATURE:
<223> OTHER INFORMATION: NadA-gp120 hybrid

<400> SEQUENCE: 3

Met Lys His Phe Pro Ser Lys Val Leu Thr Thr Ala Ile Leu Ala Thr
1               5                   10                  15

Phe Cys Ser Gly Ala Le

-continued

```
              50                  55                  60
Glu Val His Asn Val Trp Ala Thr His Ala Cys Val Pro Thr Asp Pro
 65                  70                  75                  80

Asn Pro Gln Glu Ile Val Leu Glu Asn Val Thr Glu Asn Phe Asn Met
                 85                  90                  95

Trp Lys Asn Asn Met Val Glu Gln Met His Glu Asp Ile Ile Ser Leu
                100                 105                 110

Trp Asp Gln Ser Leu Lys Pro Cys Val Lys Leu Thr Pro Leu Cys Val
                115                 120                 125

Thr Leu His Cys Thr Asn Leu Lys Asn Ala Thr Asn Thr Lys Ser Ser
130                 135                 140

Asn Trp Lys Glu Met Asp Arg Gly Glu Ile Lys Asn Cys Ser Phe Lys
145                 150                 155                 160

Val Thr Thr Ser Ile Arg Asn Lys Met Gln Lys Glu Tyr Ala Leu Phe
                165                 170                 175

Tyr Lys Leu Asp Val Val Pro Ile Asp Asn Asp Asn Thr Ser Tyr Lys
                180                 185                 190

Leu Ile Asn Cys Asn Thr Ser Val Ile Thr Gln Ala Cys Pro Lys Val
                195                 200                 205

Ser Phe Glu Pro Ile Pro Ile His Tyr Cys Ala Pro Ala Gly Phe Ala
210                 215                 220

Ile Leu Lys Cys Asn Asp Lys Lys Phe Asn Gly Ser Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Gly Val Val Ile
                260                 265                 270

Arg Ser Glu Asn Phe Thr Asp Asn Ala Lys Thr Ile Ile Val Gln Leu
                275                 280                 285

Lys Glu Ser Val Glu Ile Asn Cys Thr Arg Pro Asn Asn Asn Thr Arg
                290                 295                 300

Lys Ser Ile Thr Ile Gly Pro Gly Arg Ala Phe Tyr Ala Thr Gly Asp
305                 310                 315                 320

Ile Ile Gly Asp Ile Arg Gln Ala His Cys Asn Ile Ser Gly Glu Lys
                325                 330                 335

Trp Asn Asn Thr Leu Lys Gln Ile Val Thr Lys Leu Gln Ala Gln Phe
                340                 345                 350

Gly Asn Lys Thr Ile Val Phe Lys Gln Ser Ser Gly Gly Asp Pro Glu
                355                 360                 365

Ile Val Met His Ser Phe Asn Cys Gly Gly Glu Phe Phe Tyr Cys Asn
370                 375                 380

Ser Thr Gln Leu Phe Asn Ser Thr Trp Asn Asn Thr Ile Gly Pro Asn
385                 390                 395                 400

Asn Thr Asn Gly Thr Ile Thr Leu Pro Cys Arg Ile Lys Gln Ile Ile
                405                 410                 415

Asn Arg Trp Gln Glu Val Gly Lys Ala Met Tyr Ala Pro Pro Ile Arg
                420                 425                 430

Gly Gln Ile Arg Cys Ser Ser Asn Ile Thr Gly Leu Leu Leu Thr Arg
                435                 440                 445

Asp Gly Gly Lys Glu Ile Ser Asn Thr Thr Glu Ile Phe Arg Pro Gly
                450                 455                 460

Gly Gly Asp Met Arg Asp Asn Trp Arg Ser Glu Leu Tyr Lys Tyr Lys
465                 470                 475                 480
```

```
Val Val Lys Ile Glu Pro Leu Gly Val Ala Pro Thr Lys Ala Lys Arg
            485                 490                 495

Arg Val Val Gln Arg Glu Lys Arg Gly Ser Lys Val Val Thr Asn Leu
        500                 505                 510

Thr Lys Thr Val Asn Glu Asn Lys Gln Asn Val Asp Ala Lys Val Lys
    515                 520                 525

Ala Ala Glu Ser Glu Ile Glu Lys Leu Thr Thr Lys Leu Ala Asp Thr
530                 535                 540

Asp Ala Ala Leu Ala Asp Thr Asp Ala Ala Leu Asp Ala Thr Thr Asn
545                 550                 555                 560

Ala Leu Asn Lys Leu Gly Glu Asn Ile Thr Thr Phe Ala Glu Glu Thr
            565                 570                 575

Lys Thr Asn Ile Val Lys Ile Asp Glu Lys Leu Glu Ala Val Ala Asp
        580                 585                 590

Thr Val Asp Lys His Ala Glu Ala Phe Asn Asp Ile Ala Asp Ser Leu
    595                 600                 605

Asp Glu Thr Asn Thr Lys Ala Asp Glu Ala Val Lys Thr Ala Asn Glu
610                 615                 620

Ala Lys Gln Thr Ala Glu Glu Thr Lys Gln Asn Val Asp Ala Lys Val
625                 630                 635                 640

Lys Ala Ala Glu Thr Ala Ala Gly Lys Ala Glu Ala Ala Gly Thr
            645                 650                 655

Ala Asn Thr Ala Ala Asp Lys Ala Glu Ala Val Ala Lys Val Thr
        660                 665                 670

Asp Ile Lys Ala Asp Ile Ala Thr Asn Lys Asp Asn Ile Ala Lys Lys
    675                 680                 685

Ala Asn Ser Ala Asp Val Tyr Thr Arg Glu Glu Ser Asp Ser Lys Phe
690                 695                 700

Val Arg Ile Asp Gly Leu Asn Ala Thr Thr Glu Lys Leu Asp Thr Arg
705                 710                 715                 720

Leu Ala Ser Ala Glu Lys Ser Ile Ala Asp His Asp Thr Arg Leu Asn
            725                 730                 735

Gly Leu Asp Lys Thr Val Ser Asp Leu Arg Lys Glu Thr Arg Gln Gly
        740                 745                 750

Leu Ala Glu Gln Ala Ala Leu Ser Gly Leu Phe Gln Pro Tyr Asn Val
    755                 760                 765

Gly Arg Phe Asn Val Thr Ala Ala Val Gly Gly Tyr Lys Ser Glu Ser
770                 775                 780

Ala Val Ala Ile Gly Thr Gly Phe Arg Phe Thr Glu Asn Phe Ala Ala
785                 790                 795                 800

Lys Ala Gly Val Ala Val Gly Thr Ser Ser Gly Ser Ser Ala Ala Tyr
            805                 810                 815

His Val Gly Val Asn Tyr Glu Trp
            820

<210> SEQ ID NO 4
<211> LENGTH: 769
<212> TYPE: PRT
<213> ORGANISM: Artificial Sequence
<220> FEATURE:
<223> OTHER INFORMATION: NadA-gp120 hybrid

<400> SEQUENCE: 4

Met Lys His Phe Pro Ser Lys Val Leu Thr Thr Ala Ile Leu Ala Thr
1               5                   10                  15

Phe Cys Ser Gly Ala Leu Ala Ala Ser Asn Asp Asp Asp Ser Ala Val
```

```
                    20                  25                  30
Glu Lys Leu Trp Val Thr Val Tyr Tyr Gly Val Pro Val Trp Lys Glu
                35                  40                  45

Ala Thr Thr Thr Leu Phe Cys Ala Ser Asp Ala Lys Ala Tyr Asp Thr
 50                  55                  60

Glu Val His Asn Val Trp Ala Thr His Ala Cys Val Pro Thr Asp Pro
 65                  70                  75                  80

Asn Pro Gln Glu Ile Val Leu Glu Asn Val Thr Glu Asn Phe Asn Met
                85                  90                  95

Trp Lys Asn Asn Met Val Glu Gln Met His Glu Asp Ile Ile Ser Leu
                100                 105                 110

Trp Asp Gln Ser Leu Lys Pro Cys Val Lys Leu Thr Pro Leu Cys Val
                115                 120                 125

Thr Leu His Cys Thr Asn Leu Lys Asn Ala Thr Asn Thr Lys Ser Ser
    130                 135                 140

Asn Trp Lys Glu Met Asp Arg Gly Glu Ile Lys Asn Cys Ser Phe Lys
145                 150                 155                 160

Val Thr Thr Ser Ile Arg Asn Lys Met Gln Lys Glu Tyr Ala Leu Phe
                165                 170                 175

Tyr Lys Leu Asp Val Val Pro Ile Asp Asn Asp Asn Thr Ser Tyr Lys
                180                 185                 190

Leu Ile Asn Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
        210                 215                 220

Ile Leu Lys Cys Asn Asp Lys Lys Phe Asn Gly Ser Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Gly Val Val Ile
            260                 265                 270

Arg Ser Glu Asn Phe Thr Asp Asn Ala Lys Thr Ile Ile Val Gln Leu
        275                 280                 285

Lys Glu Ser Val Glu Ile Asn Cys Thr Arg Pro Asn Asn Asn Thr Arg
    290                 295                 300

Lys Ser Ile Thr Ile Gly Pro Gly Arg Ala Phe Tyr Ala Thr Gly Asp
305                 310                 315                 320

Ile Ile Gly Asp Ile Arg Gln Ala His Cys Asn Ile Ser Gly Glu Lys
                325                 330                 335

Trp Asn Asn Thr Leu Lys Gln Ile Val Thr Lys Leu Gln Ala Gln Phe
                340                 345                 350

Gly Asn Lys Thr Ile Val Phe Lys Gln Ser Ser Gly Gly Asp Pro Glu
            355                 360                 365

Ile Val Met His Ser Phe Asn Cys Gly Gly Glu Phe Phe Tyr Cys Asn
        370                 375                 380

Ser Thr Gln Leu Phe Asn Ser Thr Trp Asn Asn Thr Ile Gly Pro Asn
385                 390                 395                 400

Asn Thr Asn Gly Thr Ile Thr Leu Pro Cys Arg Ile Lys Gln Ile Ile
                405                 410                 415

Asn Arg Trp Gln Glu Val Gly Lys Ala Met Tyr Ala Pro Pro Ile Arg
                420                 425                 430

Gly Gln Ile Arg Cys Ser Ser Asn Ile Thr Gly Leu Leu Leu Thr Arg
            435                 440                 445
```

-continued

```
Asp Gly Gly Lys Glu Ile Ser Asn Thr Thr Glu Ile Phe Arg Pro Gly
    450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Lys Ala Lys Arg
                485                 490                 495

Arg Val Val Gln Arg Glu Lys Arg Gly Ser Lys Val Val Thr Asn Leu
                500                 505                 510

Thr Lys Thr Val Asn Glu Asn Lys Gln Asn Val Asp Ala Lys Val Lys
        515                 520                 525

Ala Ala Glu Ser Glu Ile Glu Lys Leu Thr Thr Lys Leu Ala Asp Thr
    530                 535                 540

Asp Ala Ala Leu Ala Asp Thr Asp Ala Ala Leu Asp Ala Thr Thr Asn
545                 550                 555                 560

Ala Leu Asn Lys Leu Gly Glu Asn Ile Thr Thr Phe Ala Glu Glu Thr
                565                 570                 575

Lys Thr Asn Ile Val Lys Ile Asp Glu Lys Leu Glu Ala Val Ala Asp
                580                 585                 590

Thr Val Asp Lys His Ala Glu Ala Phe Asn Asp Ile Ala Asp Ser Leu
        595                 600                 605

Asp Glu Thr Asn Thr Lys Ala Asp Glu Ala Val Lys Thr Ala Asn Glu
    610                 615                 620

Ala Lys Gln Thr Ala Glu Glu Thr Lys Gln Asn Val Asp Ala Lys Val
625                 630                 635                 640

Lys Ala Ala Glu Thr Ala Ala Gly Lys Ala Glu Ala Ala Ala Gly Thr
                645                 650                 655

Ala Asn Thr Ala Ala Asp Lys Ala Glu Ala Val Ala Ala Lys Val Thr
                660                 665                 670

Asp Ile Lys Ala Asp Ile Ala Thr Asn Lys Asp Asn Ile Ala Lys Lys
        675                 680                 685

Ala Asn Ser Ala Asp Val Tyr Thr Arg Glu Glu Ser Asp Ser Lys Phe
    690                 695                 700

Val Arg Ile Asp Gly Leu Asn Ala Thr Thr Glu Lys Leu Asp Thr Arg
705                 710                 715                 720

Leu Ala Ser Ala Glu Lys Ser Ile Ala Asp His Asp Thr Arg Leu Asn
                725                 730                 735

Gly Leu Asp Lys Thr Val Ser Asp Leu Arg Lys Glu Thr Arg Gln Gly
                740                 745                 750

Leu Ala Glu Gln Ala Ala Leu Ser Gly Leu Phe Gln Pro Tyr Asn Val
        755                 760                 765

Gly
```

<210> SEQ ID NO 5
<211> LENGTH: 797
<212> TYPE: PRT
<213> ORGANISM: Artificial Sequence
<220> FEATURE:
<223> OTHER INFORMATION: NadA-gp120 hybrid

<400> SEQUENCE: 5

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Asp Ser Ala Val
                20                  25                  30

Glu Lys Leu Trp Val Thr Val Tyr Tyr Gly Val Pro Val Trp Lys Glu
            35                  40                  45
```

```
Ala Thr Thr Thr Leu Phe Cys Ala Ser Asp Ala Lys Ala Tyr Asp Thr
     50                  55                  60
Glu Val His Asn Val Trp Ala Thr His Ala Cys Val Pro Thr Asp Pro
65                   70                  75                  80
Asn Pro Gln Glu Ile Val Leu Glu Asn Val Thr Glu Asn Phe Asn Met
                 85                  90                  95
Trp Lys Asn Asn Met Val Glu Gln Met His Glu Asp Ile Ile Ser Leu
                100                 105                 110
Trp Asp Gln Ser Leu Lys Pro Cys Val Lys Leu Thr Pro Leu Cys Val
            115                 120                 125
Thr Leu His Cys Thr Asn Leu Lys Asn Ala Thr Asn Thr Lys Ser Ser
    130                 135                 140
Asn Trp Lys Glu Met Asp Arg Gly Glu Ile Lys Asn Cys Ser Phe Lys
145                 150                 155                 160
Val Gly Ala Gly Lys Leu Ile Asn Cys Asn Thr Ser Val Ile Thr Gln
                165                 170                 175
Ala Cys Pro Lys Val Ser Phe Glu Pro Ile Pro Ile His Tyr Cys Ala
            180                 185                 190
Pro Ala Gly Phe Ala Ile Leu Lys Cys Asn Asp Lys Lys Phe Asn Gly
        195                 200                 205
Ser Gly Pro Cys Thr Asn Val Ser Thr Val Gln Cys Thr His Gly Ile
210                 215                 220
Arg Pro Val Val Ser Thr Gln Leu Leu Leu Asn Gly Ser Leu Ala Glu
225                 230                 235                 240
Glu Gly Val Val Ile Arg Ser Glu Asn Phe Thr Asp Asn Ala Lys Thr
                245                 250                 255
Ile Ile Val Gln Leu Lys Glu Ser Val Glu Ile Asn Cys Thr Arg Pro
            260                 265                 270
Asn Asn Asn Thr Arg Lys Ser Ile Thr Ile Gly Pro Gly Arg Ala Phe
        275                 280                 285
Tyr Ala Thr Gly Asp Ile Ile Gly Asp Ile Arg Gln Ala His Cys Asn
290                 295                 300
Ile Ser Gly Glu Lys Trp Asn Asn Thr Leu Lys Gln Ile Val Thr Lys
305                 310                 315                 320
Leu Gln Ala Gln Phe Gly Asn Lys Thr Ile Val Phe Lys Gln Ser Ser
                325                 330                 335
Gly Gly Asp Pro Glu Ile Val Met His Ser Phe Asn Cys Gly Gly Glu
            340                 345                 350
Phe Phe Tyr Cys Asn Ser Thr Gln Leu Phe Asn Ser Thr Trp Asn Asn
        355                 360                 365
Thr Ile Gly Pro Asn Asn Thr Asn Gly Thr Ile Thr Leu Pro Cys Arg
    370                 375                 380
Ile Lys Gln Ile Ile Asn Arg Trp Gln Glu Val Gly Lys Ala Met Tyr
385                 390                 395                 400
Ala Pro Pro Ile Arg Gly Gln Ile Arg Cys Ser Ser Asn Ile Thr Gly
                405                 410                 415
Leu Leu Leu Thr Arg Asp Gly Gly Lys Glu Ile Ser Asn Thr Thr Glu
            420                 425                 430
Ile Phe Arg Pro Gly Gly Asp Met Arg Asp Asn Trp Arg Ser Glu
        435                 440                 445
Leu Tyr Lys Tyr Lys Val Val Lys Ile Glu Pro Leu Gly Val Ala Pro
    450                 455                 460
Thr Lys Ala Ile Ser Ser Val Val Gln Ser Glu Lys Ser Gly Ser Lys
```

```
                465                 470                 475                 480
Val Val Thr Asn Leu Thr Lys Thr Val Asn Glu Asn Lys Gln Asn Val
                    485                 490                 495

Asp Ala Lys Val Lys Ala Ala Glu Ser Glu Ile Glu Lys Leu Thr Thr
                500                 505                 510

Lys Leu Ala Asp Thr Asp Ala Ala Leu Ala Asp Thr Asp Ala Ala Leu
                515                 520                 525

Asp Ala Thr Thr Asn Ala Leu Asn Lys Leu Gly Glu Asn Ile Thr Thr
            530                 535                 540

Phe Ala Glu Glu Thr Lys Thr Asn Ile Val Lys Ile Asp Glu Lys Leu
545                 550                 555                 560

Glu Ala Val Ala Asp Thr Val Asp Lys His Ala Glu Ala Phe Asn Asp
                    565                 570                 575

Ile Ala Asp Ser Leu Asp Glu Thr Asn Thr Lys Ala Asp Glu Ala Val
                580                 585                 590

Lys Thr Ala Asn Glu Ala Lys Gln Thr Ala Glu Thr Lys Gln Asn
                595                 600                 605

Val Asp Ala Lys Val Lys Ala Ala Glu Thr Ala Ala Gly Lys Ala Glu
            610                 615                 620

Ala Ala Ala Gly Thr Ala Asn Thr Ala Ala Asp Lys Ala Glu Ala Val
625                 630                 635                 640

Ala Ala Lys Val Thr Asp Ile Lys Ala Asp Ile Ala Thr Asn Lys Asp
                    645                 650                 655

Asn Ile Ala Lys Lys Ala Asn Ser Ala Asp Val Tyr Thr Arg Glu Glu
                660                 665                 670

Ser Asp Ser Lys Phe Val Arg Ile Asp Gly Leu Asn Ala Thr Thr Glu
            675                 680                 685

Lys Leu Asp Thr Arg Leu Ala Ser Ala Glu Lys Ser Ile Ala Asp His
690                 695                 700

Asp Thr Arg Leu Asn Gly Leu Asp Lys Thr Val Ser Asp Leu Arg Lys
705                 710                 715                 720

Glu Thr Arg Gln Gly Leu Ala Glu Gln Ala Ala Leu Ser Gly Leu Phe
                    725                 730                 735

Gln Pro Tyr Asn Val Gly Arg Phe Asn Val Thr Ala Ala Val Gly Gly
                740                 745                 750

Tyr Lys Ser Glu Ser Ala Val Ala Ile Gly Thr Gly Phe Arg Phe Thr
            755                 760                 765

Glu Asn Phe Ala Ala Lys Ala Gly Val Ala Val Gly Thr Ser Ser Gly
770                 775                 780

Ser Ser Ala Ala Tyr His Val Gly Val Asn Tyr Glu Trp
785                 790                 795

<210> SEQ ID NO 6
<211> LENGTH: 742
<212> TYPE: PRT
<213> ORGANISM: Artificial Sequence
<220> FEATURE:
<223> OTHER INFORMATION: NadA-gp120 hybrid

<400> SEQUENCE: 6

Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Asp Ser Ala Val
                20                  25                  30

Glu Lys Leu Trp Val Thr Val Tyr Tyr Gly Val Pro Val Trp Lys Glu
            35                  40                  45
```

-continued

Ala Thr Thr Thr Leu Phe Cys Ala Ser Asp Ala Lys Ala Tyr Asp Thr
        50                  55                  60

Glu Val His Asn Val Trp Ala Thr His Ala Cys Val Pro Thr Asp Pro
65                  70                  75                  80

Asn Pro Gln Glu Ile Val Leu Glu Asn Val Thr Glu Asn Phe Asn Met
                85                  90                  95

Trp Lys Asn Asn Met Val Glu Gln Met His Glu Asp Ile Ile Ser Leu
            100                 105                 110

Trp Asp Gln Ser Leu Lys Pro Cys Val Lys Leu Thr Pro Leu Cys Val
            115                 120                 125

Thr Leu His Cys Thr Asn Leu Lys Asn Ala Thr Asn Thr Lys Ser Ser
        130                 135                 140

Asn Trp Lys Glu Met Asp Arg Gly Glu Ile Lys Asn Cys Ser Phe Lys
145                 150                 155                 160

Val Gly Ala Gly Lys Leu Ile Asn Cys Asn Thr Ser Val Ile Thr Gln
                165                 170                 175

Ala Cys Pro Lys Val Ser Phe Glu Pro Ile Pro Ile His Tyr Cys Ala
            180                 185                 190

Pro Ala Gly Phe Ala Ile Leu Lys Cys Asn Asp Lys Lys Phe Asn Gly
        195                 200                 205

Ser Gly Pro Cys Thr Asn Val Ser Thr Val Gln Cys Thr His Gly Ile
210                 215                 220

Arg Pro Val Val Ser Thr Gln Leu Leu Leu Asn Gly Ser Leu Ala Glu
225                 230                 235                 240

Glu Gly Val Val Ile Arg Ser Glu Asn Phe Thr Asp Asn Ala Lys Thr
                245                 250                 255

Ile Ile Val Gln Leu Lys Glu Ser Val Glu Ile Asn Cys Thr Arg Pro
            260                 265                 270

Asn Asn Asn Thr Arg Lys Ser Ile Thr Ile Gly Pro Gly Arg Ala Phe
        275                 280                 285

Tyr Ala Thr Gly Asp Ile Ile Gly Asp Ile Arg Gln Ala His Cys Asn
290                 295                 300

Ile Ser Gly Glu Lys Trp Asn Asn Thr Leu Lys Gln Ile Val Thr Lys
305                 310                 315                 320

Leu Gln Ala Gln Phe Gly Asn Lys Thr Ile Val Phe Lys Gln Ser Ser
            325                 330                 335

Gly Gly Asp Pro Glu Ile Val Met His Ser Phe Asn Cys Gly Gly Glu
        340                 345                 350

Phe Phe Tyr Cys Asn Ser Thr Gln Leu Phe Asn Ser Thr Trp Asn Asn
        355                 360                 365

Thr Ile Gly Pro Asn Asn Thr Asn Gly Thr Ile Thr Leu Pro Cys Arg
        370                 375                 380

Ile Lys Gln Ile Ile Asn Arg Trp Gln Glu Val Gly Lys Ala Met Tyr
385                 390                 395                 400

Ala Pro Pro Ile Arg Gly Gln Ile Arg Cys Ser Ser Asn Ile Thr Gly
            405                 410                 415

Leu Leu Leu Thr Arg Asp Gly Gly Lys Glu Ile Ser Asn Thr Thr Glu
        420                 425                 430

Ile Phe Arg Pro Gly Gly Asp Met Arg Asp Asn Trp Arg Ser Glu
        435                 440                 445

Leu Tyr Lys Tyr Lys Val Val Lys Ile Glu Pro Leu Gly Val Ala Pro
450                 455                 460

Thr Lys Ala Ile Ser Ser Val Val Gln Ser Glu Lys Ser Gly Ser Lys

```
                465                 470                 475                 480
Val Val Thr Asn Leu Thr Lys Thr Val Asn Glu Asn Lys Gln Asn Val
                    485                 490                 495

Asp Ala Lys Val Lys Ala Ala Glu Ser Glu Ile Glu Lys Leu Thr Thr
                500                 505                 510

Lys Leu Ala Asp Thr Asp Ala Ala Leu Ala Asp Thr Asp Ala Ala Leu
                515                 520                 525

Asp Ala Thr Thr Asn Ala Leu Asn Lys Leu Gly Glu Asn Ile Thr Thr
            530                 535                 540

Phe Ala Glu Glu Thr Lys Thr Asn Ile Val Lys Ile Asp Glu Lys Leu
545                 550                 555                 560

Glu Ala Val Ala Asp Thr Val Asp Lys His Ala Glu Ala Phe Asn Asp
                565                 570                 575

Ile Ala Asp Ser Leu Asp Glu Thr Asn Thr Lys Ala Asp Glu Ala Val
                580                 585                 590

Lys Thr Ala Asn Glu Ala Lys Gln Thr Ala Glu Thr Lys Gln Asn
            595                 600                 605

Val Asp Ala Lys Val Lys Ala Ala Glu Thr Ala Ala Gly Lys Ala Glu
        610                 615                 620

Ala Ala Ala Gly Thr Ala Asn Thr Ala Ala Asp Lys Ala Glu Ala Val
625                 630                 635                 640

Ala Ala Lys Val Thr Asp Ile Lys Ala Asp Ile Ala Thr Asn Lys Asp
                    645                 650                 655

Asn Ile Ala Lys Lys Ala Asn Ser Ala Asp Val Tyr Thr Arg Glu Glu
                660                 665                 670

Ser Asp Ser Lys Phe Val Arg Ile Asp Gly Leu Asn Ala Thr Thr Glu
            675                 680                 685

Lys Leu Asp Thr Arg Leu Ala Ser Ala Glu Lys Ser Ile Ala Asp His
        690                 695                 700

Asp Thr Arg Leu Asn Gly Leu Asp Lys Thr Val Ser Asp Leu Arg Lys
705                 710                 715                 720

Glu Thr Arg Gln Gly Leu Ala Glu Gln Ala Ala Leu Ser Gly Leu Phe
                725                 730                 735

Gln Pro Tyr Asn Val Gly
            740

<210> SEQ ID NO 7
<211> LENGTH: 705
<212> TYPE: PRT
<213> ORGANISM: Artificial Sequence
<220> FEATURE:
<223> OTHER INFORMATION: NadA-gp120 hybrid

<400> SEQUENCE: 7

Met Lys His Phe Pro Ser Lys Val Leu Thr Thr Ala Ile Leu Ala Thr
1               5                   10                  15

Phe Cys Ser Gly Ala Leu Ala Ala Ser Asn Asp Asp Asp Ser Ala Val
                20                  25                  30

Glu Lys Leu Trp Val Thr Val Tyr Tyr Gly Val Pro Val Trp Lys Glu
            35                  40                  45

Ala Thr Thr Thr Leu Phe Cys Ala Ser Asp Ala Lys Ala Tyr Asp Thr
        50                  55                  60

Glu Val

-continued

```
Trp Lys Asn Asn Met Val Glu Gln Met His Glu Asp Ile Ile Ser Leu
            100                 105                 110
Trp Asp Gln Ser Leu Lys Pro Cys Val Lys Leu Thr Pro Leu Cys Val
        115                 120                 125
Thr Leu His Cys Thr Asn Leu Lys Asn Ala Thr Asn Thr Lys Ser Ser
130                 135                 140
Asn Trp Lys Glu Met Asp Arg Gly Glu Ile Lys Asn Cys Ser Phe Lys
145                 150                 155                 160
Val Gly Ala Gly Lys Leu Ile Asn Cys Asn Thr Ser Val Ile Thr Gln
                165                 170                 175
Ala Cys Pro Lys Val Ser Phe Glu Pro Ile Pro Ile His Tyr Cys Ala
            180                 185                 190
Pro Ala Gly Phe Ala Ile Leu Lys Cys Asn Asp Lys Lys Phe Asn Gly
        195                 200                 205
Ser Gly Pro Cys Thr Asn Val Ser Thr Val Gln Cys Thr His Gly Ile
210                 215                 220
Arg Pro Val Val Ser Thr Gln Leu Leu Leu Asn Gly Ser Leu Ala Glu
225                 230                 235                 240
Glu Gly Val Val Ile Arg Ser Glu Asn Phe Thr Asp Asn Ala Lys Thr
                245                 250                 255
Ile Ile Val Gln Leu Lys Glu Ser Val Glu Ile Asn Cys Thr Arg Pro
            260                 265                 270
Asn Asn Asn Thr Arg Lys Ser Ile Thr Ile Gly Pro Gly Arg Ala Phe
        275                 280                 285
Tyr Ala Thr Gly Asp Ile Ile Gly Asp Ile Arg Gln Ala His Cys Asn
290                 295                 300
Ile Ser Gly Glu Lys Trp Asn Asn Thr Leu Lys Gln Ile Val Thr Lys
305                 310                 315                 320
Leu Gln Ala Gln Phe Gly Asn Lys Thr Ile Val Phe Lys Gln Ser Ser
                325                 330                 335
Gly Gly Asp Pro Glu Ile Val Met His Ser Phe Asn Cys Gly Gly Glu
            340                 345                 350
Phe Phe Tyr Cys Asn Ser Thr Gln Leu Phe Asn Ser Thr Trp Asn Asn
        355                 360                 365
Thr Ile Gly Pro Asn Asn Thr Asn Gly Thr Ile Thr Leu Pro Cys Arg
370                 375                 380
Ile Lys Gln Ile Ile Asn Arg Trp Gln Glu Val Gly Lys Ala Met Tyr
385                 390                 395                 400
Ala Pro Pro Ile Arg Gly Gln Ile Arg Cys Ser Ser Asn Ile Thr Gly
                405                 410                 415
Leu Leu Leu Thr Arg Asp Gly Gly Lys Glu Ile Ser Asn Thr Thr Glu
            420                 425                 430
Ile Phe Arg Pro Gly Gly Gly Asp Met Arg Asp Asn Trp Arg Ser Glu
        435                 440                 445
Leu Tyr Lys Tyr Lys Val Val Lys Ile Glu Pro Leu Gly Val Ala Pro
450                 455                 460
Thr Lys Ala Ile Ser Ser Val Val Gln Ser Glu Lys Ser Ala Val Thr
465                 470                 475                 480
Leu Gly Ala Met Phe Leu Gly Phe Leu Gly Ala Ala Gly Ser Thr Met
                485                 490                 495
Gly Ala Arg Ser Leu Thr Leu Thr Val Gln Ala Arg Gln Leu Leu Ser
            500                 505                 510
Gly Ile Val Gln Gln Gln Asn Asn Leu Leu Arg Ala Ile Glu Ala Gln
```

-continued

```
                    515                 520                 525
Gln His Leu Leu Gln Leu Thr Val Trp Gly Ile Lys Gln Leu Gln Ala
        530                 535                 540
Arg Val Leu Ala Val Glu Arg Tyr Leu Lys Asp Gln Gln Leu Leu Gly
545                 550                 555                 560
Ile Trp Gly Cys Ser Gly Lys Leu Ile Cys Thr Thr Ala Val Pro Trp
                565                 570                 575
Asn Ala Ser Trp Ser Asn Lys Ser Leu Asp Gln Ile Trp Asn Asn Met
            580                 585                 590
Thr Trp Met Glu Trp Glu Arg Glu Ile Asp Asn Tyr Thr Asn Leu Ile
        595                 600                 605
Tyr Thr Leu Ile Glu Glu Ser Gln Asn Gln Gln Glu Lys Asn Glu Gln
    610                 615                 620
Glu Leu Leu Glu Leu Asp Lys Trp Ala Ser Leu Trp Asn Trp Phe Asp
625                 630                 635                 640
Ile Ser Lys Trp Leu Trp Tyr Ile Lys Leu Arg Phe Asn Val Thr Ala
                645                 650                 655
Ala Val Gly Gly Tyr Lys Ser Glu Ser Ala Val Ala Ile Gly Thr Gly
            660                 665                 670
Phe Arg Phe Thr Glu Asn Phe Ala Ala Lys Ala Gly Val Ala Val Gly
        675                 680                 685
Thr Ser Ser Gly Ser Ser Ala Ala Tyr His Val Gly Val Asn Tyr Glu
    690                 695                 700
Trp
705

<210> SEQ ID NO 8
<211> LENGTH: 724
<212> TYPE: PRT
<213> ORGANISM: Artificial Sequence
<220> FEATURE:
<223> OTHER INFORMATION: NadA-gp120 hybrid

<400> SEQUENCE: 8

Met Lys His Phe Pro Ser Lys Val Leu Thr Thr Ala Ile Leu Ala Thr
1               5                   10                  15
Phe Cys Ser Gly Ala Leu Ala Ala Ser Asn Asp Asp Ser Ala Val
            20                  25                  30
Glu Lys Leu Trp Val Thr Val Tyr Tyr Gly Val Pro Val Trp Lys Glu
        35                  40                  45
Ala Thr Thr Thr Leu Phe Cys Ala Ser Asp Ala Lys Ala Tyr Asp Thr
    50                  55                  60
Glu Val His Asn Val Trp Ala Thr His Ala Cys Val Pro Thr Asp Pro
65                  70                  75                  80
Asn Pro Gln Glu Ile Val Leu Glu Asn Val

```
Ala Cys Pro Lys Val Ser Phe Glu Pro Ile Pro Ile His Tyr Cys Ala
            180                 185                 190

Pro Ala Gly Phe Ala Ile Leu Lys Cys Asn Asp Lys Lys Phe Asn Gly
            195                 200                 205

Ser Gly Pro Cys Thr Asn Val Ser Thr Val Gln Cys Thr His Gly Ile
            210                 215                 220

Arg Pro Val Val Ser Thr Gln Leu Leu Leu Asn Gly Ser Leu Ala Glu
225                 230                 235                 240

Glu Gly Val Val Ile Arg Ser Glu Asn Phe Thr Asp Asn Ala Lys Thr
                245                 250                 255

Ile Ile Val Gln Leu Lys Glu Ser Val Glu Ile Asn Cys Thr Arg Pro
                260                 265                 270

Asn Asn Asn Thr Arg Lys Ser Ile Thr Ile Gly Pro Gly Arg Ala Phe
            275                 280                 285

Tyr Ala Thr Gly Asp Ile Ile Gly Asp Ile Arg Gln Ala His Cys Asn
            290                 295                 300

Ile Ser Gly Glu Lys Trp Asn Asn Thr Leu Lys Gln Ile Val Thr Lys
305                 310                 315                 320

Leu Gln Ala Gln Phe Gly Asn Lys Thr Ile Val Phe Lys Gln Ser Ser
                325                 330                 335

Gly Gly Asp Pro Glu Ile Val Met His Ser Phe Asn Cys Gly Gly Glu
            340                 345                 350

Phe Phe Tyr Cys Asn Ser Thr Gln Leu Phe Asn Ser Thr Trp Asn Asn
            355                 360                 365

Thr Ile Gly Pro Asn Asn Thr Asn Gly Thr Ile Thr Leu Pro Cys Arg
            370                 375                 380

Ile Lys Gln Ile Ile Asn Arg Trp Gln Glu Val Gly Lys Ala Met Tyr
385                 390                 395                 400

Ala Pro Pro Ile Arg Gly Gln Ile Arg Cys Ser Ser Asn Ile Thr Gly
                405                 410                 415

Leu Leu Leu Thr Arg Asp Gly Gly Lys Glu Ile Ser Asn Thr Thr Glu
            420                 425                 430

Ile Phe Arg Pro Gly Gly Gly Asp Met Arg Asp Asn Trp Arg Ser Glu
            435                 440                 445

Leu Tyr Lys Tyr Lys Val Val Lys Ile Glu Pro Leu Gly Val Ala Pro
            450                 455                 460

Thr Lys Ala Ile Ser Ser Val Val Gln Ser Glu Lys Ser Ala Val Thr
465                 470                 475                 480

Leu Gly Ala Met Phe Leu Gly Phe Leu Gly Ala Ala Gly Ser Thr Met
                485                 490                 495

Gly Ala Arg Ser Leu Thr Leu Thr Val Gln Ala Arg Gln Leu Leu Ser
            500                 505                 510

Gly Ile Val Gln Gln Gln Asn Asn Leu Leu Arg Ala Ile Glu Ala Gln
            515                 520                 525

Gln His Leu Leu Gln Leu Thr Val Trp Gly Ile Lys Gln Leu Gln Ala
            530                 535                 540

Arg Val Leu Ala Val Glu Arg Tyr Leu Lys Asp Gln Gln Leu Leu Gly
545                 550                 555                 560

Ile Trp Gly Cys Ser Gly Lys Leu Ile Cys Thr Thr Ala Val Pro Trp
                565                 570                 575

Asn Ala Ser Trp Ser Asn Lys Ser Leu Asp Gln Ile Trp Asn Asn Met
            580                 585                 590

Thr Trp Met Glu Trp Glu Arg Glu Ile Asp Asn Tyr Thr Asn Leu Ile
```

```
            595                 600                 605
Tyr Thr Leu Ile Glu Glu Ser Gln Asn Gln Gln Glu Lys Asn Glu Gln
610                 615                 620

Glu Leu Leu Glu Leu Asp Lys Trp Ala Ser Leu Trp Asn Trp Phe Asp
625                 630                 635                 640

Ile Ser Lys Trp Leu Trp Tyr Ile Lys Leu Gln Gly Leu Ala Glu Gln
                645                 650                 655

Ala Ala Leu Ser Gly Leu Phe Gln Pro Tyr Asn Val Gly Arg Phe Asn
                660                 665                 670

Val Thr Ala Ala Val Gly Gly Tyr Lys Ser Glu Ser Ala Val Ala Ile
            675                 680                 685

Gly Thr Gly Phe Arg Phe Thr Glu Asn Phe Ala Ala Lys Ala Gly Val
690                 695                 700

Ala Val Gly Thr Ser Ser Gly Ser Ser Ala Ala Tyr His Val Gly Val
705                 710                 715                 720

Asn Tyr Glu Trp

<210> SEQ ID NO 9
<211> LENGTH: 758
<212> TYPE: PRT
<213> ORGANISM: Artificial Sequence
<220> FEATURE:
<223> OTHER INFORMATION: NadA-gp120 hybrid

<400> SEQUENCE: 9

Met Lys His Phe Pro Ser Lys Val Leu Thr Thr Ala Ile Leu Ala Thr
1               5                   10                  15

Phe Cys Ser Gly Ala Leu Ala Ala Ser Asn Asp Asp Ser Ala Val
                20                  25                  30

Glu Lys Leu Trp Val Thr Val Tyr Tyr Gly Val Pro Val Trp Lys Glu
            35                  40                  45

Ala Thr Thr Thr Leu Phe Cys Ala Ser Asp Ala Lys Ala Tyr Asp Thr
        50                  55                  60

Glu Val His Asn Val Trp Ala Thr His Ala Cys Val Pro Thr Asp Pro
65                  70                  75                  80

Asn Pro Gln Glu Ile Val Leu Glu Asn Val Thr Glu Asn Phe Asn Met
                85                  90                  95

Trp Lys Asn Asn Met Val Glu Gln Met His Glu Asp Ile Ile Ser Leu
                100                 105                 110

Trp Asp Gln Ser Leu Lys Pro Cys Val Lys Leu Thr Pro Leu Cys Val
            115                 120                 125

Thr Leu His Cys Thr Asn Leu Lys Asn Ala Thr Asn Thr Lys Ser Ser
        130                 135                 140

Asn Trp Lys Glu Met Asp Arg Gly Glu Ile Lys Asn Cys Ser Phe Lys
145                 150                 155                 160

Val Gly Ala Gly Lys Leu Ile Asn Cys Asn Thr Ser Val Ile Thr Gln
                165                 170                 175

Ala Cys Pro Lys Val Ser Phe Glu Pro Ile Pro Ile His Tyr Cys Ala
            180                 185                 190

Pro Ala Gly Phe Ala Ile Leu Lys Cys Asn Asp Lys Lys Phe Asn Gly
        195                 200                 205

Ser Gly Pro Cys Thr Asn Val Ser Thr Val Gln Cys Thr His Gly Ile
    210                 215                 220

Arg Pro Val Val Ser Thr Gln Leu Leu Leu Asn Gly Ser Leu Ala Glu
225                 230                 235                 240
```

-continued

```
Glu Gly Val Val Ile Arg Ser Glu Asn Phe Thr Asp Asn Ala Lys Thr
            245                 250                 255

Ile Ile Val Gln Leu Lys Glu Ser Val Glu Ile Asn Cys Thr Arg Pro
            260                 265                 270

Asn Asn Asn Thr Arg Lys Ser Ile Thr Ile Gly Pro Gly Arg Ala Phe
            275                 280                 285

Tyr Ala Thr Gly Asp Ile Ile Gly Asp Ile Arg Gln Ala His Cys Asn
            290                 295                 300

Ile Ser Gly Glu Lys Trp Asn Asn Thr Leu Lys Gln Ile Val Thr Lys
305                 310                 315                 320

Leu Gln Ala Gln Phe Gly Asn Lys Thr Ile Val Phe Lys Gln Ser Ser
            325                 330                 335

Gly Gly Asp Pro Glu Ile Val Met His Ser Phe Asn Cys Gly Gly Glu
            340                 345                 350

Phe Phe Tyr Cys Asn Ser Thr Gln Leu Phe Asn Ser Thr Trp Asn Asn
            355                 360                 365

Thr Ile Gly Pro Asn Asn Thr Asn Gly Thr Ile Thr Leu Pro Cys Arg
            370                 375                 380

Ile Lys Gln Ile Ile Asn Arg Trp Gln Glu Val Gly Lys Ala Met Tyr
385                 390                 395                 400

Ala Pro Pro Ile Arg Gly Gln Ile Arg Cys Ser Ser Asn Ile Thr Gly
            405                 410                 415

Leu Leu Leu Thr Arg Asp Gly Gly Lys Glu Ile Ser Asn Thr Thr Glu
            420                 425                 430

Ile Phe Arg Pro Gly Gly Gly Asp Met Arg Asp Asn Trp Arg Ser Glu
            435                 440                 445

Leu Tyr Lys Tyr Lys Val Val Lys Ile Glu Pro Leu Gly Val Ala Pro
            450                 455                 460

Thr Lys Ala Ile Ser Ser Val Gln Ser Glu Lys Ser Ala Val Thr
465                 470                 475                 480

Leu Gly Ala Met Phe Leu Gly Phe Leu Gly Ala Ala Gly Ser Thr Met
            485                 490                 495

Gly Ala Arg Ser Leu Thr Leu Thr Val Gln Ala Arg Gln Leu Leu Ser
            500                 505                 510

Gly Ile Val Gln Gln Gln Asn Asn Leu Leu Arg Ala Ile Glu Ala Gln
            515                 520                 525

Gln His Leu Leu Gln Leu Thr Val Trp Gly Ile Lys Gln Leu Gln Ala
            530                 535                 540

Arg Val Leu Ala Val Glu Arg Tyr Leu Lys Asp Gln Gln Leu Leu Gly
545                 550                 555                 560

Ile Trp Gly Cys Ser Gly Lys Leu Ile Cys Thr Thr Ala Val Pro Trp
            565                 570                 575

Asn Ala Ser Trp Ser Asn Lys Ser Leu Asp Gln Ile Trp Asn Asn Met
            580                 585                 590

Thr Trp Met Glu Trp Glu Arg Glu Ile Asp Asn Tyr Thr Asn Leu Ile
            595                 600                 605

Tyr Thr Leu Ile Glu Glu Ser Gln Asn Gln Gln Glu Lys Asn Glu Gln
            610                 615                 620

Glu Leu Leu Glu Leu Asp Lys Trp Ala Ser Leu Trp Asn Trp Phe Asp
625                 630                 635                 640

Ile Ser Lys Trp Leu Trp Tyr Ile Lys Leu Leu Asp Thr Arg Leu Ala
            645                 650                 655

Ser Ala Glu Lys Ser Ile Ala Asp His Asp Thr Arg Leu Asn Gly Leu
            660                 665                 670
```

Asp Lys Thr Val Ser Asp Leu Arg Lys Glu Thr Arg Gln Gly Leu Ala
            675                 680                 685

Glu Gln Ala Ala Leu Ser Gly Leu Phe Gln Pro Tyr Asn Val Gly Arg
        690                 695                 700

Phe Asn Val Thr Ala Val Gly Gly Tyr Lys Ser Glu Ser Ala Val
705                 710                 715                 720

Ala Ile Gly Thr Gly Phe Arg Phe Thr Glu Asn Phe Ala Ala Lys Ala
            725                 730                 735

Gly Val Ala Val Gly Thr Ser Ser Gly Ser Ser Ala Ala Tyr His Val
            740                 745                 750

Gly Val Asn Tyr Glu Trp
            755

<210> SEQ ID NO 10
<211> LENGTH: 648
<212> TYPE: PRT
<213> ORGANISM: Artificial Sequence
<220> FEATURE:
<223> OTHER INFORMATION: HIV gp140deltaV2 with N.meningitidis NadA
      leader

<400> SEQUENCE: 10

Met Lys His Phe Pro Ser Lys Val Leu Thr Thr Ala Ile Leu Ala Thr
1               5                   10                  15

Phe Cys Ser Gly Ala Leu Ala Ala Ser Asn Asp Asp Asp Ser Ala Val
20 25 30

Glu Lys Leu Trp Val Thr Val Tyr Tyr Gly Val Pro Val Trp Lys Glu
35 40 45

Ala Thr Thr Thr Leu Phe Cys Ala Ser Asp Ala Lys Ala Tyr Asp Thr
50 55 60

Glu Val His Asn Val Trp Ala Thr His Ala Cys Val Pro Thr Asp Pro
65 70 75 80

Asn Pro Gln Glu Ile Val Leu Glu Asn Val Thr Glu Asn Phe Asn Met
85 90 95

Trp Lys Asn Asn Met Val Glu Gln Met His Glu Asp Ile Ile Ser Leu
100 105 110

Trp Asp Gln Ser Leu Lys Pro Cys Val Lys Leu Thr Pro Leu Cys Val
115 120 125

Thr Leu His Cys Thr Asn Leu Lys Asn Ala Thr Asn Thr Lys Ser Ser
130 135 140

Asn Trp Lys Glu Met Asp Arg Gly Glu Ile Lys Asn Cys Ser Phe Lys
145 150 155 160

Val Gly Ala Gly Lys Leu Ile Asn Cys Asn Thr Ser Val Ile Thr Gln
165 170 175

Ala Cys Pro Lys Val Ser Phe Glu Pro Ile Pro Ile His Tyr Cys Ala
180 185 190

Pro Ala Gly Phe Ala Ile Leu Lys Cys Asn Asp Lys Lys Phe Asn Gly
195 200 205

Ser Gly Pro Cys Thr Asn Val Ser Thr Val Gln Cys Thr His Gly Ile
210 215 220

Arg Pro Val Val Ser Thr Gln Leu Leu Leu Asn Gly Ser Leu Ala Glu
225 230 235 240

Glu Gly Val Val Ile Arg Ser Glu Asn Phe Thr Asp Asn Ala Lys Thr
245 250 255

Ile Ile Val Gln Leu Lys Glu Ser Val Glu Ile Asn Cys Thr Arg Pro
260 265 270

```
Asn Asn Asn Thr Arg Lys Ser Ile Thr Ile Gly Pro Gly Arg Ala Phe
            275                 280                 285

Tyr Ala Thr Gly Asp Ile Ile Gly Asp Ile Arg Gln Ala His Cys Asn
        290                 295                 300

Ile Ser Gly Glu Lys Trp Asn Asn Thr Leu Lys Gln Ile Val Thr Lys
305                 310                 315                 320

Leu Gln Ala Gln Phe Gly Asn Lys Thr Ile Val Phe Lys Gln Ser Ser
                325                 330                 335

Gly Gly Asp Pro Glu Ile Val Met His Ser Phe Asn Cys Gly Gly Glu
                340                 345                 350

Phe Phe Tyr Cys Asn Ser Thr Gln Leu Phe Asn Ser Thr Trp Asn Asn
            355                 360                 365

Thr Ile Gly Pro Asn Asn Thr Asn Gly Thr Ile Thr Leu Pro Cys Arg
        370                 375                 380

Ile Lys Gln Ile Ile Asn Arg Trp Gln Glu Val Gly Lys Ala Met Tyr
385                 390                 395                 400

Ala Pro Pro Ile Arg Gly Gln Ile Arg Cys Ser Ser Asn Ile Thr Gly
                405                 410                 415

Leu Leu Leu Thr Arg Asp Gly Gly Lys Glu Ile Ser Asn Thr Thr Glu
                420                 425                 430

Ile Phe Arg Pro Gly Gly Gly Asp Met Arg Asp Asn Trp Arg Ser Glu
            435                 440                 445

Leu Tyr Lys Tyr Lys Val Val Lys Ile Glu Pro Leu Gly Val Ala Pro
        450                 455                 460

Thr Lys Ala Ile Ser Ser Val Gln Ser Glu Lys Ser Ala Val Thr
465                 470                 475                 480

Leu Gly Ala Met Phe Leu Gly Phe Leu Gly Ala Ala Gly Ser Thr Met
                485                 490                 495

Gly Ala Arg Ser Leu Thr Leu Thr Val Gln Ala Arg Gln Leu Leu Ser
            500                 505                 510

Gly Ile Val Gln Gln Gln Asn Asn Leu Leu Arg Ala Ile Glu Ala Gln
        515                 520                 525

Gln His Leu Leu Gln Leu Thr Val Trp Gly Ile Lys Gln Leu Gln Ala
530                 535                 540

Arg Val Leu Ala Val Glu Arg Tyr Leu Lys Asp Gln Gln Leu Leu Gly
545                 550                 555                 560

Ile Trp Gly Cys Ser Gly Lys Leu Ile Cys Thr Thr Ala Val Pro Trp
                565                 570                 575

Asn Ala Ser Trp Ser Asn Lys Ser Leu Asp Gln Ile Trp Asn Asn Met
            580                 585                 590

Thr Trp Met Glu Trp Glu Arg Glu Ile Asp Asn Tyr Thr Asn Leu Ile
        595                 600                 605

Tyr Thr Leu Ile Glu Glu Ser Gln Asn Gln Gln Glu Lys Asn Glu Gln
610                 615                 620

Glu Leu Leu Glu Leu Asp Lys Trp Ala Ser Leu Trp Asn Trp Phe Asp
625                 630                 635                 640

Ile Ser Lys Trp Leu Trp Tyr Ile
                645

<210> SEQ ID NO 11
<211> LENGTH: 29
<212> TYPE: PRT
<213> ORGANISM: Neisseria meningitidis

<400> SEQUENCE: 11
```

```
Met Lys His Phe Pro Ser Lys Val Leu Thr Thr Ala Ile Leu Ala Thr
1               5                   10                  15

Phe Cys Ser Gly Ala Leu Ala Ala Ser Asn Asp Asp Asp
                20                  25

<210> SEQ ID NO 12
<211> LENGTH: 475
<212> TYPE: PRT
<213> ORGANISM: Human immunodeficiency virus

<400> SEQUENCE: 12

Ser Ala Val Glu Lys Leu Trp Val Thr Val Tyr Tyr Gly Val Pro Val
1               5                   10                  15

Trp Lys Glu Ala Thr Thr Thr Leu Phe Cys Ala Ser Asp Ala Lys Ala
                20                  25                  30

Tyr Asp Thr Glu Val His Asn Val Trp Ala Thr His Ala Cys Val Pro
            35                  40                  45

Thr Asp Pro Asn Pro Gln Glu Ile Val Leu Glu Asn Val Thr Glu Asn
    50                  55                  60

Phe Asn Met Trp Lys Asn Asn Met Val Glu Gln Met His Glu Asp Ile
65                  70                  75                  80

Ile Ser Leu Trp Asp Gln Ser Leu Lys Pro Cys Val Lys Leu Thr Pro
                85                  90                  95

Leu Cys Val Thr Leu His Cys Thr Asn Leu Lys Asn Ala Thr Asn Thr
                100                 105                 110

Lys Ser Ser Asn Trp Lys Glu Met Asp Arg Gly Glu Ile Lys Asn Cys
            115                 120                 125

Ser Phe Lys Val Thr Thr Ser Ile Arg Asn Lys Met Gln Lys Glu Tyr
    130                 135                 140

Ala Leu Phe Tyr Lys Leu Asp Val Val Pro Ile Asp Asn Asp Asn Thr
145                 150                 155                 160

Ser Tyr Lys Leu Ile Asn Cys Asn Thr Ser Val Ile Thr Gln Ala Cys
                165                 170                 175

Pro Lys Val Ser Phe Glu Pro Ile Pro Ile His Tyr Cys Ala Pro Ala
            180                 185                 190

Gly Phe Ala Ile Leu Lys Cys Asn Asp Lys Lys Phe Asn Gly Ser Gly
    195                 200                 205

Pro Cys Thr Asn Val Ser Thr Val Gln Cys Thr His Gly Ile Arg Pro
210                 215                 220

Val Val Ser Thr Gln Leu Leu Leu Asn Gly Ser Leu Ala Glu Glu Gly
225                 230                 235                 240

Val Val Ile Arg Ser Glu Asn Phe Thr Asp Asn Ala Lys Thr Ile Ile
                245                 250                 255

Val Gln Leu Lys Glu Ser Val Glu Ile Asn Cys Thr Arg Pro Asn Asn
            260                 265                 270

Asn Thr Arg Lys Ser Ile Thr Ile Gly Pro Gly Arg Ala Phe Tyr Ala
    275                 280                 285

Thr Gly Asp Ile Ile Gly Asp Ile Arg Gln Ala His Cys Asn Ile Ser
290                 295                 300

Gly Glu Lys Trp Asn Asn Thr Leu Lys Gln Ile Val Thr Lys Leu Gln
305                 310                 315                 320

Ala Gln Phe Gly Asn Lys Thr Ile Val Phe Lys Gln Ser Ser Gly Gly
                325                 330                 335

Asp Pro Glu Ile Val Met His Ser Phe Asn Cys Gly Gly Glu Phe Phe
            340                 345                 350
```

```
Tyr Cys Asn Ser Thr Gln Leu Phe Asn Ser Thr Trp Asn Asn Thr Ile
            355                 360                 365

Gly Pro Asn Asn Thr Asn Gly Thr Ile Thr Leu Pro Cys Arg Ile Lys
        370                 375                 380

Gln Ile Ile Asn Arg Trp Gln Glu Val Gly Lys Ala Met Tyr Ala Pro
385                 390                 395                 400

Pro Ile Arg Gly Gln Ile Arg Cys Ser Ser Asn Ile Thr Gly Leu Leu
                405                 410                 415

Leu Thr Arg Asp Gly Gly Lys Glu Ile Ser Asn Thr Thr Glu Ile Phe
            420                 425                 430

Arg Pro Gly Gly Gly Asp Met Arg Asp Asn Trp Arg Ser Glu Leu Tyr
            435                 440                 445

Lys Tyr Lys Val Val Lys Ile Glu Pro Leu Gly Val Ala Pro Thr Lys
        450                 455                 460

Ala Lys Arg Arg Val Val Gln Arg Glu Lys Arg
465                 470                 475

<210> SEQ ID NO 13
<211> LENGTH: 263
<212> TYPE: PRT
<213> ORGANISM: Neisseria meningitidis

<400> SEQUENCE: 13

Lys Val Val Thr Asn Leu Thr Lys Thr Val Asn Glu Asn Lys Gln Asn
1               5                   10                  15

Val Asp Ala Lys Val Lys Ala Ala Glu Ser Glu Ile Glu Lys Leu Thr
            20                  25                  30

Thr Lys Leu Ala Asp Thr Asp Ala Ala Leu Ala Asp Thr Asp Ala Ala
        35                  40                  45

Leu Asp Ala Thr Thr Asn Ala Leu Asn Lys Leu Gly Glu Asn Ile Thr
    50                  55                  60

Thr Phe Ala Glu Glu Thr Lys Thr Asn Ile Val Lys Ile Asp Glu Lys
65                  70                  75                  80

Leu Glu Ala Val Ala Asp Thr Val Asp Lys His Ala Glu Ala Phe Asn
                85                  90                  95

Asp Ile Ala Asp Ser Leu Asp Glu Thr Asn Thr Lys Ala Asp Glu Ala
            100                 105                 110

Val Lys Thr Ala Asn Glu Ala Lys Gln Thr Ala Glu Glu Thr Lys Gln
        115                 120                 125

Asn Val Asp Ala Lys Val Lys Ala Ala Glu Thr Ala Gly Lys Ala
130                 135                 140

Glu Ala Ala Ala Gly Thr Ala Asn Thr Ala Ala Asp Lys Ala Glu Ala
145                 150                 155                 160

Val Ala Ala Lys Val Thr Asp Ile Lys Ala Asp Ile Ala Thr Asn Lys
                165                 170                 175

Asp Asn Ile Ala Lys Lys Ala Asn Ser Ala Asp Val Tyr Thr Arg Glu
            180                 185                 190

Glu Ser Asp Ser Lys Phe Val Arg Ile Asp Gly Leu Asn Ala Thr Thr
        195                 200                 205

Glu Lys Leu Asp Thr Arg Leu Ala Ser Ala Glu Lys Ser Ile Ala Asp
    210                 215                 220

His Asp Thr Arg Leu Asn Gly Leu Asp Lys Thr Val Ser Asp Leu Arg
225                 230                 235                 240

Lys Glu Thr Arg Gln Gly Leu Ala Glu Gln Ala Ala Leu Ser Gly Leu
                245                 250                 255
```

Phe Gln Pro Tyr Asn Val Gly
            260

<210> SEQ ID NO 14
<211> LENGTH: 2
<212> TYPE: PRT
<213> ORGANISM: Artificial Sequence
<220> FEATURE:
<223> OTHER INFORMATION: Dipeptide linker

<400> SEQUENCE: 14

Gly Ser
1

<210> SEQ ID NO 15
<211> LENGTH: 55
<212> TYPE: PRT
<213> ORGANISM: Neisseria meningitidis

<400> SEQUENCE: 15

Arg Phe Asn Val Thr Ala Ala Val Gly Gly Tyr Lys Ser Glu Ser Ala
1               5                   10                  15

Val Ala Ile Gly Thr Gly Phe Arg Phe Thr Glu Asn Phe Ala Ala Lys
            20                  25                  30

Ala Gly Val Ala Val Gly Thr Ser Ser Gly Ser Ser Ala Ala Tyr His
        35                  40                  45

Val Gly Val Asn Tyr Glu Trp
    50                  55

<210> SEQ ID NO 16
<211> LENGTH: 448
<212> TYPE: PRT
<213> ORGANISM: Human immunodeficiency virus

<400> SEQUENCE: 16

Ser Ala Val Glu Lys Leu Trp Val Thr Val Tyr Tyr Gly Val Pro Val
1               5                   10                  15

Trp Lys Glu Ala Thr Thr Thr Leu Phe Cys Ala Ser Asp Ala Lys Ala
            20                  25                  30

Tyr Asp Thr Glu Val His Asn Val Trp Ala Thr His Ala Cys Val Pro
        35                  40                  45

Thr Asp Pro Asn Pro Gln Glu Ile Val Leu Glu Asn Val Thr Glu Asn
    50                  55                  60

Phe Asn Met Trp Lys Asn Met Val Glu Gln Met His Glu Asp Ile
65                  70                  75                  80

Ile Ser Leu Trp Asp Gln Ser Leu Lys Pro Cys Val Lys Leu Thr Pro
            85                  90                  95

Leu Cys Val Thr Leu His Cys Thr Asn Leu Lys Asn Ala Thr Asn Thr
        100                 105                 110

Lys Ser Ser Asn Trp Lys Glu Met Asp Arg Gly Glu Ile Lys Asn Cys
    115                 120                 125

Ser Phe Lys Val Gly Ala Gly Lys Leu Ile Asn Cys Asn Thr Ser Val
    130                 135                 140

Ile Thr Gln Ala Cys Pro Lys Val Ser Phe Glu Pro Ile Pro Ile His
145                 150                 155                 160

Tyr Cys Ala Pro Ala Gly Phe Ala Ile Leu Lys Cys Asn Asp Lys Lys
                165                 170                 175

Phe Asn Gly Ser Gly Pro Cys Thr Asn Val Ser Thr Val Gln Cys Thr
            180                 185                 190

His Gly Ile Arg Pro Val Val Ser Thr Gln Leu Leu Asn Gly Ser
            195                 200                 205

Leu Ala Glu Glu Gly Val Val Ile Arg Ser Glu Asn Phe Thr Asp Asn
    210                 215                 220

Ala Lys Thr Ile Ile Val Gln Leu Lys Glu Ser Val Glu Ile Asn Cys
225                 230                 235                 240

Thr Arg Pro Asn Asn Asn Thr Arg Lys Ser Ile Thr Ile Gly Pro Gly
                245                 250                 255

Arg Ala Phe Tyr Ala Thr Gly Asp Ile Ile Gly Asp Ile Arg Gln Ala
            260                 265                 270

His Cys Asn Ile Ser Gly Glu Lys Trp Asn Asn Thr Leu Lys Gln Ile
        275                 280                 285

Val Thr Lys Leu Gln Ala Gln Phe Gly Asn Lys Thr Ile Val Phe Lys
    290                 295                 300

Gln Ser Ser Gly Gly Asp Pro Glu Ile Val Met His Ser Phe Asn Cys
305                 310                 315                 320

Gly Gly Glu Phe Phe Tyr Cys Asn Ser Thr Gln Leu Phe Asn Ser Thr
                325                 330                 335

Trp Asn Asn Thr Ile Gly Pro Asn Asn Thr Asn Gly Thr Ile Thr Leu
            340                 345                 350

Pro Cys Arg Ile Lys Gln Ile Ile Asn Arg Trp Gln Glu Val Gly Lys
        355                 360                 365

Ala Met Tyr Ala Pro Pro Ile Arg Gly Gln Ile Arg Cys Ser Ser Asn
    370                 375                 380

Ile Thr Gly Leu Leu Leu Thr Arg Asp Gly Gly Lys Glu Ile Ser Asn
385                 390                 395                 400

Thr Thr Glu Ile Phe Arg Pro Gly Gly Gly Asp Met Arg Asp Asn Trp
                405                 410                 415

Arg Ser Glu Leu Tyr Lys Tyr Lys Val Val Lys Ile Glu Pro Leu Gly
            420                 425                 430

Val Ala Pro Thr Lys Ala Ile Ser Ser Val Val Gln Ser Glu Lys Ser
        435                 440                 445

<210> SEQ ID NO 17
<211> LENGTH: 171
<212> TYPE: PRT
<213> ORGANISM: Human immunodeficiency virus

<400> SEQUENCE: 17

Ala Val Thr Leu Gly Ala Met Phe Leu Gly Phe Leu Gly Ala Ala Gly
1               5                   10                  15

Ser Thr Met Gly Ala Arg Ser Leu Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Val Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Asp Gln Ile Trp
            100                 105                 110

Asn Asn Met Thr Trp Met Glu Trp Glu Arg Glu Ile Asp Asn Tyr Thr
        115                 120                 125

```
Asn Leu Ile Tyr Thr Leu Ile Glu Glu Ser Gln Asn Gln Gln Glu Lys
        130                 135                 140

Asn Glu Gln Glu Leu Leu Glu Leu Asp Lys Trp Ala Ser Leu Trp Asn
145                 150                 155                 160

Trp Phe Asp Ile Ser Lys Trp Leu Trp Tyr Ile
                165                 170

<210> SEQ ID NO 18
<211> LENGTH: 2
<212> TYPE: PRT
<213> ORGANISM: Artificial Sequence
<220> FEATURE:
<223> OTHER INFORMATION: Dipeptide linker

<400> SEQUENCE: 18

Lys Leu
1

<210> SEQ ID NO 19
<211> LENGTH: 74
<212> TYPE: PRT
<213> ORGANISM: Neisseria meningitidis

<400> SEQUENCE: 19

Gln Gly Leu Ala Glu Gln Ala Ala Leu Ser Gly Leu Phe Gln Pro Tyr
1               5                   10                  15

Asn Val Gly Arg Phe Asn Val Thr Ala Ala Val Gly Gly Tyr Lys Ser
            20                  25                  30

Glu Ser Ala Val Ala Ile Gly Thr Gly Phe Arg Phe Thr Glu Asn Phe
        35                  40                  45

Ala Ala Lys Ala Gly Val Ala Val Gly Thr Ser Ser Gly Ser Ser Ala
    50                  55                  60

Ala Tyr His Val Gly Val Asn Tyr Glu Trp
65                  70

<210> SEQ ID NO 20
<211> LENGTH: 108
<212> TYPE: PRT
<213> ORGANISM: Neisseria meningitidis

<400> SEQUENCE: 20

Leu Asp Thr Arg Leu Ala Ser Ala Glu Lys Ser Ile Ala Asp His Asp
1               5                   10                  15

Thr Arg Leu Asn Gly Leu Asp Lys Thr Val Ser Asp Leu Arg Lys Glu
            20                  25                  30

Thr Arg Gln Gly Leu Ala Glu Gln Ala Ala Leu Ser Gly Leu Phe Gln
        35                  40                  45

Pro Tyr Asn Val Gly Arg Phe Asn Val Thr Ala Ala Val Gly Gly Tyr
    50                  55                  60

Lys Ser Glu Ser Ala Val Ala Ile Gly Thr Gly Phe Arg Phe Thr Glu
65                  70                  75                  80

Asn Phe Ala Ala Lys Ala Gly Val Ala Val Gly Thr Ser Ser Gly Ser
                85                  90                  95

Ser Ala Ala Tyr His Val Gly Val Asn Tyr Glu Trp
            100                 105

<210> SEQ ID NO 21
<211> LENGTH: 464
<212> TYPE: PRT
<213> ORGANISM: Neisseria meningitidis
```

```
<400> SEQUENCE: 21

Ser Pro Asp Val Lys Ser Ala Asp Thr Leu Ser Lys Pro Ala Ala Pro
1               5                   10                  15

Val Val Ser Glu Lys Glu Thr Glu Ala Lys Glu Asp Ala Pro Gln Ala
            20                  25                  30

Gly Ser Gln Gly Gln Gly Ala Pro Ser Ala Gln Gly Ser Gln Asp Met
        35                  40                  45

Ala Ala Val Ser Glu Glu Asn Thr Gly Asn Gly Gly Ala Val Thr Ala
    50                  55                  60

Asp Asn Pro Lys Asn Glu Asp Val Ala Gln Asn Asp Met Pro Gln
65                  70                  75                  80

Asn Ala Ala Gly Thr Asp Ser Ser Thr Pro Asn His Thr Pro Asp Pro
                85                  90                  95

Asn Met Leu Ala Gly Asn Met Glu Asn Gln Ala Thr Asp Ala Gly Glu
            100                 105                 110

Ser Ser Gln Pro Ala Asn Gln Pro Asp Met Ala Asn Ala Ala Asp Gly
        115                 120                 125

Met Gln Gly Asp Asp Pro Ser Ala Gly Gly Asn Ala Gly Asn Thr
130                 135                 140

Ala Ala Gln Gly Ala Asn Gln Ala Gly Asn Asn Gln Ala Ala Gly Ser
145                 150                 155                 160

Ser Asp Pro Ile Pro Ala Ser Asn Pro Ala Pro Ala Asn Gly Gly Ser
                165                 170                 175

Asn Phe Gly Arg Val Asp Leu Ala Asn Gly Val Leu Ile Asp Gly Pro
            180                 185                 190

Ser Gln Asn Ile Thr Leu Thr His Cys Lys Gly Asp Ser Cys Ser Gly
        195                 200                 205

Asn Asn Phe Leu Asp Glu Glu Val Gln Leu Lys Ser Glu Phe Glu Lys
    210                 215                 220

Leu Ser Asp Ala Asp Lys Ile Ser Asn Tyr Lys Lys Asp Gly Lys Asn
225                 230                 235                 240

Asp Lys Phe Val Gly Leu Val Ala Asp Ser Val Gln Met Lys Gly Ile
                245                 250                 255

Asn Gln Tyr Ile Ile Phe Tyr Lys Pro Lys Pro Thr Ser Phe Ala Arg
            260                 265                 270

Phe Arg Arg Ser Ala Arg Ser Arg Arg Ser Leu Pro Ala Glu Met Pro
        275                 280                 285

Leu Ile Pro Val Asn Gln Ala Asp Thr Leu Ile Val Asp Gly Glu Ala
290                 295                 300

Val Ser Leu Thr Gly His Ser Gly Asn Ile Phe Ala Pro Glu Gly Asn
305                 310                 315                 320

Tyr Arg Tyr Leu Thr Tyr Gly Ala Glu Lys Leu Pro Gly Gly Ser Tyr
                325                 330                 335

Ala Leu Arg Val Gln Gly Glu Pro Ala Lys Gly Glu Met Leu Ala Gly
            340                 345                 350

Ala Ala Val Tyr Asn Gly Glu Val Leu His Phe His Thr Glu Asn Gly
        355                 360                 365

Arg Pro Tyr Pro Thr Arg Gly Arg Phe Ala Ala Lys Val Asp Phe Gly
    370                 375                 380

Ser Lys Ser Val Asp Gly Ile Ile Asp Ser Gly Asp Leu His Met
385                 390                 395                 400

Gly Thr Gln Lys Phe Lys Ala Ala Ile Asp Gly Asn Gly Phe Lys Gly
                405                 410                 415
```

```
Thr Trp Thr Glu Asn Gly Ser Gly Asp Val Ser Gly Lys Phe Tyr Gly
                420                 425                 430

Pro Ala Gly Glu Glu Val Ala Gly Lys Tyr Ser Tyr Arg Pro Thr Asp
            435                 440                 445

Ala Glu Lys Gly Gly Phe Gly Val Phe Ala Gly Lys Lys Glu Gln Asp
        450                 455                 460

<210> SEQ ID NO 22
<211> LENGTH: 179
<212> TYPE: PRT
<213> ORGANISM: Neisseria meningitidis

<400> SEQUENCE: 22

Val Ser Ala Val Ile Gly Ser Ala Ala Val Gly Ala Lys Ser Ala Val
1               5                   10                  15

Asp Arg Arg Thr Thr Gly Ala Gln Thr Asp Asp Asn Val Met Ala Leu
            20                  25                  30

Arg Ile Glu Thr Thr Ala Arg Ser Tyr Leu Arg Gln Asn Asn Gln Thr
        35                  40                  45

Lys Gly Tyr Thr Pro Gln Ile Ser Val Val Gly Tyr Asn Arg His Leu
    50                  55                  60

Leu Leu Leu Gly Gln Val Ala Thr Glu Gly Glu Lys Gln Phe Val Gly
65                  70                  75                  80

Gln Ile Ala Arg Ser Glu Ala Ala Glu Gly Val Tyr Asn Tyr Ile
                85                  90                  95

Thr Val Ala Ser Leu Pro Arg Thr Ala Gly Asp Ile Ala Gly Asp Thr
            100                 105                 110

Trp Asn Thr Ser Lys Val Arg Ala Thr Leu Leu Gly Ile Ser Pro Ala
        115                 120                 125

Thr Gln Ala Arg Val Lys Ile Val Thr Tyr Gly Asn Val Thr Tyr Val
    130                 135                 140

Met Gly Ile Leu Thr Pro Glu Glu Gln Ala Gln Ile Thr Gln Lys Val
145                 150                 155                 160

Ser Thr Thr Val Gly Val Gln Lys Val Ile Thr Leu Tyr Gln Asn Tyr
                165                 170                 175

Val Gln Arg

<210> SEQ ID NO 23
<211> LENGTH: 255
<212> TYPE: PRT
<213> ORGANISM: Neisseria meningitidis

<400> SEQUENCE: 23

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
```

```
            100                 105                 110
Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 24
<211> LENGTH: 254
<212> TYPE: PRT
<213> ORGANISM: Neisseria meningitidis

<400> SEQUENCE: 24

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
```

```
225                 230                 235                 240

Ile Gly Glu Lys Val His Glu Ile Gly Ile Ala Gly Lys Gln
                245                 250

<210> SEQ ID NO 25
<211> LENGTH: 262
<212> TYPE: PRT
<213> ORGANISM: Neisseria meningitidis

<400> SEQUENCE: 25

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 26
<211> LENGTH: 168
<212> TYPE: PRT
<213> ORGANISM: Neisseria meningitidis

<400> SEQUENCE: 26

Ala Thr Tyr Lys Val Asp Glu Tyr His Ala Asn Ala Arg Phe Ala Ile
1               5                   10                  15

Asp His Phe Asn Thr Ser Thr Asn Val Gly Gly Phe Tyr Gly Leu Thr
                20                  25                  30

Gly Ser Val Glu Phe Asp Gln Ala Lys Arg Asp Gly Lys Ile Asp Ile
            35                  40                  45
```

```
Thr Ile Pro Ile Ala Asn Leu Gln Ser Gly Ser Gln His Phe Thr Asp
            50                  55                  60

His Leu Lys Ser Ala Asp Ile Phe Asp Ala Ala Gln Tyr Pro Asp Ile
 65                  70                  75                  80

Arg Phe Val Ser Thr Lys Phe Asn Phe Asn Gly Lys Lys Leu Val Ser
                 85                  90                  95

Val Asp Gly Asn Leu Thr Met His Gly Lys Thr Ala Pro Val Lys Leu
            100                 105                 110

Lys Ala Glu Lys Phe Asn Cys Tyr Gln Ser Pro Met Glu Lys Thr Glu
            115                 120                 125

Val Cys Gly Gly Asp Phe Ser Thr Thr Ile Asp Arg Thr Lys Trp Gly
            130                 135                 140

Met Asp Tyr Leu Val Asn Val Gly Met Thr Lys Ser Val Arg Ile Asp
145                 150                 155                 160

Ile Gln Ile Glu Ala Ala Lys Gln
                165

<210> SEQ ID NO 27
<211> LENGTH: 6
<212> TYPE: PRT
<213> ORGANISM: Artificial Sequence
<220> FEATURE:
<223> OTHER INFORMATION: Glycine-rich linker

<400> SEQUENCE: 27

Gly Ser Gly Gly Gly Gly
1               5

<210> SEQ ID NO 28
<211> LENGTH: 405
<212> TYPE: PRT
<213> ORGANISM: Neisseria meningitidis

<400> SEQUENCE: 28

Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Asp Val Glu Ala Asp Asp
 65                 70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
            115                 120                 125

Leu Ala Asp Thr Asp Ala Ala Leu Asp Ala Thr Thr Asn Ala Leu Asn
            130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
```

```
                        180              185               190
Asn Thr Lys Ala Asp Glu Ala Val Lys Thr Ala Asn Glu Ala Lys Gln
                195                 200                 205
Thr Ala Glu Glu Thr Lys Gln Asn Val Asp Ala Lys Val Lys Ala Ala
            210                 215                 220
Glu Thr Ala Ala Gly Lys Ala Glu Ala Ala Gly Thr Ala Asn Thr
225                 230                 235                 240
Ala Ala Asp Lys Ala Glu Ala Val Ala Lys Val Thr Asp Ile Lys
                245                 250                 255
Ala Asp Ile Ala Thr Asn Lys Asp Asn Ile Ala Lys Lys Ala Asn Ser
                260                 265                 270
Ala Asp Val Tyr Thr Arg Glu Glu Ser Asp Ser Lys Phe Val Arg Ile
                275                 280                 285
Asp Gly Leu Asn Ala Thr Thr Glu Lys Leu Asp Thr Arg Leu Ala Ser
            290                 295                 300
Ala Glu Lys Ser Ile Ala Asp His Asp Thr Arg Leu Asn Gly Leu Asp
305                 310                 315                 320
Lys Thr Val Ser Asp Leu Arg Lys Glu Thr Arg Gln Gly Leu Ala Glu
                325                 330                 335
Gln Ala Ala Leu Ser Gly Leu Phe Gln Pro Tyr Asn Val Gly Arg Phe
            340                 345                 350
Asn Val Thr Ala Ala Val Gly Gly Tyr Lys Ser Glu Ser Ala Val Ala
            355                 360                 365
Ile Gly Thr Gly Phe Arg Phe Thr Glu Asn Phe Ala Ala Lys Ala Gly
            370                 375                 380
Val Ala Val Gly Thr Ser Ser Gly Ser Ser Ala Ala Tyr His Val Gly
385                 390                 395                 400
Val Asn Tyr Glu Trp
                405

<210> SEQ ID NO 29
<211> LENGTH: 256
<212> TYPE: PRT
<213> ORGANISM: Haemophilus influenzae biogroup aegyptius

<400> SEQUENCE: 29

Met Lys Arg Asn Leu Leu Lys Gln Ser Val Ile Ala Val Leu Ile Gly
1               5                   10                  15
Gly Thr Thr Val Ser Asn Tyr Ala Leu Ala Gln Ala Gln Ala Gln Ala
                20                  25                  30
Gln Val Lys Lys Asp Glu Leu Ser Glu Leu Lys Lys Gln Val Lys Glu
            35                  40                  45
Met Asp Ala Ala Ile Asp Gly Ile Leu Asp Asp Asn Ile Ala Tyr Glu
        50                  55                  60
Ala Glu Val Asp Ala Lys Leu Asp Gln His Ser Ala Ala Leu Gly Arg
65                  70                  75                  80
His Thr Asn Arg Leu Asn Asn Leu Lys Thr Ile Ala Glu Lys Ala Lys
                85                  90                  95
Gly Asp Ser Ser Glu Ala Leu Asp Lys Ile Glu Ala Leu Glu Glu Gln
            100                 105                 110
Asn Asp Glu Phe Leu Ala Asp Ile Thr Ala Leu Glu Glu Gly Val Asp
            115                 120                 125
Gly Leu Asp Asp Asp Ile Thr Gly Ile Gln Asn Ile Ser Asp Ile
            130                 135                 140
Glu Asp Asp Ile Asn Gln Asn Ser Ala Asp Ile Ala Thr Asn Thr Ala
```

```
145                 150                 155                 160

Ala Ile Ala Thr His Thr Gln Arg Leu Asp Asn Leu Asp Asn Arg Val
                165                 170                 175

Asn Asn Leu Asn Lys Asp Leu Lys Arg Gly Leu Ala Ala Gln Ala Ala
            180                 185                 190

Leu Asn Gly Leu Phe Gln Pro Tyr Asn Val Gly Lys Leu Asn Leu Thr
        195                 200                 205

Ala Ala Val Gly Gly Tyr Lys Ser Gln Thr Ala Val Ala Val Gly Thr
    210                 215                 220

Gly Tyr Arg Tyr Asn Glu Asn Ile Ala Ala Lys Ala Gly Val Ala Phe
225                 230                 235                 240

Thr His Gly Gly Ser Ala Thr Tyr Asn Val Gly Val Asn Phe Glu Trp
                245                 250                 255

<210> SEQ ID NO 30
<211> LENGTH: 422
<212> TYPE: PRT
<213> ORGANISM: Yersinia enterocolitica
<400> SEQUENCE: 30

Met Thr Lys Asp Phe Lys Ile Ser Val Ser Ala Ala Leu Ile Ser Ala
1               5                   10                  15

Leu Phe Ser Ser Pro Tyr Ala Phe Ala Asn Asn Asp Glu Val His Phe
            20                  25                  30

Thr Ala Val Gln Ile Ser Pro Asn Ser Asp Pro Asp Ser His Val Met
        35                  40                  45

Ile Phe Gln Pro Glu Val Arg Ala Pro Gly Gly Thr Asn Ala Leu Ala
    50                  55                  60

Lys Gly Thr His Ser Ile Ala Val Gly Ala Ser Ala Glu Ala Ala Glu
65                  70                  75                  80

Arg Ala Ala Val Ala Val Gly Ala Gly Ser Ile Ala Thr Gly Val Asn
                85                  90                  95

Ser Val Ala Ile Gly Pro Leu Ser Lys Ala Leu Gly Asp Ser Ala Val
            100                 105                 110

Thr Tyr Gly Ala Gly Ser Thr Ala Gln Lys Asp Gly Val Ala Ile Gly
        115                 120                 125

Ala Arg Ala Ser Thr Ser Asp Thr Gly Val Ala Val Gly Phe Asn Ser
    130                 135                 140

Lys Val Asp Ala Lys Asn Ser Val Ser Ile Gly His Ser Ser His Val
145                 150                 155                 160

Ala Val Asp His Asp Tyr Ser Ile Ala Ile Gly Asp Arg Ser Lys Thr
                165                 170                 175

Asp Arg Lys Asn Ser Val Ser Ile Gly His Glu Ser Leu Asn Arg Gln
            180                 185                 190

Leu Thr His Leu Ala Ala Gly Thr Lys Asp Thr Asp Ala Val Asn Val
        195                 200                 205

Ala Gln Leu Lys Lys Glu Ile Glu Lys Thr Gln Glu Asn Ala Asn Lys
    210                 215                 220

Lys Ser Ala Glu Val Leu Gly Ile Ala Asn Asn Tyr Thr Asp Ser Lys
225                 230                 235                 240

Ser Ala Glu Thr Leu Glu Asn Ala Arg Lys Glu Ala Phe Asp Leu Ser
                245                 250                 255

Asn Asp Ala Leu Asp Met Ala Lys Lys His Ser Asn Ser Val Ala Arg
            260                 265                 270

Thr Thr Leu Glu Thr Ala Glu Glu His Thr Asn Lys Lys Ser Ala Glu
```

```
                275                 280                 285
Thr Leu Ala Ser Ala Asn Val Tyr Ala Asp Ser Lys Ser His Thr
290                 295                 300
Leu Lys Thr Ala Asn Ser Tyr Thr Asp Val Thr Val Ser Asn Ser Thr
305                 310                 315                 320
Lys Lys Ala Ile Arg Glu Ser Asn Gln Tyr Thr Asp His Lys Phe His
                325                 330                 335
Gln Leu Asp Asn Arg Leu Asp Lys Leu Asp Thr Arg Val Asp Lys Gly
                340                 345                 350
Leu Ala Ser Ser Ala Ala Leu Asn Ser Leu Phe Gln Pro Tyr Gly Val
                355                 360                 365
Gly Lys Val Asn Phe Thr Ala Gly Val Gly Gly Tyr Arg Ser Ser Gln
370                 375                 380
Ala Leu Ala Ile Gly Ser Gly Tyr Arg Val Asn Glu Ser Val Ala Leu
385                 390                 395                 400
Lys Ala Gly Val Ala Tyr Ala Gly Ser Ser Asp Val Met Tyr Asn Ala
                405                 410                 415
Ser Phe Asn Ile Glu Trp
                420

<210> SEQ ID NO 31
<211> LENGTH: 686
<212> TYPE: PRT
<213> ORGANISM: Moraxella catarrhalis

<400> SEQUENCE: 31

Met Lys Thr Met Lys Leu Leu Pro Leu Lys Ile Ala Val Thr Ser Ala
1               5                   10                  15
Met Ile Ile Gly Leu Gly Ala Ala Ser Thr Ala Asn Ala Gln Ala Thr
                20                  25                  30
Glu Thr Phe Leu Pro Asn Leu Phe Asp Asn Asp Tyr Thr Glu Thr Thr
                35                  40                  45
Asp Pro Leu Tyr His Gly Met Ile Leu Gly Asn Thr Ala Ile Thr Gln
            50                  55                  60
Asp Thr Gln Tyr Lys Phe Tyr Ala Glu Asn Gly Asn Glu Val Pro Asp
65                  70                  75                  80
Ser Leu Phe Phe Asn Lys Ile Leu His Asp Gln Gln Leu Asn Gly Phe
                85                  90                  95
Lys Glu Gly Asp Thr Ile Ile Pro Leu Asp Glu Asn Gly Lys Pro Val
                100                 105                 110
Tyr Lys Leu Asp Glu Ile Thr Glu Asn Gly Val Lys Arg Lys Val Tyr
                115                 120                 125
Ser Val Thr Thr Lys Thr Ala Thr Arg Glu Asp Val Glu Gln Ser Ala
            130                 135                 140
Tyr Ser Arg Gly Ile Gln Gly Asp Ile Asp Asp Leu Tyr Glu Ala Asn
145                 150                 155                 160
Lys Glu Asn Val Asn Arg Leu Ile Glu His Gly Asp Lys Ile Phe Ala
                165                 170                 175
Asn Glu Glu Ser Val Gln Tyr Leu Asn Lys Glu Val Gln Asn Asn Ile
                180                 185                 190
Glu Asn Ile His Glu Leu Ala Gln Gln Asp Gln His Ser Ser Asp
                195                 200                 205
Ile Lys Thr Leu Lys Lys Asn Val Glu Glu Gly Leu Leu Glu Leu Ser
            210                 215                 220
Gly Arg Leu Ile Ala Gln Lys Glu Asp Ile Ala Gln Asn Gln Thr Asp
```

-continued

```
                225                 230                 235                 240
Ile Gln Asp Leu Ala Thr Tyr Asn Glu Leu Gln Asp Gln Tyr Ala Gln
                245                 250                 255

Lys Gln Thr Glu Ala Ile Asp Ala Leu Asn Lys Ala Ser Ser Glu Asn
                260                 265                 270

Thr Gln Asn Ile Ala Lys Asn Ser Asn His Ile Lys Thr Leu Glu Asn
                275                 280                 285

Asn Ile Glu Glu Gly Leu Leu Glu Leu Ser Gly His Leu Ile Asp Gln
                290                 295                 300

Lys Ala Asp Leu Thr Lys Asp Ile Lys Ala Leu Glu Ser Asn Val Glu
305                 310                 315                 320

Glu Gly Leu Leu Asp Leu Ser Gly Arg Leu Leu Asp Gln Lys Ala Asp
                325                 330                 335

Ile Ala Lys Asn Gln Ala Asp Ile Ala Gln Asn Gln Thr Asp Ile Gln
                340                 345                 350

Asp Leu Ala Ala Tyr Asn Glu Leu Gln Asp Gln Tyr Ala Gln Lys Gln
                355                 360                 365

Thr Glu Ala Ile Asp Ala Leu Asn Lys Ala Ser Ser Glu Asn Thr Gln
                370                 375                 380

Asn Ile Glu Asp Leu Ala Ala Tyr Asn Glu Leu Gln Asp Ala Tyr Ala
385                 390                 395                 400

Lys Gln Gln Thr Glu Ala Ile Asp Ala Leu Asn Lys Ala Ser Ser Glu
                405                 410                 415

Asn Thr Gln Asn Ile Glu Asp Leu Ala Ala Tyr Asn Glu Leu Gln Asp
                420                 425                 430

Ala Tyr Ala Lys Gln Gln Thr Glu Ala Ile Asp Ala Leu Asn Lys Ala
                435                 440                 445

Ser Ser Glu Asn Thr Gln Asn Ile Ala Lys Asn Gln Ala Asp Ile Ala
450                 455                 460

Asn Asn Ile Asn Asn Ile Tyr Glu Leu Ala Gln Gln Gln Asp Gln His
465                 470                 475                 480

Ser Ser Asp Ile Lys Thr Leu Ala Lys Ala Ser Ala Ala Asn Thr Asp
                485                 490                 495

Arg Ile Ala Lys Asn Lys Ala Asp Ala Asp Ala Ser Phe Glu Thr Leu
                500                 505                 510

Thr Lys Asn Gln Asn Thr Leu Ile Glu Lys Asp Lys Glu His Asp Lys
                515                 520                 525

Leu Ile Thr Ala Asn Lys Thr Ala Ile Asp Ala Asn Lys Ala Ser Ala
                530                 535                 540

Asp Thr Lys Phe Ala Ala Thr Ala Asp Ala Ile Thr Lys Asn Gly Asn
545                 550                 555                 560

Ala Ile Thr Lys Asn Ala Lys Ser Ile Thr Asp Leu Gly Thr Lys Val
                565                 570                 575

Asp Gly Phe Asp Gly Arg Val Thr Ala Leu Asp Thr Lys Val Asn Ala
                580                 585                 590

Leu Asp Thr Lys Val Asn Ala Phe Asp Gly Arg Ile Thr Ala Leu Asp
                595                 600                 605

Ser Lys Val Glu Asn Gly Met Ala Ala Gln Ala Ala Leu Ser Gly Leu
                610                 615                 620

Phe Gln Pro Tyr Ser Val Gly Lys Phe Asn Ala Thr Ala Ala Leu Gly
625                 630                 635                 640

Gly Tyr Gly Ser Lys Ser Ala Val Ala Ile Gly Ala Gly Tyr Arg Val
                645                 650                 655
```

-continued

Asn Pro Asn Leu Ala Phe Lys Ala Gly Ala Ala Ile Asn Thr Ser Gly
            660                 665                 670

Asn Lys Lys Gly Ser Tyr Asn Ile Gly Val Asn Tyr Glu Phe
        675                 680                 685

<210> SEQ ID NO 32
<211> LENGTH: 824
<212> TYPE: PRT
<213> ORGANISM: Artificial Sequence
<220> FEATURE:
<223> OTHER INFORMATION: NadA-Env hybrid

<400> SEQUENCE: 32

Met Lys His Phe Pro Ser Lys Val Leu Thr Thr Ala Ile Leu Ala Thr
1               5                   10                  15

Phe Cys Ser Gly Ala Leu Ala Ala Ser Asn Asp Asp Ser Ala Val
            20                  25                  30

Glu Lys Leu Trp Val Thr Val Tyr Tyr Gly Val Pro Val Trp Lys Glu
        35                  40                  45

Ala Thr Thr Thr Leu Phe Cys Ala Ser Asp Ala Lys Ala Tyr Asp Thr
    50                  55                  60

Glu Val His Asn Val Trp Ala Thr His Ala Cys Val Pro Thr Asp Pro
65              70                  75                  80

Asn Pro Gln Glu Ile Val Leu Glu Asn Val Thr Glu Asn Phe Asn Met
                85                  90                  95

Trp Lys Asn Asn Met Val Glu Gln Met His Glu Asp Ile Ile Ser Leu
            100                 105                 110

Trp Asp Gln Ser Leu Lys Pro Cys Val Lys Leu Thr Pro Leu Cys Val
        115                 120                 125

Thr Leu His Cys Thr Asn Leu Lys Asn Ala Thr Asn Thr Lys Ser Ser
    130                 135                 140

Asn Trp Lys Glu Met Asp Arg Gly Glu Ile Lys Asn Cys Ser Phe Lys
145             150                 155                 160

Val Thr Thr Ser Ile Arg Asn Lys Met Gln Lys Glu Tyr Ala Leu Phe
                165                 170                 175

Tyr Lys Leu Asp Val Val Pro Ile Asp Asn Asp Asn Thr Ser Tyr Lys
            180                 185                 190

Leu Ile Asn Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asp Lys Lys Phe Asn Gly Ser Gly Pro Cys Thr
225             230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Gly Val Val Ile
            260                 265                 270

Arg Ser Glu Asn Phe Thr Asp Asn Ala Lys Thr Ile Ile Val Gln Leu
        275                 280                 285

Lys Glu Ser Val Glu Ile Asn Cys Thr Arg Pro Asn Asn Asn Thr Arg
    290                 295                 300

Lys Ser Ile Thr Ile Gly Pro Gly Arg Ala Phe Tyr Ala Thr Gly Asp
305             310                 315                 320

Ile Ile Gly Asp Ile Arg Gln Ala His Cys Asn Ile Ser Gly Glu Lys
                325                 330                 335

Trp Asn Asn Thr Leu Lys Gln Ile Val Thr Lys Leu Gln Ala Gln Phe

```
                340                 345                 350
Gly Asn Lys Thr Ile Val Phe Lys Gln Ser Ser Gly Gly Asp Pro Glu
            355                 360                 365

Ile Val Met His Ser Phe Asn Cys Gly Gly Glu Phe Phe Tyr Cys Asn
        370                 375                 380

Ser Thr Gln Leu Phe Asn Ser Thr Trp Asn Asn Thr Ile Gly Pro Asn
385                 390                 395                 400

Asn Thr Asn Gly Thr Ile Thr Leu Pro Cys Arg Ile Lys Gln Ile Ile
                405                 410                 415

Asn Arg Trp Gln Glu Val Gly Lys Ala Met Tyr Ala Pro Pro Ile Arg
            420                 425                 430

Gly Gln Ile Arg Cys Ser Ser Asn Ile Thr Gly Leu Leu Leu Thr Arg
        435                 440                 445

Asp Gly Gly Lys Glu Ile Ser Asn Thr Thr Glu Ile Phe Arg Pro Gly
    450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Lys Ala Lys Ser
                485                 490                 495

Ser Val Val Gln Ser Glu Lys Ser Gly Ser Lys Val Val Thr Asn Leu
            500                 505                 510

Thr Lys Thr Val Asn Glu Asn Lys Gln Asn Val Asp Ala Lys Val Lys
        515                 520                 525

Ala Ala Glu Ser Glu Ile Glu Lys Leu Thr Thr Lys Leu Ala Asp Thr
    530                 535                 540

Asp Ala Ala Leu Ala Asp Thr Asp Ala Ala Leu Asp Ala Thr Thr Asn
545                 550                 555                 560

Ala Leu Asn Lys Leu Gly Glu Asn Ile Thr Thr Phe Ala Glu Glu Thr
                565                 570                 575

Lys Thr Asn Ile Val Lys Ile Asp Glu Lys Leu Glu Ala Val Ala Asp
            580                 585                 590

Thr Val Asp Lys His Ala Glu Ala Phe Asn Asp Ile Ala Asp Ser Leu
        595                 600                 605

Asp Glu Thr Asn Thr Lys Ala Asp Glu Ala Val Lys Thr Ala Asn Glu
    610                 615                 620

Ala Lys Gln Thr Ala Glu Thr Lys Gln Asn Val Asp Ala Lys Val
625                 630                 635                 640

Lys Ala Ala Glu Thr Ala Ala Gly Lys Ala Glu Ala Ala Ala Gly Thr
                645                 650                 655

Ala Asn Thr Ala Ala Asp Lys Ala Glu Ala Val Ala Ala Lys Val Thr
            660                 665                 670

Asp Ile Lys Ala Asp Ile Ala Thr Asn Lys Asp Asn Ile Ala Lys Lys
        675                 680                 685

Ala Asn Ser Ala Asp Val Tyr Thr Arg Glu Glu Ser Asp Ser Lys Phe
    690                 695                 700

Val Arg Ile Asp Gly Leu Asn Ala Thr Thr Glu Lys Leu Asp Thr Arg
705                 710                 715                 720

Leu Ala Ser Ala Glu Lys Ser Ile Ala Asp His Asp Thr Arg Leu Asn
                725                 730                 735

Gly Leu Asp Lys Thr Val Ser Asp Leu Arg Lys Glu Thr Arg Gln Gly
            740                 745                 750

Leu Ala Glu Gln Ala Ala Leu Ser Gly Leu Phe Gln Pro Tyr Asn Val
        755                 760                 765
```

```
Gly Arg Phe Asn Val Thr Ala Ala Val Gly Tyr Lys Ser Glu Ser
            770                 775                 780

Ala Val Ala Ile Gly Thr Gly Phe Arg Phe Thr Glu Asn Phe Ala Ala
785                 790                 795                 800

Lys Ala Gly Val Ala Val Gly Thr Ser Ser Gly Ser Ser Ala Ala Tyr
                805                 810                 815

His Val Gly Val Asn Tyr Glu Trp
            820

<210> SEQ ID NO 33
<211> LENGTH: 837
<212> TYPE: PRT
<213> ORGANISM: Artificial Sequence
<220> FEATURE:
<223> OTHER INFORMATION: NadA-Env hybrid

<400> SEQUENCE: 33

Met Lys His Phe Pro Ser Lys Val Leu Thr Thr Ala Ile Leu Ala Thr
1               5                   10                  15

Phe Cys Ser Gly Ala Leu Ala Ala Ser Asn Asp Asp Ser Ala Val
            20                  25                  30

Glu Lys Leu Trp Val Thr Val Tyr Gly Val Pro Val Trp Lys Glu
            35                  40                  45

Ala Thr Thr Thr Leu Phe Cys Ala Ser Asp Ala Lys Ala Tyr Asp Thr
50                  55                  60

Glu Val His Asn Val Trp Ala Thr His Ala Cys Val Pro Thr Asp Pro
65                  70                  75                  80

Asn Pro Gln Glu Ile Val Leu Glu Asn Val Thr Glu Asn Phe Asn Met
                85                  90                  95

Trp Lys Asn Asn Met Val Glu Gln Met His Glu Asp Ile Ile Ser Leu
            100                 105                 110

Trp Asp Gln Ser Leu Lys Pro Cys Val Lys Leu Thr Pro Leu Cys Val
            115                 120                 125

Thr Leu His Cys Thr Asn Leu Lys Asn Ala Thr Asn Thr Lys Ser Ser
            130                 135                 140

Asn Trp Lys Glu Met Asp Arg Gly Glu Ile Lys Asn Cys Ser Phe Lys
145                 150                 155                 160

Val Thr Thr Ser Ile Arg Asn Lys Met Gln Lys Glu Tyr Ala Leu Phe
                165                 170                 175

Tyr Lys Leu Asp Val Val Pro Ile Asp Asn Asp Asn Thr Ser Tyr Lys
            180                 185                 190

Leu Ile Asn Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
    210                 215                 220

Ile Leu Lys Cys Asn Asp Lys Lys Phe Asn Gly Ser Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Gly Val Val Ile
            260                 265                 270

Arg Ser Glu Asn Phe Thr Asp Asn Ala Lys Thr Ile Ile Val Gln Leu
            275                 280                 285

Lys Glu Ser Val Glu Ile Asn Cys Thr Arg Pro Asn Asn Asn Thr Arg
    290                 295                 300

Lys Ser Ile Thr Ile Gly Pro Gly Arg Ala Phe Tyr Ala Thr Gly Asp
```

```
                305                 310                 315                 320

Ile Ile Gly Asp Ile Arg Gln Ala His Cys Asn Ile Ser Gly Glu Lys
                    325                 330                 335

Trp Asn Asn Thr Leu Lys Gln Ile Val Thr Lys Leu Gln Ala Gln Phe
                340                 345                 350

Gly Asn Lys Thr Ile Val Phe Lys Gln Ser Ser Gly Gly Asp Pro Glu
                355                 360                 365

Ile Val Met His Ser Phe Asn Cys Gly Gly Glu Phe Phe Tyr Cys Asn
370                 375                 380

Ser Thr Gln Leu Phe Asn Ser Thr Trp Asn Asn Thr Ile Gly Pro Asn
385                 390                 395                 400

Asn Thr Asn Gly Thr Ile Thr Leu Pro Cys Arg Ile Lys Gln Ile Ile
                    405                 410                 415

Asn Arg Trp Gln Glu Val Gly Lys Ala Met Tyr Ala Pro Pro Ile Arg
                420                 425                 430

Gly Gln Ile Arg Cys Ser Ser Asn Ile Thr Gly Leu Leu Leu Thr Arg
                435                 440                 445

Asp Gly Gly Lys Glu Ile Ser Asn Thr Thr Glu Ile Phe Arg Pro Gly
450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Lys Ala Ile Ser
                485                 490                 495

Ser Val Val Gln Ser Glu Lys Ser Gly Ser Lys Val Val Thr Asn Leu
                500                 505                 510

Thr Lys Thr Val Asn Glu Asn Lys Gln Asn Val Asp Ala Lys Val Lys
                515                 520                 525

Ala Ala Glu Ser Glu Ile Glu Lys Leu Thr Thr Lys Leu Ala Asp Thr
            530                 535                 540

Asp Ala Ala Leu Ala Asp Thr Asp Ala Ala Leu Asp Ala Thr Thr Asn
545                 550                 555                 560

Ala Leu Asn Lys Leu Gly Glu Asn Ile Thr Thr Phe Ala Glu Glu Thr
                565                 570                 575

Lys Thr Asn Ile Val Lys Ile Asp Glu Lys Leu Glu Ala Val Ala Asp
                580                 585                 590

Thr Val Asp Lys His Ala Glu Ala Phe Asn Asp Ile Ala Asp Ser Leu
            595                 600                 605

Asp Glu Thr Asn Thr Lys Ala Asp Glu Ala Val Lys Thr Ala Asn Glu
            610                 615                 620

Ala Lys Gln Thr Ala Glu Glu Thr Lys Gln Asn Val Asp Ala Lys Val
625                 630                 635                 640

Lys Ala Ala Glu Thr Ala Ala Gly Lys Ala Glu Ala Ala Ala Gly Thr
                645                 650                 655

Ala Asn Thr Ala Ala Asp Lys Ala Glu Ala Val Ala Ala Lys Val Thr
                660                 665                 670

Asp Ile Lys Ala Asp Ile Ala Thr Asn Lys Asp Asn Ile Ala Lys Lys
                675                 680                 685

Ala Asn Ser Ala Asp Val Tyr Thr Arg Glu Glu Ser Asp Ser Lys Phe
            690                 695                 700

Val Arg Ile Asp Gly Leu Asn Ala Thr Thr Glu Lys Leu Asp Thr Arg
705                 710                 715                 720

Leu Ala Ser Ala Glu Lys Ser Ile Ala Asp His Asp Thr Arg Lys Leu
                    725                 730                 735
```

```
Val Pro Arg Gly Ser Gly Gly Gly Gly Leu Asn Gly Leu Asp
            740             745             750

Lys Thr Val Ser Asp Leu Arg Lys Glu Thr Arg Gln Gly Leu Ala Glu
        755                 760                 765

Gln Ala Ala Leu Ser Gly Leu Phe Gln Pro Tyr Asn Val Gly Arg Phe
    770                 775                 780

Asn Val Thr Ala Ala Val Gly Gly Tyr Lys Ser Glu Ser Ala Val Ala
785                 790                 795                 800

Ile Gly Thr Gly Phe Arg Phe Thr Glu Asn Phe Ala Ala Lys Ala Gly
            805                 810                 815

Val Ala Val Gly Thr Ser Ser Gly Ser Ser Ala Ala Tyr His Val Gly
            820                 825                 830

Val Asn Tyr Glu Trp
            835

<210> SEQ ID NO 34
<211> LENGTH: 741
<212> TYPE: PRT
<213> ORGANISM: Artificial Sequence
<220> FEATURE:
<223> OTHER INFORMATION: NadA-Env hybrid

<400> SEQUENCE: 34

Met Lys His Phe Pro Ser Lys Val Leu Thr Thr Ala Ile Leu Ala Thr
1               5                   10                  15

Phe Cys Ser Gly Ala Leu Ala Ala Ser Asn Asp Asp Ser Ala Val
            20                  25                  30

Glu Lys Leu Trp Val Thr Val Tyr Tyr Gly Val Pro Val Trp Lys Glu
        35                  40                  45

Ala Thr Thr Thr Leu Phe Cys Ala Ser Asp Ala Lys Ala Tyr Asp Thr
    50                  55                  60

Glu Val His Asn Val Trp Ala Thr His Ala Cys Val Pro Thr Asp Pro
65                  70                  75                  80

Asn Pro Gln Glu Ile Val Leu Glu Asn Val Thr Glu Asn Phe Asn Met
            85                  90                  95

Trp Lys Asn Asn Met Val Glu Gln Met His Glu Asp Ile Ile Ser Leu
            100                 105                 110

Trp Asp Gln Ser Leu Lys Pro Cys Val Lys Leu Thr Pro Leu Cys Val
        115                 120                 125

Thr Leu His Cys Thr Asn Leu Lys Asn Ala Thr Asn Thr Lys Ser Ser
    130                 135                 140

Asn Trp Lys Glu Met Asp Arg Gly Glu Ile Lys Asn Cys Ser Phe Lys
145                 150                 155                 160

Val Thr Thr Ser Ile Arg Asn Lys Met Gln Lys Glu Tyr Ala Leu Phe
            165                 170                 175

Tyr Lys Leu Asp Val Val Pro Ile Asp Asn Asp Asn Thr Ser Tyr Lys
            180                 185                 190

Leu Ile Asn Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asp Lys Lys Phe Asn Gly Ser Gly Pro Cys Thr
225                 230                 235                 240

Asn Val Ser Thr Val Gln Cys Thr His Gly Ile Arg Pro Val Val Ser
            245                 250                 255

Thr Gln Leu Leu Leu Asn Gly Ser Leu Ala Glu Glu Gly Val Val Ile
```

-continued

```
            260                 265                 270
Arg Ser Glu Asn Phe Thr Asp Asn Ala Lys Thr Ile Ile Val Gln Leu
    275                 280                 285

Lys Glu Ser Val Glu Ile Asn Cys Thr Arg Pro Asn Asn Thr Arg
    290                 295                 300

Lys Ser Ile Thr Ile Gly Pro Gly Arg Ala Phe Tyr Ala Thr Gly Asp
305                 310                 315                 320

Ile Ile Gly Asp Ile Arg Gln Ala His Cys Asn Ile Ser Gly Glu Lys
                325                 330                 335

Trp Asn Asn Thr Leu Lys Gln Ile Val Thr Lys Leu Gln Ala Gln Phe
                340                 345                 350

Gly Asn Lys Thr Ile Val Phe Lys Gln Ser Ser Gly Gly Asp Pro Glu
                355                 360                 365

Ile Val Met His Ser Phe Asn Cys Gly Gly Glu Phe Phe Tyr Cys Asn
                370                 375                 380

Ser Thr Gln Leu Phe Asn Ser Thr Trp Asn Asn Thr Ile Gly Pro Asn
385                 390                 395                 400

Asn Thr Asn Gly Thr Ile Thr Leu Pro Cys Arg Ile Lys Gln Ile Ile
                405                 410                 415

Asn Arg Trp Gln Glu Val Gly Lys Ala Met Tyr Ala Pro Pro Ile Arg
                420                 425                 430

Gly Gln Ile Arg Cys Ser Ser Asn Ile Thr Gly Leu Leu Leu Thr Arg
                435                 440                 445

Asp Gly Gly Lys Glu Ile Ser Asn Thr Thr Glu Ile Phe Arg Pro Gly
                450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Lys Ala Leu Arg
                485                 490                 495

Thr Leu Gly Ala Met Phe Leu Gly Phe Leu Gly Ala Ala Gly Ser Thr
                500                 505                 510

Met Gly Ala Ala Ser Leu Thr Leu Thr Val Gln Ala Arg Gln Leu Leu
                515                 520                 525

Ser Gly Ile Val Gln Gln Asn Asn Leu Leu Arg Ala Ile Glu Ala
                530                 535                 540

Gln Gln His Leu Leu Gln Leu Thr Val Trp Gly Ile Lys Gln Leu Gln
545                 550                 555                 560

Ala Arg Val Leu Ala Val Glu Arg Tyr Leu Lys Asp Gln Gln Leu Leu
                565                 570                 575

Gly Ile Trp Gly Cys Ser Gly Lys Leu Ile Cys Thr Thr Ala Val Pro
                580                 585                 590

Trp Asn Ala Ser Trp Ser Asn Lys Ser Leu Asp Gln Ile Trp Asn Asn
                595                 600                 605

Met Thr Trp Met Glu Trp Glu Arg Glu Ile Asp Asn Tyr Thr Asn Leu
                610                 615                 620

Ile Tyr Thr Leu Ile Glu Glu Ser Gln Asn Gln Gln Glu Lys Asn Glu
625                 630                 635                 640

Gln Glu Leu Leu Glu Leu Asp Lys Trp Ala Ser Leu Trp Asn Trp Phe
                645                 650                 655

Asp Ile Ser Lys Trp Leu Trp Tyr Ile Lys Leu Gln Gly Leu Ala Glu
                660                 665                 670

Gln Ala Ala Leu Ser Gly Leu Phe Gln Pro Tyr Asn Val Gly Arg Phe
                675                 680                 685
```

-continued

```
Asn Val Thr Ala Ala Val Gly Gly Tyr Lys Ser Glu Ser Ala Val Ala
            690                 695                 700
Ile Gly Thr Gly Phe Arg Phe Thr Glu Asn Phe Ala Ala Lys Ala Gly
705                 710                 715                 720
Val Ala Val Gly Thr Ser Ser Gly Ser Ser Ala Ala Tyr His Val Gly
            725                 730                 735
Val Asn Tyr Glu Trp
            740

<210> SEQ ID NO 35
<211> LENGTH: 768
<212> TYPE: PRT
<213> ORGANISM: Artificial Sequence
<220> FEATURE:
<223> OTHER INFORMATION: NadA-Env hybrid

<400> SEQUENCE: 35

Met Lys His Phe Pro Ser Lys Val Leu Thr Thr Ala Ile Leu Ala Thr
1               5                   10                  15
Phe Cys Ser Gly Ala Leu Ala Ala Ser Asn Asp Asp Ser Ala Val
            20                  25                  30
Glu Lys Leu Trp Val Thr Val Tyr Gly Val Pro Val Trp Lys Glu
            35                  40                  45
Ala Thr Thr Thr Leu Phe Cys Ala Ser Asp Ala Lys Ala Tyr Asp Thr
50                  55                  60
Glu Val His Asn Val Trp Ala Thr His Ala Cys Val Pro Thr Asp Pro
65                  70                  75                  80
Asn Pro Gln Glu Ile Val Leu Glu Asn Val Thr Glu Asn Phe Asn Met
            85                  90                  95
Trp Lys Asn Asn Met Val Glu Gln Met His Glu Asp Ile Ile Ser Leu
            100                 105                 110
Trp Asp Gln Ser Leu Lys Pro Cys Val Lys Leu Thr Pro Leu Cys Val
            115                 120                 125
Thr Leu His Cys Thr Asn Leu Lys Asn Ala Thr Asn Thr Lys Ser Ser
            130                 135                 140
Asn Trp Lys Glu Met Asp Arg Gly Glu Ile Lys Asn Cys Ser Phe Lys
145                 150                 155                 160
Val Thr Thr Ser Ile Arg Asn Lys Met Gln Lys Glu Tyr Ala Leu Phe
                165                 170                 175
Tyr Lys Leu Asp Val Val Pro Ile Asp Asn Asp Asn Thr Ser Tyr Lys
            180                 185                 190
Leu Ile Asn Cys Asn Thr Ser Val Ile Thr Gln Ala Cys Pro Lys Val
            195                 200                 205
Ser Phe Glu Pro Ile Pro Ile His Tyr Cys Ala Pro Ala Gly Phe Ala
            210                 215                 220
Ile Leu Lys Cys Asn Asp Lys Lys Phe Asn Gly Ser Gly Pro Cys Thr
225                 230                 235                 240
Asn Val Ser Thr Val Gln Cys Thr His Gly Ile Arg Pro Val Val Ser
                245                 250                 255
Thr Gln Leu Leu Leu Asn Gly Ser Leu Ala Glu Glu Gly Val Val Ile
            260                 265                 270
Arg Ser Glu Asn Phe Thr Asp Asn Ala Lys Thr Ile Ile Val Gln Leu
            275                 280                 285
Lys Glu Ser Val Glu Ile Asn Cys Thr Arg Pro Asn Asn Asn Thr Arg
            290                 295                 300
Lys Ser Ile Thr Ile Gly Pro Gly Arg Ala Phe Tyr Ala Thr Gly Asp
```

```
                305                 310                 315                 320
        Ile Ile Gly Asp Ile Arg Gln Ala His Cys Asn Ile Ser Gly Glu Lys
                        325                 330                 335

Trp Asn Asn Thr Leu Lys Gln Ile Val Thr Lys Leu Gln Ala Gln Phe
                        340                 345                 350

Gly Asn Lys Thr Ile Val Phe Lys Gln Ser Ser Gly Gly Asp Pro Glu
                        355                 360                 365

Ile Val Met His Ser Phe Asn Cys Gly Gly Glu Phe Phe Tyr Cys Asn
        370                 375                 380

Ser Thr Gln Leu Phe Asn Ser Thr Trp Asn Asn Thr Ile Gly Pro Asn
        385                 390                 395                 400

Asn Thr Asn Gly Thr Ile Thr Leu Pro Cys Arg Ile Lys Gln Ile Ile
                        405                 410                 415

Asn Arg Trp Gln Glu Val Gly Lys Ala Met Tyr Ala Pro Pro Ile Arg
                        420                 425                 430

Gly Gln Ile Arg Cys Ser Ser Asn Ile Thr Gly Leu Leu Leu Thr Arg
                        435                 440                 445

Asp Gly Gly Lys Glu Ile Ser Asn Thr Thr Glu Ile Phe Arg Pro Gly
        450                 455                 460

Gly Gly Asp Met Arg Asp Asn Trp Arg Ser Glu Leu Tyr Lys Tyr Lys
        465                 470                 475                 480

Val Val Lys Ile Glu Pro Leu Gly Val Ala Pro Thr Lys Ala Leu Arg
                        485                 490                 495

Thr Leu Gly Ala Met Phe Leu Gly Phe Leu Gly Ala Ala Gly Ser Thr
                        500                 505                 510

Met Gly Ala Ala Ser Leu Thr Leu Thr Val Gln Ala Arg Gln Leu Leu
                        515                 520                 525

Ser Gly Ile Val Gln Gln Gln Asn Asn Leu Leu Arg Ala Ile Glu Ala
                        530                 535                 540

Gln Gln His Leu Leu Gln Leu Thr Val Trp Gly Ile Lys Gln Leu Gln
        545                 550                 555                 560

Ala Arg Val Leu Ala Val Glu Arg Tyr Leu Lys Asp Gln Gln Leu Leu
                        565                 570                 575

Gly Ile Trp Gly Cys Ser Gly Lys Leu Ile Cys Thr Thr Ala Val Pro
                        580                 585                 590

Trp Asn Ala Ser Trp Ser Asn Lys Ser Leu Asp Gln Ile Trp Asn Asn
                        595                 600                 605

Met Thr Trp Met Glu Trp Glu Arg Glu Ile Asp Asn Tyr Thr Asn Leu
                        610                 615                 620

Ile Tyr Thr Leu Ile Glu Glu Ser Gln Asn Gln Gln Glu Lys Asn Glu
        625                 630                 635                 640

Gln Glu Leu Leu Glu Leu Asp Lys Trp Ala Ser Leu Trp Asn Trp Phe
                        645                 650                 655

Asp Ile Ser Lys Trp Leu Trp Tyr Ile Lys Leu Val Pro Arg Gly Ser
                        660                 665                 670

Gly Gly Gly Gly Gly Gly Leu Asn Gly Leu Asp Lys Thr Val Ser Asp
                        675                 680                 685

Leu Arg Lys Glu Thr Arg Gln Gly Leu Ala Glu Gln Ala Ala Leu Ser
                        690                 695                 700

Gly Leu Phe Gln Pro Tyr Asn Val Gly Arg Phe Asn Val Thr Ala Ala
        705                 710                 715                 720

Val Gly Gly Tyr Lys Ser Glu Ser Ala Val Ala Ile Gly Thr Gly Phe
                        725                 730                 735
```

```
Arg Phe Thr Glu Asn Phe Ala Ala Lys Ala Gly Val Ala Val Gly Thr
                740                 745                 750

Ser Ser Gly Ser Ser Ala Ala Tyr His Val Gly Val Asn Tyr Glu Trp
        755                 760                 765

<210> SEQ ID NO 36
<211> LENGTH: 475
<212> TYPE: PRT
<213> ORGANISM: Human immunodeficiency virus

<400> SEQUENCE: 36

Ser Ala Val Glu Lys Leu Trp Val Thr Val Tyr Tyr Gly Val Pro Val
1               5                   10                  15

Trp Lys Glu Ala Thr Thr Thr Leu Phe Cys Ala Ser Asp Ala Lys Ala
                20                  25                  30

Tyr Asp Thr Glu Val His Asn Val Trp Ala Thr His Ala Cys Val Pro
            35                  40                  45

Thr Asp Pro Asn Pro Gln Glu Ile Val Leu Glu Asn Val Thr Glu Asn
        50                  55                  60

Phe Asn Met Trp Lys Asn Asn Met Val Glu Gln Met His Glu Asp Ile
65                  70                  75                  80

Ile Ser Leu Trp Asp Gln Ser Leu Lys Pro Cys Val Lys Leu Thr Pro
                85                  90                  95

Leu Cys Val Thr Leu His Cys Thr Asn Leu Lys Asn Ala Thr Asn Thr
            100                 105                 110

Lys Ser Ser Asn Trp Lys Glu Met Asp Arg Gly Glu Ile Lys Asn Cys
        115                 120                 125

Ser Phe Lys Val Thr Thr Ser Ile Arg Asn Lys Met Gln Lys Glu Tyr
130                 135                 140

Ala Leu Phe Tyr Lys Leu Asp Val Val Pro Ile Asp Asn Asp Asn Thr
145                 150                 155                 160

Ser Tyr Lys Leu Ile Asn Cys Asn Thr Ser Val Ile Thr Gln Ala Cys
                165                 170                 175

Pro Lys Val Ser Phe Glu Pro Ile Pro Ile His Tyr Cys Ala Pro Ala
            180                 185                 190

Gly Phe Ala Ile Leu Lys Cys Asn Asp Lys Lys Phe Asn Gly Ser Gly
        195                 200                 205

Pro Cys Thr Asn Val Ser Thr Val Gln Cys Thr His Gly Ile Arg Pro
210                 215                 220

Val Val Ser Thr Gln Leu Leu Leu Asn Gly Ser Leu Ala Glu Glu Gly
225                 230                 235                 240

Val Val Ile Arg Ser Glu Asn Phe Thr Asp Asn Ala Lys Thr Ile Ile
                245                 250                 255

Val Gln Leu Lys Glu Ser Val Glu Ile Asn Cys Thr Arg Pro Asn Asn
            260                 265                 270

Asn Thr Arg Lys Ser Ile Thr Ile Gly Pro Gly Arg Ala Phe Tyr Ala
        275                 280                 285

Thr Gly Asp Ile Ile Gly Asp Ile Arg Gln Ala His Cys Asn Ile Ser
290                 295                 300

Gly Glu Lys Trp Asn Asn Thr Leu Lys Gln Ile Val Thr Lys Leu Gln
305                 310                 315                 320

Ala Gln Phe Gly Asn Lys Thr Ile Val Phe Lys Gln Ser Ser Gly Gly
                325                 330                 335

Asp Pro Glu Ile Val Met His Ser Phe Asn Cys Gly Gly Glu Phe Phe
            340                 345                 350
```

```
Tyr Cys Asn Ser Thr Gln Leu Phe Asn Ser Thr Trp Asn Asn Thr Ile
        355                 360                 365

Gly Pro Asn Asn Thr Asn Gly Thr Ile Thr Leu Pro Cys Arg Ile Lys
    370                 375                 380

Gln Ile Ile Asn Arg Trp Gln Glu Val Gly Lys Ala Met Tyr Ala Pro
385                 390                 395                 400

Pro Ile Arg Gly Gln Ile Arg Cys Ser Ser Asn Ile Thr Gly Leu Leu
            405                 410                 415

Leu Thr Arg Asp Gly Gly Lys Glu Ile Ser Asn Thr Thr Glu Ile Phe
        420                 425                 430

Arg Pro Gly Gly Gly Asp Met Arg Asp Asn Trp Arg Ser Glu Leu Tyr
        435                 440                 445

Lys Tyr Lys Val Val Lys Ile Glu Pro Leu Gly Val Ala Pro Thr Lys
    450                 455                 460

Ala Lys Ser Ser Val Val Gln Ser Glu Lys Ser
465                 470                 475

<210> SEQ ID NO 37
<211> LENGTH: 13
<212> TYPE: PRT
<213> ORGANISM: Artificial Sequence
<220> FEATURE:
<223> OTHER INFORMATION: Thrombin recognition sequence

<400> SEQUENCE: 37

Lys Leu Val Pro Arg Gly Ser Gly Gly Gly Gly Gly Gly
1               5                   10

<210> SEQ ID NO 38
<211> LENGTH: 6
<212> TYPE: PRT
<213> ORGANISM: Thrombin recognition sequence

<400> SEQUENCE: 38

Leu Val Pro Arg Gly Ser
1               5

<210> SEQ ID NO 39
<211> LENGTH: 636
<212> TYPE: PRT
<213> ORGANISM: Human immunodeficiency virus

<400> SEQUENCE: 39

Ser Ala Val Glu Lys Leu Trp Val Thr Val Tyr Tyr Gly Val Pro Val
1               5                   10                  15

Trp Lys Glu Ala Thr Thr Thr Leu Phe Cys Ala Ser Asp Ala Lys Ala
            20                  25                  30

Tyr Asp Thr Glu Val His Asn Val Trp Ala Thr His Ala Cys Val Pro
        35                  40                  45

Thr Asp Pro Asn Pro Gln Glu Ile Val Leu Glu Asn Val Thr Glu Asn
    50                  55                  60

Phe Asn Met Trp Lys Asn Asn Met Val Glu Gln Met His Glu Asp Ile
65                  70                  75                  80

Ile Ser Leu Trp Asp Gln Ser Leu Lys Pro Cys Val Lys Leu Thr Pro
                85                  90                  95

Leu Cys Val Thr Leu His Cys Thr Asn Leu Lys Asn Ala Thr Asn Thr
            100                 105                 110

Lys Ser Ser Asn Trp Lys Glu Met Asp Arg Gly Glu Ile Lys Asn Cys
        115                 120                 125
```

```
Ser Phe Lys Val Thr Thr Ser Ile Arg Asn Lys Met Gln Lys Glu Tyr
130                 135                 140

Ala Leu Phe Tyr Lys Leu Asp Val Val Pro Ile Asp Asn Asp Asn Thr
145                 150                 155                 160

Ser Tyr Lys Leu Ile Asn Cys Asn Thr Ser Val Ile Thr Gln Ala Cys
                165                 170                 175

Pro Lys Val Ser Phe Glu Pro Ile Pro Ile His Tyr Cys Ala Pro Ala
            180                 185                 190

Gly Phe Ala Ile Leu Lys Cys Asn Asp Lys Lys Phe Asn Gly Ser Gly
        195                 200                 205

Pro Cys Thr Asn Val Ser Thr Val Gln Cys Thr His Gly Ile Arg Pro
210                 215                 220

Val Val Ser Thr Gln Leu Leu Leu Asn Gly Ser Leu Ala Glu Glu Gly
225                 230                 235                 240

Val Val Ile Arg Ser Glu Asn Phe Thr Asp Asn Ala Lys Thr Ile Ile
                245                 250                 255

Val Gln Leu Lys Glu Ser Val Glu Ile Asn Cys Thr Arg Pro Asn Asn
            260                 265                 270

Asn Thr Arg Lys Ser Ile Thr Ile Gly Pro Gly Arg Ala Phe Tyr Ala
        275                 280                 285

Thr Gly Asp Ile Ile Gly Asp Ile Arg Gln Ala His Cys Asn Ile Ser
290                 295                 300

Gly Glu Lys Trp Asn Asn Thr Leu Lys Gln Ile Val Thr Lys Leu Gln
305                 310                 315                 320

Ala Gln Phe Gly Asn Lys Thr Ile Val Phe Lys Gln Ser Ser Gly Gly
                325                 330                 335

Asp Pro Glu Ile Val Met His Ser Phe Asn Cys Gly Gly Glu Phe Phe
            340                 345                 350

Tyr Cys Asn Ser Thr Gln Leu Phe Asn Ser Thr Trp Asn Asn Thr Ile
        355                 360                 365

Gly Pro Asn Asn Thr Asn Gly Thr Ile Thr Leu Pro Cys Arg Ile Lys
370                 375                 380

Gln Ile Ile Asn Arg Trp Gln Glu Val Gly Lys Ala Met Tyr Ala Pro
385                 390                 395                 400

Pro Ile Arg Gly Gln Ile Arg Cys Ser Ser Asn Ile Thr Gly Leu Leu
                405                 410                 415

Leu Thr Arg Asp Gly Gly Lys Glu Ile Ser Asn Thr Thr Glu Ile Phe
            420                 425                 430

Arg Pro Gly Gly Gly Asp Met Arg Asp Asn Trp Arg Ser Glu Leu Tyr
        435                 440                 445

Lys Tyr Lys Val Val Lys Ile Glu Pro Leu Gly Val Ala Pro Thr Lys
450                 455                 460

Ala Leu Arg Thr Leu Gly Ala Met Phe Leu Gly Phe Leu Gly Ala Ala
465                 470                 475                 480

Gly Ser Thr Met Gly Ala Ala Ser Leu Thr Leu Thr Val Gln Ala Arg
                485                 490                 495

Gln Leu Leu Ser Gly Ile Val Gln Gln Asn Asn Leu Leu Arg Ala
            500                 505                 510

Ile Glu Ala Gln Gln His Leu Leu Gln Leu Thr Val Trp Gly Ile Lys
        515                 520                 525

Gln Leu Gln Ala Arg Val Leu Ala Val Glu Arg Tyr Leu Lys Asp Gln
530                 535                 540

Gln Leu Leu Gly Ile Trp Gly Cys Ser Gly Lys Leu Ile Cys Thr Thr
545                 550                 555                 560
```

```
Ala Val Pro Trp Asn Ala Ser Trp Ser Asn Lys Ser Leu Asp Gln Ile
            565                 570                 575

Trp Asn Asn Met Thr Trp Met Glu Trp Glu Arg Glu Ile Asp Asn Tyr
            580                 585                 590

Thr Asn Leu Ile Tyr Thr Leu Ile Glu Glu Ser Gln Asn Gln Gln Glu
            595                 600                 605

Lys Asn Glu Gln Glu Leu Leu Glu Leu Asp Lys Trp Ala Ser Leu Trp
            610                 615                 620

Asn Trp Phe Asp Ile Ser Lys Trp Leu Trp Tyr Ile
625                 630                 635

<210> SEQ ID NO 40
<211> LENGTH: 90
<212> TYPE: PRT
<213> ORGANISM: Neisseria meningitidis

<400> SEQUENCE: 40

Leu Asn Gly Leu Asp Lys Thr Val Ser Asp Leu Arg Lys Glu Thr Arg
1               5                   10                  15

Gln Gly Leu Ala Glu Gln Ala Ala Leu Ser Gly Leu Phe Gln Pro Tyr
            20                  25                  30

Asn Val Gly Arg Phe Asn Val Thr Ala Ala Val Gly Gly Tyr Lys Ser
        35                  40                  45

Glu Ser Ala Val Ala Ile Gly Thr Gly Phe Arg Phe Thr Glu Asn Phe
    50                  55                  60

Ala Ala Lys Ala Gly Val Ala Val Gly Thr Ser Ser Gly Ser Ser Ala
65                  70                  75                  80

Ala Tyr His Val Gly Val Asn Tyr Glu Trp
85                  90

<210> SEQ ID NO 41
<211> LENGTH: 318
<212> TYPE: PRT
<213> ORGANISM: Neisseria meningitidis

<400> SEQUENCE: 41

Lys Val Val Thr Asn Leu Thr Lys Thr Val Asn Glu Asn Lys Gln Asn
1               5                   10                  15

Val Asp Ala Lys Val Lys Ala Ala Glu Ser Glu Ile Glu Lys Leu Thr
            20                  25                  30

Thr Lys Leu Ala Asp Thr Asp Ala Ala Leu Ala Asp Thr Asp Ala Ala
        35                  40                  45

Leu Asp Ala Thr Thr Asn Ala Leu Asn Lys Leu Gly Glu Asn Ile Thr
    50                  55                  60

Thr Phe Ala Glu Glu Thr Lys Thr Asn Ile Val Lys Ile Asp Glu Lys
65                  70                  75                  80

Leu Glu Ala Val Ala Asp Thr Val Asp Lys His Ala Glu Ala Phe Asn
            85                  90                  95

Asp Ile Ala Asp Ser Leu Asp Glu Thr Asn Thr Lys Ala Asp Glu Ala
            100                 105                 110

Val Lys Thr Ala Asn Glu Ala Lys Gln Thr Ala Glu Glu Thr Lys Gln
        115                 120                 125

Asn Val Asp Ala Lys Val Lys Ala Ala Glu Thr Ala Ala Gly Lys Ala
    130                 135                 140

Glu Ala Ala Ala Gly Thr Ala Asn Thr Ala Ala Asp Lys Ala Glu Ala
145                 150                 155                 160
```

-continued

```
Val Ala Ala Lys Val Thr Asp Ile Lys Ala Asp Ile Ala Thr Asn Lys
            165                 170                 175

Asp Asn Ile Ala Lys Lys Ala Asn Ser Ala Asp Val Tyr Thr Arg Glu
        180                 185                 190

Glu Ser Asp Ser Lys Phe Val Arg Ile Asp Gly Leu Asn Ala Thr Thr
    195                 200                 205

Glu Lys Leu Asp Thr Arg Leu Ala Ser Ala Glu Lys Ser Ile Ala Asp
210                 215                 220

His Asp Thr Arg Leu Asn Gly Leu Asp Lys Thr Val Ser Asp Leu Arg
225                 230                 235                 240

Lys Glu Thr Arg Gln Gly Leu Ala Glu Gln Ala Ala Leu Ser Gly Leu
                245                 250                 255

Phe Gln Pro Tyr Asn Val Gly Arg Phe Asn Val Thr Ala Ala Val Gly
            260                 265                 270

Gly Tyr Lys Ser Glu Ser Ala Val Ala Ile Gly Thr Gly Phe Arg Phe
        275                 280                 285

Thr Glu Asn Phe Ala Ala Lys Ala Gly Val Ala Val Gly Thr Ser Ser
    290                 295                 300

Gly Ser Ser Ala Ala Tyr His Val Gly Val Asn Tyr Glu Trp
305                 310                 315

<210> SEQ ID NO 42
<211> LENGTH: 338
<212> TYPE: PRT
<213> ORGANISM: Escherichia coli

<400> SEQUENCE: 42

Met Lys Thr Val Asn Val Ala Leu Leu Ala Leu Ile Ile Ser Ala Thr
1               5                   10                  15

Ser Ser Pro Val Val Leu Ala Gly Asp Thr Ile Glu Ala Ala Ala Thr
            20                  25                  30

Glu Leu Ser Ala Ile Asn Ser Gly Met Ser Gln Ser Glu Ile Glu Gln
        35                  40                  45

Lys Ile Thr Arg Phe Leu Glu Arg Thr Asp Asn Ser Pro Ala Ala Tyr
    50                  55                  60

Thr Tyr Leu Thr Glu His His Tyr Ile Pro Ser Glu Thr Pro Asp Thr
65                  70                  75                  80

Thr Gln Thr Pro Thr Val Gln Thr Asp Pro Asp Ala Gly Gln Lys Thr
                85                  90                  95

Val Ala Ala Thr Gly Asp Val Leu Thr Thr Ala Arg Tyr Gln Ser Met
            100                 105                 110

Ile Asn Ala Arg Gln Ser Ala Val Thr Asp Ala Gln Gln Thr Gln Ile
        115                 120                 125

Thr Glu Gln Gln Ala Gln Ile Val Ala Thr Gln Lys Thr Leu Ala Ala
    130                 135                 140

Thr Gly Asp Thr Gln Asn Thr Ala His Tyr Gln Glu Met Ile Asn Ala
145                 150                 155                 160

Arg Leu Ala Ala Gln Asn Glu Ala Asn Gln Arg Thr Ala Thr Glu Gln
                165                 170                 175

Gly Gln Lys Met Asn Ala Leu Thr Thr Asp Val Ala Val Gln Gln Gln
            180                 185                 190

Asn Glu Arg Thr Gln Tyr Asp Lys Gln Met Gln Ser Leu Ala Gln Glu
        195                 200                 205

Ser Ala Gln Ala His Glu Gln Ile Asp Ser Leu Ser Gln Asp Val Thr
    210                 215                 220
```

```
Gln Thr His Gln Gln Leu Thr Asn Thr Gln Lys Arg Val Ala Asp Asn
225                 230                 235                 240

Ser Gln Gln Ile Asn Thr Leu Asn Asn His Phe Ser Ser Leu Lys Asn
            245                 250                 255

Glu Val Asp Asp Asn Arg Lys Glu Ala Asn Ala Gly Thr Ala Ser Ala
        260                 265                 270

Ile Ala Ile Ala Ser Gln Pro Gln Val Lys Thr Gly Asp Val Met Met
        275                 280                 285

Val Ser Ala Gly Ala Gly Thr Phe Asn Gly Glu Ser Ala Val Ser Val
        290                 295                 300

Gly Thr Ser Phe Asn Ala Gly Thr His Thr Val Leu Lys Ala Gly Ile
305                 310                 315                 320

Ser Ala Asp Thr Gln Ser Asp Phe Gly Ala Gly Val Gly Val Gly Tyr
            325                 330                 335

Ser Phe

<210> SEQ ID NO 43
<211> LENGTH: 1588
<212> TYPE: PRT
<213> ORGANISM: Escherichia coli

<400> SEQUENCE: 43

Met Asn Lys Ile Phe Lys Val Ile Trp Asn Pro Ala Thr Gly Asn Tyr
1               5                   10                  15

Thr Val Thr Ser Glu Thr Ala Lys Ser Arg Gly Lys Lys Ser Gly Arg
            20                  25                  30

Ser Lys Leu Leu Ile Ser Ala Leu Val Ala Gly Gly Met Leu Ser Ser
        35                  40                  45

Phe Gly Ala Leu Ala Asn Ala Gly Asn Asp Asn Gly Gln Gly Val Asp
    50                  55                  60

Tyr Gly Ser Gly Ser Ala Gly Asp Gly Trp Val Ala Ile Gly Lys Gly
65              70                  75                  80

Ala Lys Ala Asn Thr Phe Met Asn Thr Ser Gly Ser Ser Thr Ala Val
                85                  90                  95

Gly Tyr Asp Ala Ile Ala Glu Gly Gln Tyr Ser Ser Ala Ile Gly Ser
            100                 105                 110

Lys Thr His Ala Ile Gly Gly Ala Ser Met Ala Phe Gly Val Ser Ala
        115                 120                 125

Ile Ser Glu Gly Asp Arg Ser Ile Ala Leu Gly Ala Ser Ser Tyr Ser
    130                 135                 140

Leu Gly Gln Tyr Ser Met Ala Leu Gly Arg Tyr Ser Lys Ala Leu Gly
145                 150                 155                 160

Lys Leu Ser Ile Ala Met Gly Asp Ser Ser Lys Ala Glu Gly Ala Asn
                165                 170                 175

Ala Ile Ala Leu Gly Asn Ala Thr Lys Ala Thr Glu Ile Met Ser Ile
            180                 185                 190

Ala Leu Gly Asp Thr Ala Asn Ala Ser Lys Ala Tyr Ser Met Ala Leu
        195                 200                 205

Gly Ala Ser Ser Val Ala Ser Glu Glu Asn Ala Ile Ala Ile Gly Ala
    210                 215                 220

Glu Thr Glu Ala Ala Glu Asn Ala Thr Ala Ile Gly Asn Asn Ala Lys
225                 230                 235                 240

Ala Lys Gly Thr Asn Ser Met Ala Met Gly Phe Gly Ser Leu Ala Asp
                245                 250                 255

Lys Val Asn Thr Ile Ala Leu Gly Asn Gly Ser Gln Ala Leu Ala Asp
```

-continued

```
                260                 265                 270
Asn Ala Ile Ala Ile Gly Gln Gly Asn Lys Ala Asp Gly Val Asp Ala
            275                 280                 285
Ile Ala Leu Gly Asn Gly Ser Gln Ser Arg Gly Leu Asn Thr Ile Ala
            290                 295                 300
Leu Gly Thr Ala Ser Asn Ala Thr Gly Asp Lys Ser Leu Ala Leu Gly
305                 310                 315                 320
Ser Asn Ser Ser Ala Asn Gly Ile Asn Ser Val Ala Leu Gly Ala Asp
            325                 330                 335
Ser Ile Ala Asp Leu Asp Asn Thr Val Ser Val Gly Asn Ser Ser Leu
            340                 345                 350
Lys Arg Lys Ile Val Asn Val Lys Asn Gly Ala Ile Lys Ser Asp Ser
            355                 360                 365
Tyr Asp Ala Ile Asn Gly Ser Gln Leu Tyr Ala Ile Ser Asp Ser Val
            370                 375                 380
Ala Lys Arg Leu Gly Gly Gly Ala Ala Val Asp Val Asp Gly Thr
385                 390                 395                 400
Val Thr Ala Pro Thr Tyr Asn Leu Lys Asn Gly Ser Lys Asn Asn Val
            405                 410                 415
Gly Ala Ala Leu Ala Val Leu Asp Glu Asn Thr Leu Gln Trp Asp Gln
            420                 425                 430
Thr Lys Gly Lys Tyr Ser Ala Ala His Gly Thr Ser Ser Pro Thr Ala
            435                 440                 445
Ser Val Ile Thr Asp Val Ala Asp Gly Thr Ile Ser Ala Ser Ser Lys
            450                 455                 460
Asp Ala Val Asn Gly Ser Gln Leu Lys Ala Thr Asn Asp Asp Val Glu
465                 470                 475                 480
Ala Asn Thr Ala Asn Ile Ala Thr Asn Thr Asn Ile Ala Thr Asn
            485                 490                 495
Thr Ala Asn Ile Ala Thr Asn Thr Thr Asn Ile Thr Asn Leu Thr Asp
            500                 505                 510
Ser Val Gly Asp Leu Gln Ala Asp Ala Leu Leu Trp Asn Glu Thr Lys
            515                 520                 525
Lys Ala Phe Ser Ala Ala His Gly Gln Asp Thr Thr Ser Lys Ile Thr
            530                 535                 540
Asn Val Lys Asp Ala Asp Leu Thr Ala Asp Ser Thr Asp Ala Val Asn
545                 550                 555                 560
Gly Ser Gln Leu Lys Thr Thr Asn Asp Ala Val Ala Thr Asn Thr Thr
            565                 570                 575
Asn Ile Ala Asn Asn Thr Ser Asn Ile Ala Thr Asn Thr Asn Ile
            580                 585                 590
Ser Asn Leu Thr Glu Thr Val Thr Asn Leu Gly Glu Asp Ala Leu Lys
            595                 600                 605
Trp Asp Lys Asp Asn Gly Val Phe Thr Ala Ala His Gly Thr Glu Thr
            610                 615                 620
Thr Ser Lys Ile Thr Asn Val Lys Asp Gly Asp Leu Thr Thr Gly Ser
625                 630                 635                 640
Thr Asp Ala Val Asn Gly Ser Gln Leu Lys Thr Thr Asn Asp Ala Val
            645                 650                 655
Ala Thr Asn Thr Thr Asn Ile Ala Thr Asn Thr Thr Asn Ile Ser Asn
            660                 665                 670
Leu Thr Glu Thr Val Thr Asn Leu Gly Glu Asp Ala Leu Lys Trp Asp
            675                 680                 685
```

```
Lys Asp Asn Gly Val Phe Thr Ala Ala His Gly Asn Asn Thr Ala Ser
690                 695                 700

Lys Ile Thr Asn Ile Leu Asp Gly Thr Val Thr Ala Thr Ser Ser Asp
705                 710                 715                 720

Ala Ile Asn Gly Ser Gln Leu Tyr Asp Leu Ser Ser Asn Ile Ala Thr
                725                 730                 735

Tyr Phe Gly Gly Asn Ala Ser Val Asn Thr Asp Gly Val Phe Thr Gly
            740                 745                 750

Pro Tyr Lys Ile Gly Glu Thr Asn Tyr Tyr Asn Val Gly Asp Ala
        755                 760                 765

Leu Ala Ala Ile Asn Ser Ser Phe Ser Thr Ser Leu Gly Asp Ala Leu
770                 775                 780

Leu Trp Asp Ala Thr Ala Gly Lys Phe Ser Ala Lys His Gly Thr Asn
785                 790                 795                 800

Gly Asp Ala Ser Val Ile Thr Asp Val Ala Asp Gly Glu Ile Ser Asp
                805                 810                 815

Ser Ser Ser Asp Ala Val Asn Gly Ser Gln Leu His Gly Val Ser Ser
                820                 825                 830

Tyr Val Val Asp Ala Leu Gly Gly Ala Glu Val Asn Ala Asp Gly
            835                 840                 845

Thr Ile Thr Ala Pro Thr Tyr Thr Ile Ala Asn Ala Asp Tyr Asp Asn
850                 855                 860

Val Gly Asp Ala Leu Asn Ala Ile Asp Thr Thr Leu Asp Asp Ala Leu
865                 870                 875                 880

Leu Trp Asp Ala Asp Ala Gly Glu Asn Gly Ala Phe Ser Ala Ala His
                885                 890                 895

Gly Lys Asp Lys Thr Ala Ser Val Ile Thr Asn Val Ala Asn Gly Ala
            900                 905                 910

Ile Ser Ala Ala Ser Ser Asp Ala Ile Asn Gly Ser Gln Leu Tyr Thr
                915                 920                 925

Thr Asn Lys Tyr Ile Ala Asp Ala Leu Gly Gly Asp Ala Glu Val Asn
930                 935                 940

Ala Asp Gly Thr Ile Thr Ala Pro Thr Tyr Thr Ile Ala Asn Ala Glu
945                 950                 955                 960

Tyr Asn Asn Val Gly Asp Ala Leu Asp Ala Leu Asp Asn Ala Leu
            965                 970                 975

Leu Trp Asp Glu Thr Ala Asn Gly Gly Ala Gly Ala Tyr Asn Ala Ser
                980                 985                 990

His Asp Gly Lys Ala Ser Ile Ile Thr Asn Val Ala Asn Gly Ser Ile
            995                 1000                1005

Ser Glu Asp Ser Thr Asp Ala Val Asn Gly Ser Gln Leu Asn Ala Thr
        1010                1015                1020

Asn Met Met Ile Glu Gln Asn Thr Gln Ile Ile Asn Gln Leu Ala Gly
1025                1030                1035                1040

Asn Thr Asp Ala Thr Tyr Ile Gln Glu Asn Gly Ala Gly Ile Asn Tyr
                1045                1050                1055

Val Arg Thr Asn Asp Asp Gly Leu Ala Phe Asn Asp Ala Ser Ala Gln
            1060                1065                1070

Gly Val Gly Ala Thr Ala Ile Gly Tyr Asn Ser Val Ala Lys Gly Asp
            1075                1080                1085

Ser Ser Val Ala Ile Gly Gln Gly Ser Tyr Ser Asp Val Asp Thr Gly
        1090                1095                1100

Ile Ala Leu Gly Ser Ser Ser Val Ser Ser Arg Val Ile Ala Lys Gly
1105                1110                1115                1120
```

```
Ser Arg Asp Thr Ser Ile Thr Glu Asn Gly Val Ile Gly Tyr Asp
            1125                1130                1135

Thr Thr Asp Gly Glu Leu Leu Gly Ala Leu Ser Ile Gly Asp Asp Gly
            1140                1145                1150

Lys Tyr Arg Gln Ile Ile Asn Val Ala Asp Gly Ser Glu Ala His Asp
            1155                1160                1165

Ala Val Thr Val Arg Gln Leu Gln Asn Ala Ile Gly Ala Val Ala Thr
            1170                1175                1180

Thr Pro Thr Lys Tyr Phe His Ala Asn Ser Thr Glu Glu Asp Ser Leu
1185                1190                1195                1200

Ala Val Gly Thr Asp Ser Leu Ala Met Gly Ala Lys Thr Ile Val Asn
            1205                1210                1215

Gly Asp Lys Gly Ile Gly Ile Gly Tyr Gly Ala Tyr Val Asp Ala Asn
            1220                1225                1230

Ala Leu Asn Gly Ile Ala Ile Gly Ser Asn Ala Gln Val Ile His Val
            1235                1240                1245

Asn Ser Ile Ala Ile Gly Asn Gly Ser Thr Thr Thr Arg Gly Ala Gln
            1250                1255                1260

Thr Asn Tyr Thr Ala Tyr Asn Met Asp Ala Pro Gln Asn Ser Val Gly
1265                1270                1275                1280

Glu Phe Ser Val Gly Ser Ala Asp Gly Gln Arg Gln Ile Thr Asn Val
            1285                1290                1295

Ala Ala Gly Ser Ala Asp Thr Asp Ala Val Asn Val Gly Gln Leu Lys
            1300                1305                1310

Val Thr Asp Ala Gln Val Ser Gln Asn Thr Gln Ser Ile Thr Asn Leu
            1315                1320                1325

Asp Asn Arg Val Thr Asn Leu Asp Ser Arg Val Thr Asn Ile Glu Asn
            1330                1335                1340

Gly Ile Gly Asp Ile Val Thr Thr Gly Ser Thr Lys Tyr Phe Lys Thr
1345                1350                1355                1360

Asn Thr Asp Gly Val Asp Ala Ser Ala Gln Gly Lys Asp Ser Val Ala
            1365                1370                1375

Ile Gly Ser Gly Ser Ile Ala Ala Ala Asp Asn Ser Val Ala Leu Gly
            1380                1385                1390

Thr Gly Ser Val Ala Thr Glu Glu Asn Thr Ile Ser Val Gly Ser Ser
            1395                1400                1405

Thr Asn Gln Arg Arg Ile Thr Asn Val Ala Ala Gly Lys Asn Ala Thr
            1410                1415                1420

Asp Ala Val Asn Val Ala Gln Leu Lys Ser Ser Glu Ala Gly Gly Val
1425                1430                1435                1440

Arg Tyr Asp Thr Lys Ala Asp Gly Ser Ile Asp Tyr Ser Asn Ile Thr
            1445                1450                1455

Leu Gly Gly Gly Asn Gly Gly Thr Thr Arg Ile Ser Asn Val Ser Ala
            1460                1465                1470

Gly Val Asn Asn Asn Asp Val Val Asn Tyr Ala Gln Leu Lys Gln Ser
            1475                1480                1485

Val Gln Glu Thr Lys Gln Tyr Thr Asp Gln Arg Met Val Glu Met Asp
            1490                1495                1500

Asn Lys Leu Ser Lys Thr Glu Ser Lys Leu Ser Gly Gly Ile Ala Ser
1505                1510                1515                1520

Ala Met Ala Met Thr Gly Leu Pro Gln Ala Tyr Thr Pro Gly Ala Ser
            1525                1530                1535

Met Ala Ser Ile Gly Gly Gly Thr Tyr Asn Gly Glu Ser Ala Val Ala
```

-continued

```
                    1540                1545                1550
Leu Gly Val Ser Met Val Ser Ala Asn Gly Arg Trp Val Tyr Lys Leu
        1555                1560                1565

Gln Gly Ser Thr Asn Ser Gln Gly Glu Tyr Ser Ala Ala Leu Gly Ala
        1570                1575                1580

Gly Ile Gln Trp
1585

<210> SEQ ID NO 44
<211> LENGTH: 295
<212> TYPE: PRT
<213> ORGANISM: Actinobacillus actinomycetemcomitans

<400> SEQUENCE: 44

Met Thr Tyr Gln Leu Phe Lys His His Leu Val Ala Leu Met Val Thr
  1               5                  10                  15

Gly Ala Ile Ser Val Asn Ala Leu Ala Lys Asp Ser Phe Leu Glu Asn
                 20                  25                  30

Pro Ser Ala Asn Leu Pro Gln Gln Val Phe Lys Asn Arg Val Asp Ile
             35                  40                  45

Phe Asn Asn Glu Thr Asn Ile Asn Glu Asn Lys Lys Asp Ile Ala Ile
         50                  55                  60

Asn Lys Ala Asn Ile Ala Ser Ile Glu Lys Asp Val Met Arg Asn Thr
 65                  70                  75                  80

Gly Gly Ile Asp Arg Leu Ala Lys Gln Glu Leu Val Asn Arg Ala Arg
                 85                  90                  95

Ile Thr Lys Asn Glu Leu Asp Ile Arg Lys Asn Thr Lys Ser Ile Ala
                100                 105                 110

Glu Asn Thr Ala Ser Ile Ala Arg Ile Asp Gly Asn Leu Glu Gly Val
            115                 120                 125

Asn Arg Val Leu Gln Asn Val Asp Val Arg Ser Thr Glu Asn Ala Ala
        130                 135                 140

Arg Ser Arg Ala Asn Glu Gln Lys Ile Ala Glu Asn Lys Lys Ala Ile
145                 150                 155                 160

Glu Asn Lys Ala Asp Lys Ala Asp Val Glu Lys Asn Arg Ala Asp Ile
                165                 170                 175

Ala Ala Asn Ser Arg Ala Ile Ala Thr Phe Arg Ser Ser Gln Asn
            180                 185                 190

Ile Ala Ala Leu Thr Thr Lys Val Asp Arg Asn Thr Ala Arg Ile Asp
        195                 200                 205

Arg Leu Asp Ser Arg Val Asn Glu Leu Asp Lys Glu Val Lys Asn Gly
    210                 215                 220

Leu Ala Ser Gln Ala Ala Leu Ser Gly Leu Phe Gln Pro Tyr Asn Val
225                 230                 235                 240

Gly Ser Leu Asn Leu Ser Ala Val Gly Gly Tyr Lys Ser Lys Thr
                245                 250                 255

Ala Leu Ala Val Gly Ser Gly Tyr Arg Phe Asn Gln Asn Val Ala Ala
                260                 265                 270

Lys Ala Gly Val Ala Val Ser Thr Asn Gly Gly Ser Ala Thr Tyr Asn
            275                 280                 285

Val Gly Leu Asn Phe Glu Trp
        290                 295

<210> SEQ ID NO 45
<211> LENGTH: 452
<212> TYPE: PRT
```

<213> ORGANISM: Haemophilus somnus

<400> SEQUENCE: 45

```
Met Lys Lys Val Gln Phe Phe Lys Tyr Ser Ser Leu Ala Leu Ala Leu
1               5                   10                  15

Gly Leu Gly Val Ser Ala Ser Ala Leu Ala Ala Pro Thr Ser Thr Ser
            20                  25                  30

Thr Thr Thr Gly Pro Glu Ala Pro Thr Gly Pro Ala Pro Thr Ala
        35                  40                  45

Lys Asp Pro Leu Ala Glu Thr Ala Leu Ala Tyr Asp Leu Glu Asn Glu
    50                  55                  60

Val Ala Tyr Leu Arg Met Lys Ala Gly Glu Trp Met Gln Leu Gly Leu
65                  70                  75                  80

Asp Pro Glu Lys Glu Val Ile Lys Gly Trp Asn Glu Val Lys Ser Leu
                85                  90                  95

Pro Arg Ile Asp Gly Asn Gly Lys Asp Lys Gln Thr Lys Asp Gln Ile
            100                 105                 110

Ala Met Leu Ile Arg Thr Val Asp Asn Thr Lys Glu Leu Gly Arg Ile
            115                 120                 125

Val Ser Thr Asn Ile Glu Asp Ile Lys Asn Leu Lys Lys Glu Leu Tyr
    130                 135                 140

Gly Phe Val Glu Asp Val Asn Glu Ser Glu Ala Arg Asn Ile Ser Arg
145                 150                 155                 160

Ile Asp Glu Asn Glu Lys Asp Ile Lys Asn Leu Lys Lys Glu Leu Tyr
                165                 170                 175

Asp Phe Val Glu Asp Val Asn Glu Ser Glu Ala Arg Asn Ile Ser Arg
            180                 185                 190

Ile Asp Glu Asn Glu Lys Asp Ile Asn Thr Leu Lys Glu Leu Met Asp
            195                 200                 205

Glu Asp Leu Asn Ser Val Leu Thr Gln Ile Glu Asp Val Lys Leu Thr
    210                 215                 220

Phe Gln Asp Val Asn Asp Asn Val Asn Leu Ala Phe Glu Glu Ile Asn
225                 230                 235                 240

Gly Asn Ala Gln Lys Phe Asp Thr Ala Ile Glu Gly Leu Thr Ser Gly
                245                 250                 255

Leu Ser Asp Leu Gln Ala Lys Val Asp Ala Asn Lys Gln Glu Thr Glu
            260                 265                 270

Asp Asp Ile Ala Asp Asn Ala Lys Ala Ile His Ser Asn Thr Lys Gly
            275                 280                 285

Ile Ala Lys Asn Thr Lys Asp Ile Arg Asp Leu Asp Thr Lys Thr Lys
    290                 295                 300

Gln Met Leu Glu Asn Asp Lys Asn Leu Met Thr Gly Leu Glu Ser Leu
305                 310                 315                 320

Ala Thr Glu Thr Ser Lys Gly Phe Glu Arg Phe Asp Val Lys Thr Gln
                325                 330                 335

Gln Leu Asp Gln Ala Val Ala Asn Val Val Gly Arg Val Asp Ile Thr
            340                 345                 350

Glu Gln Ala Ile Arg Gln Asn Thr Ala Gly Leu Val Asn Val Asn Lys
            355                 360                 365

Arg Val Asp Thr Leu Asp Lys Asn Thr Lys Ala Gly Ile Ala Ser Ala
    370                 375                 380

Val Ala Leu Gly Met Leu Pro Gln Ser Thr Ala Pro Gly Lys Ser Leu
385                 390                 395                 400

Val Ser Leu Gly Val Gly His His Arg Gly Gln Ser Ala Thr Ala Ile
```

```
                    405                 410                 415
Gly Val Ser Ser Met Ser Ser Asn Gly Lys Trp Val Lys Gly Gly
            420                 425                 430

Met Ser Tyr Asp Thr Gln Arg His Ala Thr Phe Gly Gly Ser Val Gly
            435                 440                 445

Phe Phe Phe Asn
        450

<210> SEQ ID NO 46
<211> LENGTH: 273
<212> TYPE: PRT
<213> ORGANISM: Haemophilus ducreyi

<400> SEQUENCE: 46

Met Lys Ile Lys Cys Leu Val Ala Val Val Gly Leu Ala Cys Ser Thr
1               5                   10                  15

Ile Thr Thr Met Ala Gln Gln Pro Pro Lys Phe Ala Gly Val Ser Ser
            20                  25                  30

Leu Tyr Ser Tyr Glu Tyr Asp Tyr Gly Lys Gly Lys Trp Thr Trp Ser
        35                  40                  45

Asn Glu Gly Gly Phe Asp Ile Lys Val Pro Gly Ile Lys Met Lys Pro
    50                  55                  60

Lys Glu Trp Ile Ser Lys Gln Ala Thr Tyr Leu Glu Leu Gln His Tyr
65                  70                  75                  80

Met Pro Tyr Thr Pro Val Leu Val Thr Ser Ala Pro Asp Val Ser Pro
                85                  90                  95

Ser Ser Ile Ser Ile Leu Leu Tyr Pro Met Ser Asp Pro Asp Gln Leu
            100                 105                 110

Gly Ile Asn Arg Gln Gln Leu Lys Leu Asn Leu Tyr Ser Tyr Phe Asn
        115                 120                 125

Asp Leu Arg His Asp Phe Lys Leu Lys Val Leu Asp Ala Arg Ile Ser
    130                 135                 140

Lys Asn Lys Gln Asn Ile Asp Thr Ile Ser Lys Tyr Leu Leu Glu Leu
145                 150                 155                 160

Gly Thr Tyr Leu Asp Gly Ser Tyr Arg Met Met Glu Gln Asn Thr His
                165                 170                 175

Asn Ile Asn Lys Asn Thr His Asn Ile Asn Lys Asn Thr His Asn Ile
            180                 185                 190

Asn Lys Leu Ser Lys Glu Leu Gln Thr Gly Leu Ala Asn Gln Ser Ala
        195                 200                 205

Leu Ser Met Leu Val Gln Pro Asn Gly Val Gly Lys Thr Ser Val Ser
    210                 215                 220

Ala Ala Val Gly Gly Tyr Arg Asp Lys Thr Ala Leu Ala Ile Gly Val
225                 230                 235                 240

Gly Ser Arg Ile Thr Asp Arg Phe Thr Ala Lys Ala Gly Val Ala Phe
                245                 250                 255

Asn Thr Tyr Asn Gly Gly Met Ser Tyr Gly Ala Ser Val Gly Tyr Glu
            260                 265                 270

Phe

<210> SEQ ID NO 47
<211> LENGTH: 338
<212> TYPE: PRT
<213> ORGANISM: Escherichia coli

<400> SEQUENCE: 47
```

Met Lys Thr Val Asn Val Ala Leu Leu Ala Leu Ile Ile Ser Ala Thr
1               5                   10                  15

Ser Ser Pro Phe Val Leu Ala Gly Asp Thr Ile Glu Ala Ala Ala Thr
            20                  25                  30

Glu Leu Ser Ala Ile Asn Ser Gly Met Ser Gln Ser Glu Ile Glu Gln
        35                  40                  45

Lys Ile Thr Arg Phe Leu Glu Arg Thr Asp Asn Ser Pro Ala Ala Tyr
50                  55                  60

Thr Tyr Leu Thr Glu His His Tyr Ile Pro Ser Glu Thr Pro Asp Thr
65                  70                  75                  80

Thr Gln Thr Pro Pro Val Gln Thr Asp Pro Asp Ala Gly Gln Lys Thr
                85                  90                  95

Val Ala Ala Thr Gly Asp Val Gln Thr Thr Ala Arg Tyr Gln Ser Met
                100                 105                 110

Ile Asn Ala Arg Gln Ser Thr Val Thr Asp Ala Gln Gln Thr Gln Ile
            115                 120                 125

Thr Glu Gln Gln Ala Gln Ile Val Ala Thr Gln Lys Thr Leu Ala Ala
    130                 135                 140

Thr Gly Asp Thr Gln Asn Thr Ala His Tyr Gln Glu Met Ile Asn Ala
145                 150                 155                 160

Arg Leu Ala Ala Gln Asn Glu Ala Asn Gln Arg Thr Thr Thr Glu Gln
                165                 170                 175

Gly Gln Lys Met Asn Ala Leu Thr Thr Asp Val Ala Ala Gln Gln Gln
            180                 185                 190

Lys Glu Arg Ala Gln Tyr Asp Lys Gln Met Gln Ser Leu Ala Gln Lys
        195                 200                 205

Ser Val Gln Ala His Glu Gln Ile Glu Ser Leu Arg Gln Asp Ser Ala
    210                 215                 220

Gln Thr Gln Gln Gln Leu Thr Asn Thr Gln Lys Arg Val Ala Asp Asn
225                 230                 235                 240

Ser Gln Gln Ile Asn Thr Leu Asn Asn His Phe Ser Ser Leu Lys Asn
                245                 250                 255

Glu Val Glu Asp Asn Arg Lys Glu Ala Asn Ala Gly Thr Ala Ser Ala
            260                 265                 270

Ile Ala Ile Ala Ser Gln Pro Gln Val Lys Thr Gly Asp Leu Met Met
        275                 280                 285

Val Ser Ala Gly Ala Gly Thr Phe Asn Gly Glu Ser Ala Val Ser Val
    290                 295                 300

Gly Thr Ser Phe Asn Ala Gly Thr His Thr Val Leu Lys Ala Gly Ile
305                 310                 315                 320

Ser Ala Asp Thr Gln Ser Asp Phe Gly Ala Gly Val Gly Val Gly Tyr
                325                 330                 335

Ser Phe

<210> SEQ ID NO 48
<211> LENGTH: 577
<212> TYPE: PRT
<213> ORGANISM: Escherichia coli

<400> SEQUENCE: 48

Met Leu Ile Gln Gln Asn Ser Glu Val Ile Asn Gln Leu Ala Gly Asn
1               5                   10                  15

Thr Ser Glu Thr Tyr Ile Glu Glu Asn Gly Ala Ser Ile Asn Tyr Val
            20                  25                  30

Arg Thr Asn Asp Thr Gly Leu Thr Phe Thr Asp Ala Ser Ala Ala Gly

-continued

```
              35                  40                  45
Ile Gly Ser Thr Ala Val Gly Tyr Asn Thr Val Ala Lys Gly Asp Asn
 50                  55                  60
Ser Val Ala Met Gly Tyr Asn Ser Phe Ala Glu Gly His Ser Ser Val
 65                  70                  75                  80
Ala Ile Gly Gln Gly Ser Tyr Ser Gly Val Glu Thr Ser Ile Ala Leu
                 85                  90                  95
Gly Ser Glu Ser Val Ser Ser Arg Val Ile Val Lys Gly Ser Arg Asn
                100                 105                 110
Thr Ser Val Ser Glu Glu Gly Val Val Ile Gly Tyr Asp Thr Thr Asp
            115                 120                 125
Gly Glu Leu Leu Gly Ala Leu Ser Ile Gly Asp Asp Gly Lys Tyr Arg
130                 135                 140
Gln Ile Ile Asn Val Ala Asp Gly Ser Glu Ala His Asp Ala Val Thr
145                 150                 155                 160
Val Arg Gln Leu Gln Asn Ala Ile Gly Ala Val Ala Thr Thr Pro Thr
                165                 170                 175
Lys Tyr Tyr His Ala Asn Ser Thr Ala Glu Asp Ser Leu Ala Val Gly
                180                 185                 190
Glu Asp Ser Leu Ala Met Gly Ala Lys Thr Ile Val Asn Gly Asn Ala
            195                 200                 205
Gly Ile Gly Ile Gly Leu Asn Thr Leu Val Leu Ala Asp Ala Ile Asn
210                 215                 220
Gly Ile Ala Ile Gly Ser Asn Ala Arg Ala Asn His Ala Asp Ser Ile
225                 230                 235                 240
Ala Met Gly Asn Gly Ser Gln Thr Thr Arg Gly Ala Gln Thr Asn Tyr
                245                 250                 255
Thr Ala Tyr Asn Met Asp Ala Pro Gln Asn Ser Val Gly Glu Phe Ser
            260                 265                 270
Val Gly Ser Glu Asp Gly Gln Arg Gln Ile Thr Asn Val Ala Ala Gly
        275                 280                 285
Ser Ala Asp Thr Asp Ala Val Asn Val Gly Gln Leu Lys Val Thr Asp
290                 295                 300
Ala Gln Val Ser Gln Asn Thr Gln Ser Ile Thr Asn Leu Asn Thr Gln
305                 310                 315                 320
Val Thr Asn Leu Asp Thr Arg Val Thr Asn Ile Glu Asn Gly Ile Gly
                325                 330                 335
Asp Ile Val Thr Thr Gly Ser Thr Lys Tyr Phe Lys Thr Asn Thr Asp
            340                 345                 350
Gly Val Asp Ala Asn Ala Gln Gly Lys Asp Ser Val Ala Ile Gly Ser
        355                 360                 365
Gly Ser Ile Ala Ala Ala Asp Asn Ser Val Ala Leu Gly Thr Gly Ser
370                 375                 380
Val Ala Asn Glu Glu Asn Thr Ile Ser Val Gly Ser Ser Thr Asn Gln
385                 390                 395                 400
Arg Arg Ile Thr Asn Val Ala Ala Gly Val Asn Ala Thr Asp Ala Val
                405                 410                 415
Asn Val Ser Gln Leu Lys Ser Ser Glu Ala Gly Gly Val Arg Tyr Asp
            420                 425                 430
Thr Lys Ala Asp Gly Ser Ile Asp Tyr Ser Asn Ile Thr Leu Gly Gly
        435                 440                 445
Gly Asn Gly Gly Thr Thr Arg Ile Ser Asn Val Ser Ala Gly Val Asn
450                 455                 460
```

```
Asn Asn Asp Ala Val Asn Tyr Ala Gln Leu Lys Gln Ser Val Gln Glu
465                 470                 475                 480

Thr Lys Gln Tyr Thr Asp Gln Arg Met Val Glu Met Asp Asn Lys Leu
                485                 490                 495

Ser Lys Thr Glu Ser Lys Leu Ser Gly Gly Ile Ala Ser Ala Met Ala
            500                 505                 510

Met Thr Gly Leu Pro Gln Ala Tyr Thr Pro Gly Ala Ser Met Ala Ser
            515                 520                 525

Ile Gly Gly Gly Thr Tyr Asn Gly Glu Ser Ala Val Ala Leu Gly Val
        530                 535                 540

Ser Met Val Ser Ala Asn Gly Arg Trp Val Tyr Lys Leu Gln Gly Ser
545                 550                 555                 560

Thr Asn Ser Gln Gly Glu Tyr Ser Ala Ala Leu Gly Ala Gly Ile Gln
                565                 570                 575

Trp

<210> SEQ ID NO 49
<211> LENGTH: 717
<212> TYPE: PRT
<213> ORGANISM: Escherichia coli

<400> SEQUENCE: 49

Met Lys Thr Val Lys Leu Ser Leu Leu Ala Val Val Val Ala Thr Ala
1               5                   10                  15

Val Ser Pro Ser Ala Phe Ala Gly Asp Thr Val Glu Ala Ala Thr Thr
            20                  25                  30

Glu Leu Thr Val Ile Gln Pro Gly Met Ser Gln Ser Glu Ile Asp Gln
            35                  40                  45

Lys Ile Gly Arg Phe Leu Glu Arg Thr Gly Asn Ser Val Ala Ala Gln
    50                  55                  60

Asn Tyr Leu Ile Ala His Asp Tyr Gln Thr Thr Thr Pro Gln Glu Asn
65                  70                  75                  80

Thr Ala Ala Ser Pro Val Gln Pro Thr Asn Thr Leu Asn Pro Ile Thr
                85                  90                  95

Asn Gln Ala Gln Thr Asp Arg Asp Asn Gly Gln Asp Thr Ala Ile Gln
            100                 105                 110

Asp Ala Gln His Ala Ala Asn Trp Ala Ser Leu Lys Ala Asp Asp Ala
            115                 120                 125

Gln His Ala Ile Thr Val Ala Gln Thr Asp Ile Asp Ala Asn Thr Ala
    130                 135                 140

Ala Ile Thr Asp Thr Arg Asn Asp Val Ser Ala Val Gln Ser Asp Val
145                 150                 155                 160

Thr Asn Ile Lys Gly Asp Val Ala His Ala Gln Ser Thr Ala Asp His
                165                 170                 175

Ala Asn Ala Asn Ala Asn Thr Ala Leu Ile Asn Gly Val Lys Leu Ser
            180                 185                 190

Gly Ala Val Thr Glu Asn Lys Asn Asn Ile Glu Gln Asn Arg Ser Asp
            195                 200                 205

Ile Ala Asp Gln Gln Lys Leu Leu Ala Ser Asn Glu Gln Lys Gln Ile
    210                 215                 220

Val Arg Asp Asn Gly Gln Asp Thr Ala Ile Gln Asp Ala Gln His Ala
225                 230                 235                 240

Ala Asn Trp Ala Ser Leu Lys Ala Asp Asp Ala Gln His Ala Ile Thr
                245                 250                 255

Val Ala Gln Thr Asp Ile Asp Ala Asn Lys Ala Ala Ile Thr Asp Ile
```

-continued

```
                260                 265                 270
Arg Asn Asp Val Ser Ala Val Gln Ser Asp Val Thr Asn Ile Lys Gly
                275                 280                 285
Asp Val Ala His Ala Gln Ser Thr Ala Asp His Ala Asn Ala Asn Ala
                290                 295                 300
Asn Thr Ala Leu Met Asn Gly Val Lys Leu Ser Ser Ala Val Thr Glu
305                 310                 315                 320
Asn Lys Asn Asn Ile Glu Gln Asn Arg Ser Asp Ile Ala Asp Gln Gln
                325                 330                 335
Lys Leu Leu Ala Ser Asn Glu Gln Lys Gln Ile Val Arg Asp Asn Gly
                340                 345                 350
Gln Asp Thr Ala Ile Gln Asp Ala Gln His Ala Ala Asn Trp Ala Ser
                355                 360                 365
Met Lys Ala Asp Asp Ala Gln His Ala Ile Thr Val Ala Gln Thr Asp
                370                 375                 380
Ile Asp Ala Asn Lys Ala Ala Ile Ala Asp Thr Arg Asn Asp Val Ser
385                 390                 395                 400
Ala Val Gln Ser Asp Val Thr Asn Ile Lys Gly Asp Val Ala His Ala
                405                 410                 415
Gln Ser Thr Ala Asp His Ala Asn Ala Asn Ala Asn Thr Ala Leu Ile
                420                 425                 430
Asn Gly Val Lys Leu Ser Gly Ala Val Thr Glu Asn Lys Asn Asn Ile
                435                 440                 445
Glu Gln Asn Arg Ser Asp Ile Ala Asp Gln Gln Gln Leu Asp Glu
                450                 455                 460
Thr Arg Lys Ile Val Ala Ala Thr Gly Asp Val Gln Thr Ala Ala Arg
465                 470                 475                 480
Tyr Gln Ser Met Ile Asp Ala Arg Gln Thr Ala Ala Asn Ala Gln
                485                 490                 495
Gln Ala Gln Ala Asp Thr Gln Gln Gln Met Asp Asp Gln Gln Lys
                500                 505                 510
Gln Ile Asp Ala Thr Gln Lys Thr Val Ser Ala Leu Gly Asp Ala Gln
                515                 520                 525
Thr Asn Ala His Tyr Gln Glu Met Val Asn Ala Gly Leu Arg Ala Gln
                530                 535                 540
Asn Asp Ala Asn Ala Arg Thr Ala Ala Glu Gln Lys Gln Lys Ile Asp
545                 550                 555                 560
Thr Leu Ala Thr Asn Gln Ala Thr Gln Gln His Ile Asn Ser Val Gln
                565                 570                 575
Tyr Gly Glu Gln Ile Gln Arg Leu Ala Gln Asp Ser Thr Gln Thr His
                580                 585                 590
Glu Gln Ile Asp Ser Leu Thr Gln Asp Val Thr Gln Thr His Gln Gln
                595                 600                 605
Leu Ser Asn Thr Gln Lys Arg Val Ala Asp Asn Ser Gln Gln Ile Thr
                610                 615                 620
Thr Leu Asn Asn His Phe Ser Ser Leu Lys Asn Glu Val Glu Asp Asn
625                 630                 635                 640
Arg Lys Glu Ala Asn Ala Gly Thr Ala Ser Ala Ile Ala Ile Ala Ser
                645                 650                 655
Gln Pro Gln Val Lys Ala Gly Asp Phe Met Met Met Ser Ala Gly Ala
                660                 665                 670
Gly Thr Phe Asn Gly Glu Ser Ala Val Ser Val Gly Thr Ser Phe Asn
                675                 680                 685
```

```
Ala Gly Thr His Thr Val Ile Lys Ala Gly Val Ser Ala Asp Thr Gln
        690                 695                 700

Ser Asp Phe Gly Ala Gly Val Gly Val Gly Tyr Ser Phe
705                 710                 715

<210> SEQ ID NO 50
<211> LENGTH: 1743
<212> TYPE: PRT
<213> ORGANISM: Escherichia coli

<400> SEQUENCE: 50

Met Asn Lys Ile Phe Lys Val Ile Trp Asn Pro Ala Thr Gly Ser Tyr
1               5                   10                  15

Thr Val Ala Ser Glu Thr Ala Lys Ser Arg Gly Lys Lys Ser Gly Arg
            20                  25                  30

Ser Lys Leu Leu Ile Ser Ala Leu Val Ala Gly Gly Met Leu Ser Ser
        35                  40                  45

Phe Gly Val Gln Ala Gln Ala Gly Arg Asp Asn Gly Gln Gly Val Asn
    50                  55                  60

Tyr Gly Gln Gly Thr Gly Thr Gly Trp Val Ala Ile Gly Glu Asp Ala
65                  70                  75                  80

Lys Ala Asn Ser Phe Thr Asp Thr Gly Gly Gly Ser Ser Thr Ala Val
                85                  90                  95

Gly Tyr His Ser Thr Ala Asp Gly Arg Trp Ser Thr Ala Leu Gly Ala
            100                 105                 110

Lys Thr His Ser Leu Gly Glu Ala Ser Val Ala Leu Gly Ile Asn Thr
        115                 120                 125

Thr Ser Ala Gly Glu Arg Ser Leu Ala Ile Gly Ala Ser Ala Thr Ser
    130                 135                 140

Thr Gly Gly Phe Ser Ile Ala Leu Gly Arg Tyr Ala Asn Ser Val Gly
145                 150                 155                 160

Glu Phe Ser Ile Ala Gln Gly Asp His Ala Gly Thr Gly Ala Asp Asp
                165                 170                 175

Ala Ile Ala Phe Gly Arg Glu Ser Lys Ala Leu Gly Ile Met Ser Ile
            180                 185                 190

Ala Leu Gly Ala Thr Ala Asn Ala Ser Lys Glu Tyr Ala Met Ala Leu
        195                 200                 205

Gly Ala Ser Ser Ala Ala Ser Ala Ala Asn Ala Ile Ala Val Gly Arg
    210                 215                 220

Asn Ser Ala Ala Ala Gly Val Asp Ser Leu Ala Phe Gly Arg Gln Ser
225                 230                 235                 240

Ala Ala Ser Ala Ala Asn Ala Ile Ala Met Gly Ala Glu Ser Lys Ala
                245                 250                 255

Ala Glu Asn Ala Thr Ala Val Gly Thr Asn Ala Glu Ala Asn Gly Leu
            260                 265                 270

Asn Ser Ile Ala Leu Gly Ser Gly Ser Ile Ala Asp Val Asp Asn Thr
        275                 280                 285

Ile Ala Leu Gly Asn Gln Ser Gln Ala Val Ala Gly Ala Ile Ala
    290                 295                 300

Ile Gly Gln Gly Asn Lys Ala Asp Gly Ala Asn Ala Ile Ala Leu Gly
305                 310                 315                 320

Asn Gly Ser Ile Thr Gly Gly Val Asn Ala Ile Ala Leu Gly Gln Gly
                325                 330                 335

Ser Tyr Ala Gly Leu Glu Asn Gly Thr Ala Ile Gly Ala Gln Ala Ser
            340                 345                 350
```

-continued

```
Ala Gln Gly Lys Asn Ser Val Ala Leu Gly Ala Gly Ser Val Ala Thr
            355                 360                 365
Asp Ala Asp Thr Val Ser Val Gly Asn Thr Thr Ala Gln Arg Gln Ile
370                 375                 380
Val Asn Met Ala Ala Gly Asp Ile Ser Thr Thr Ser Thr Asp Ala Ile
385                 390                 395                 400
Asn Gly Ser Gln Leu Tyr Ala Ile Ser Lys Ser Val Ala Asp Asn Leu
                405                 410                 415
Gly Gly Gly Ala Thr Val Asn Ala Gln Gly Val Val Thr Ser Pro Asn
            420                 425                 430
Tyr Arg Leu Lys Ser Gly Ile Phe Gly Thr Val Gly Asp Ala Leu Thr
                435                 440                 445
Gly Leu Asp Asn Asn Thr Leu Gln Trp Asp Ser Leu Lys Lys Ala Tyr
450                 455                 460
Ser Ala Ala His Gly Thr Asp Thr Thr Ser Thr Ile Thr Asn Val Lys
465                 470                 475                 480
Asp Gly Ala Ile Ser Asp Thr Ser Lys Asp Ala Val Asn Gly Ser Gln
                485                 490                 495
Leu Lys Thr Thr Asn Asp Asn Val Ala Thr Asn Thr Ala Asn Ile Thr
            500                 505                 510
Thr Asn Thr Asn Ser Ile Asn Thr Leu Thr Asp Ser Val Gly Asp Leu
                515                 520                 525
Lys Asp Asp Ala Leu Leu Trp Asn Gly Thr Ala Phe Ser Ala Ala His
530                 535                 540
Gly Thr Glu Ala Thr Ser Lys Ile Thr Asn Val Lys Asp Gly Asp Leu
545                 550                 555                 560
Thr Ala Gly Ser Thr Asp Ala Val Asn Gly Ser Gln Leu Lys Thr Thr
                565                 570                 575
Asn Asp Asn Val Ala Thr Asn Thr Thr Asn Ile Thr Asn Leu Thr Asp
            580                 585                 590
Ser Val Gly Asp Leu Lys Asp Asp Ala Leu Leu Trp Asn Gly Thr Ala
                595                 600                 605
Phe Ser Ala Ala His Gly Thr Asp Ala Thr Ser Lys Ile Thr Asn Val
610                 615                 620
Lys Asp Gly Asp Leu Thr Ala Gly Ser Thr Asp Ala Val Asn Gly Ser
625                 630                 635                 640
Gln Leu Lys Thr Thr Asn Asp Ala Val Ala Ala Asn Thr Thr Asn Ile
                645                 650                 655
Ala Thr Asn Thr Thr Asn Ile Thr Asn Leu Thr Asp Ala Val Asp Ser
            660                 665                 670
Leu Gly Asp Asp Ser Leu Leu Trp Asn Ala Thr Ala Gly Ala Phe Ser
                675                 680                 685
Ala Ala His Gly Thr Asp Ala Thr Ser Lys Ile Thr Asn Val Thr Ala
690                 695                 700
Gly Asp Leu Thr Ala Gly Ser Thr Asp Ala Val Asn Gly Ser Gln Leu
705                 710                 715                 720
Lys Thr Thr Asn Asp Ala Val Ala Ala Asn Thr Thr Asn Ile Ala Thr
                725                 730                 735
Asn Thr Thr Asn Ile Thr Asn Leu Thr Asp Ala Val Asp Ser Leu Gly
            740                 745                 750
Asp Asp Ser Leu Leu Trp Asn Ala Thr Ala Gly Ala Phe Ser Ala Ala
                755                 760                 765
His Gly Thr Asp Ala Thr Ser Lys Ile Thr Asn Val Lys Asp Gly Asp
770                 775                 780
```

```
Leu Thr Ala Gly Ser Thr Asp Ala Val Asn Gly Ser Gln Leu Lys Thr
785                 790                 795                 800

Thr Asn Asp Ala Val Ala Ala Asn Thr Thr Asn Ile Ala Thr Asn Thr
                805                 810                 815

Thr Asn Ile Thr Asn Leu Thr Asp Ala Val Asp Ser Leu Gly Asp Asp
            820                 825                 830

Ser Leu Leu Trp Asn Ala Thr Ala Gly Ala Phe Ser Ala Lys His Gly
        835                 840                 845

Thr Asn Gly Thr Asp Ser Lys Ile Thr Asn Leu Leu Ala Gly Thr Val
    850                 855                 860

Ser Ser Asp Ser Thr Asp Ala Ile Asn Gly Ser Gln Leu Tyr Gly Leu
865                 870                 875                 880

Ala Asp Ser Phe Thr Ser Tyr Leu Gly Gly Ala Asp Ile Ser Asp
                885                 890                 895

Ala Gly Val Leu Thr Gly Pro Thr Tyr Thr Ile Gly Gly Thr Asp Tyr
            900                 905                 910

Asn Asn Val Gly Asp Ala Leu Ala Ala Ile Asn Thr Ser Phe Ser Thr
        915                 920                 925

Ser Leu Gly Asp Ala Leu Leu Trp Asp Ala Thr Ala Lys Gly Gly Asp
    930                 935                 940

Gly Ala Phe Ser Ala Gly Arg Gly Thr Asp Asn Thr Ala Ser Ile Ile
945                 950                 955                 960

Thr Asn Val Ala Asp Gly Ala Ile Ser Ser Thr Ser Asp Ala Ile
                965                 970                 975

Asn Gly Ser Gln Leu Tyr Asp Thr Ser Lys Tyr Ile Ala Asp Thr Leu
            980                 985                 990

Gly Gly Asp Ala Glu Val Asn Ala Asp Gly Thr Ile Thr Ala Pro Thr
        995                 1000                1005

Tyr Ala Ile Ala Gly Gly Ser Tyr Ser Asn Val Gly Asp Ala Leu Glu
    1010                1015                1020

Ala Ile Asp Thr Thr Leu Asp Asp Ala Leu Leu Trp Asp Ala Thr Ala
1025                1030                1035                1040

Asn Asp Gly Asn Gly Ala Phe Ser Ala Ala His Gly Lys Asp Lys Thr
                1045                1050                1055

Ala Ser Val Ile Thr Asn Val Ala Asn Gly Ala Ile Ser Ala Thr Ser
            1060                1065                1070

Ser Asp Ala Ile Asn Gly Ser Gln Leu Tyr Thr Thr Asn Lys Tyr Ile
        1075                1080                1085

Ala Asp Ala Leu Gly Gly Asp Ala Glu Val Asn Ala Asp Gly Ser Ile
    1090                1095                1100

Thr Ala Pro Thr Tyr Thr Ile Ala Asn Ala Glu Tyr Asn Asn Val Gly
1105                1110                1115                1120

Asp Ala Leu Asp Ala Leu Asp Asp Asn Ala Leu Leu Trp Asp Ala Thr
                1125                1130                1135

Ala Asn Asp Gly Ala Gly Ala Tyr Asn Ala Ser His Asp Gly Lys Ala
            1140                1145                1150

Ser Ile Ile Thr Asn Val Ala Asp Gly Asn Ile Gly Glu Gly Ser Thr
        1155                1160                1165

Asp Ala Ile Asn Gly Ser Gln Leu Phe Asn Thr Asn Met Leu Ile Gln
    1170                1175                1180

Gln Asn Ser Glu Ile Ile Asn Gln Leu Ala Gly Asn Thr Ser Glu Thr
1185                1190                1195                1200

Tyr Ile Glu Asp Asn Gly Ala Gly Ile Asn Tyr Val Arg Thr Asn Asp
```

-continued

```
                1205                1210                1215
Asn Gly Leu Ala Phe Asn Asp Ala Ser Ala Ser Gly Ile Gly Ala Thr
            1220                1225                1230
Ala Val Gly Tyr Asn Ala Val Ala Ser Gly Glu Ser Ser Val Ala Ile
            1235                1240                1245
Gly Gln Gly Ser Ser Ser Asn Val Asp Thr Gly Ile Ala Leu Gly Ser
            1250                1255                1260
Ser Ser Val Ser Ser Arg Val Ile Val Lys Gly Ser Arg Asp Thr Ser
1265                1270                1275                1280
Val Ser Glu Glu Gly Val Val Ile Gly Tyr Asp Thr Thr Asp Gly Glu
                1285                1290                1295
Leu Leu Gly Ala Leu Ser Ile Gly Asp Asp Gly Lys Tyr Arg Gln Ile
                1300                1305                1310
Ile Asn Val Ala Asp Gly Ser Glu Ala His Asp Ala Val Thr Val Arg
                1315                1320                1325
Gln Leu Gln Asn Ala Ile Gly Ala Val Ala Thr Thr Pro Thr Lys Tyr
                1330                1335                1340
Phe His Ala Asn Ser Thr Glu Glu Asp Ser Leu Ala Val Gly Glu Asp
1345                1350                1355                1360
Ser Leu Ala Met Gly Ala Lys Thr Ile Val Asn Gly Asn Ala Gly Ile
                1365                1370                1375
Gly Ile Gly Tyr Gly Ala Tyr Val Asp Ala Asn Ala Leu Asn Gly Ile
                1380                1385                1390
Ala Ile Gly Ser Asn Ala Arg Ala Asn His Ala Asn Ser Ile Ala Met
                1395                1400                1405
Gly Asn Gly Ser Gln Thr Thr Arg Gly Ala Gln Thr Gly Tyr Ala Ala
            1410                1415                1420
Tyr Asn Met Asp Ala Pro Gln Asn Ser Val Gly Glu Phe Ser Val Gly
1425                1430                1435                1440
Ser Glu Asp Gly Gln Arg Gln Ile Thr Asn Val Ala Ala Gly Ser Ala
                1445                1450                1455
Asp Thr Asp Ala Val Asn Val Gly Gln Leu Lys Val Thr Asp Ala Gln
                1460                1465                1470
Val Ser Gln Asn Thr Gln Ser Ile Thr Asn Leu Asn Asn Gln Val Thr
            1475                1480                1485
Asn Leu Asp Thr Arg Val Thr Asn Ile Glu Asn Gly Ile Gly Asp Ile
            1490                1495                1500
Val Thr Thr Gly Ser Thr Lys Tyr Phe Lys Thr Asn Thr Asp Gly Val
1505                1510                1515                1520
Asp Ala Asn Ala Gln Gly Lys Asp Ser Val Ala Ile Gly Ser Gly Ser
                1525                1530                1535
Ile Ala Ala Ala Asp Asn Ser Val Ala Leu Gly Thr Gly Ser Val Ala
            1540                1545                1550
Asn Glu Glu Asn Thr Ile Ser Val Gly Ser Ser Thr Asn Gln Arg Arg
            1555                1560                1565
Ile Thr Asn Val Ala Ala Gly Val Asn Ala Thr Asp Ala Val Asn Val
            1570                1575                1580
Ser Gln Leu Lys Ser Ser Glu Ala Gly Gly Val Arg Tyr Asp Thr Lys
1585                1590                1595                1600
Ala Asp Gly Ser Val Asp Tyr Ser Asn Ile Thr Leu Gly Gly Gly Asn
                1605                1610                1615
Gly Gly Thr Thr Arg Ile Ser Asn Val Ser Ala Gly Val Asn Asn Asn
                1620                1625                1630
```

```
Asp Ala Val Asn Tyr Ala Gln Leu Lys Gln Ser Val Gln Glu Thr Lys
            1635                1640                1645

Gln Tyr Thr Asp Gln Arg Met Val Glu Met Asp Asn Lys Leu Ser Lys
        1650                1655                1660

Thr Glu Ser Lys Leu Ser Gly Ile Ala Ser Ala Met Ala Met Thr
1665                1670                1675                1680

Gly Leu Pro Gln Ala Tyr Thr Pro Gly Ala Ser Met Ala Ser Ile Gly
                1685                1690                1695

Gly Gly Thr Tyr Asn Gly Glu Ser Ala Val Ala Leu Gly Val Ser Met
            1700                1705                1710

Val Ser Ala Asn Gly Arg Trp Val Tyr Lys Leu Gln Gly Ser Thr Asn
            1715                1720                1725

Ser Gln Gly Glu Tyr Ser Ala Ala Leu Gly Ala Gly Ile Gln Trp
        1730                1735                1740

<210> SEQ ID NO 51
<211> LENGTH: 1778
<212> TYPE: PRT
<213> ORGANISM: Escherichia coli

<400> SEQUENCE: 51

Met Asn Lys Ile Phe Lys Val Ile Trp Asn Pro Ala Thr Gly Ser Tyr
1               5                   10                  15

Thr Val Ala Ser Glu Thr Ala Lys Ser Arg Gly Lys Lys Ser Gly Arg
            20                  25                  30

Ser Lys Leu Leu Ile Ser Ala Leu Val Ala Gly Gly Leu Leu Ser Ser
        35                  40                  45

Phe Gly Ala Ser Ala Asp Asn Tyr Thr Gly Gln Pro Thr Asp Tyr Gly
    50                  55                  60

Asp Gly Ser Ala Gly Asp Gly Trp Val Ala Ile Gly Lys Gly Ala Lys
65                  70                  75                  80

Ala Asn Thr Phe Met Asn Thr Ser Gly Ala Ser Thr Ala Leu Gly Tyr
                85                  90                  95

Asp Ala Ile Ala Glu Gly Glu Tyr Ser Ser Ala Ile Gly Ser Lys Thr
            100                 105                 110

Leu Ala Thr Gly Gly Ala Ser Met Ala Phe Gly Val Ser Ala Lys Ala
        115                 120                 125

Met Gly Asp Arg Ser Val Ala Leu Gly Ala Ser Ser Val Ala Asn Gly
    130                 135                 140

Asp Arg Ser Met Ala Phe Gly Arg Tyr Ala Lys Thr Asn Gly Phe Thr
145                 150                 155                 160

Ser Leu Ala Ile Gly Asp Ser Ser Leu Ala Asp Gly Glu Lys Thr Ile
                165                 170                 175

Ala Leu Gly Asn Thr Ala Lys Ala Tyr Glu Ile Met Ser Ile Ala Leu
            180                 185                 190

Gly Asp Asn Ala Asn Ala Ser Lys Glu Tyr Ala Met Ala Leu Gly Ala
        195                 200                 205

Ser Ser Lys Ala Gly Gly Ala Asp Ser Leu Ala Phe Gly Arg Lys Ser
    210                 215                 220

Thr Ala Asn Ser Thr Gly Ser Leu Ala Ile Gly Ala Asp Ser Ser Ser
225                 230                 235                 240

Ser Asn Asp Asn Ala Ile Ala Ile Gly Asn Lys Thr Gln Ala Leu Gly
                245                 250                 255

Val Asn Ser Met Ala Leu Gly Asn Ala Ser Gln Ala Ser Gly Glu Ser
            260                 265                 270
```

-continued

```
Ser Ile Ala Leu Gly Asn Thr Ser Glu Ala Ser Glu Gln Asn Ala Ile
            275                 280                 285
Ala Leu Gly Gln Gly Ser Ile Ala Ser Lys Val Asn Ser Ile Ala Leu
        290                 295                 300
Gly Ser Asn Ser Leu Ser Ser Gly Glu Asn Ala Ile Ala Leu Gly Glu
305                 310                 315                 320
Gly Ser Ala Ala Gly Gly Ser Asn Ser Leu Ala Phe Gly Ser Gln Ser
                325                 330                 335
Arg Ala Asn Gly Asn Asp Ser Val Ala Ile Gly Val Gly Ala Ala Ala
                340                 345                 350
Ala Thr Asp Asn Ser Val Ala Ile Gly Ala Gly Ser Thr Thr Asp Ala
            355                 360                 365
Ser Asn Thr Val Ser Val Gly Asn Ser Ala Thr Lys Arg Lys Ile Val
    370                 375                 380
Asn Met Ala Ala Gly Ala Ile Ser Asn Thr Ser Thr Asp Ala Ile Asn
385                 390                 395                 400
Gly Ser Gln Leu Tyr Thr Ile Ser Asp Ser Val Ala Lys Arg Leu Gly
                405                 410                 415
Gly Gly Ala Thr Val Gly Ser Asp Gly Thr Val Thr Ala Val Ser Tyr
                420                 425                 430
Ala Leu Arg Ser Gly Thr Tyr Asn Asn Val Gly Asp Ala Leu Ser Gly
            435                 440                 445
Ile Asp Asn Asn Thr Leu Gln Trp Asn Lys Thr Ala Gly Ala Phe Ser
    450                 455                 460
Ala Asn His Gly Ala Asn Ala Thr Asn Lys Ile Thr Asn Val Ala Lys
465                 470                 475                 480
Gly Thr Val Ser Ala Thr Ser Thr Asp Val Val Asn Gly Ser Gln Leu
                485                 490                 495
Tyr Asp Leu Gln Gln Asp Ala Leu Leu Trp Asn Gly Thr Ala Phe Ser
                500                 505                 510
Ala Ala His Gly Thr Glu Ala Thr Ser Lys Ile Thr Asn Val Thr Ala
            515                 520                 525
Gly Asn Leu Thr Ala Gly Ser Thr Asp Ala Val Asn Gly Ser Gln Leu
    530                 535                 540
Lys Thr Thr Asn Asp Asn Val Thr Thr Asn Thr Thr Asn Ile Ala Thr
545                 550                 555                 560
Asn Thr Thr Asn Ile Thr Asn Leu Thr Asp Ala Val Asn Gly Leu Gly
                565                 570                 575
Asp Asp Ser Leu Leu Trp Asn Lys Ala Gly Ala Phe Ser Ala Ala
            580                 585                 590
His Gly Thr Glu Ala Thr Ser Lys Ile Thr Asn Val Thr Ala Gly Asn
            595                 600                 605
Leu Thr Ala Gly Ser Thr Asp Ala Val Asn Gly Ser Gln Leu Lys Thr
            610                 615                 620
Thr Asn Asp Asn Val Thr Thr Asn Thr Thr Asn Ile Ala Thr Asn Thr
625                 630                 635                 640
Thr Asn Ile Thr Asn Leu Thr Asp Ala Val Asn Gly Leu Gly Asp Asp
                645                 650                 655
Ser Leu Leu Trp Asn Lys Thr Ala Gly Ala Phe Ser Ala Ala His Gly
                660                 665                 670
Thr Asp Ala Thr Ser Lys Ile Thr Asn Val Thr Ala Gly Asn Leu Thr
            675                 680                 685
Ala Gly Ser Thr Asp Ala Val Asn Gly Ser Gln Leu Lys Thr Thr Asn
690                 695                 700
```

```
Asp Asn Val Thr Thr Asn Thr Thr Asn Ile Ala Thr Asn Thr Thr Asn
705                 710                 715                 720

Ile Thr Asn Leu Thr Asp Ala Val Asn Gly Leu Gly Asp Asp Ser Leu
            725                 730                 735

Leu Trp Asn Lys Thr Ala Gly Ala Phe Ser Ala Ala His Gly Thr Asp
                740                 745                 750

Ala Thr Ser Lys Ile Thr Asn Val Lys Ala Gly Asp Leu Thr Ala Gly
            755                 760                 765

Ser Thr Asp Ala Val Asn Gly Ser Gln Leu Lys Thr Thr Asn Asp Asn
770                 775                 780

Val Ser Thr Asn Thr Thr Asn Ile Thr Asn Leu Thr Asp Ala Val Asn
785                 790                 795                 800

Gly Leu Gly Asp Asp Ser Leu Leu Trp Asn Lys Thr Ala Gly Ala Phe
                805                 810                 815

Ser Ala Ala His Gly Thr Asp Ala Thr Ser Lys Ile Thr Asn Val Lys
                820                 825                 830

Ala Gly Asp Leu Thr Ala Gly Ser Thr Asp Ala Val Asn Gly Ser Gln
            835                 840                 845

Leu Lys Thr Thr Asn Asp Asn Val Ser Thr Asn Thr Thr Asn Ile Thr
    850                 855                 860

Asn Leu Thr Asp Ser Val Gly Asp Leu Lys Asp Asp Ser Leu Leu Trp
865                 870                 875                 880

Asn Lys Ala Ala Gly Ala Phe Ser Ala Ala His Gly Thr Glu Ala Thr
                885                 890                 895

Ser Lys Ile Thr Asn Leu Leu Ala Gly Lys Ile Ser Ser Asn Ser Thr
            900                 905                 910

Asp Ala Ile Asn Gly Ser Gln Leu Tyr Gly Val Ala Asp Ser Phe Thr
            915                 920                 925

Ser Tyr Leu Gly Gly Gly Ala Asp Ile Ser Asp Thr Gly Val Leu Ser
930                 935                 940

Gly Pro Thr Tyr Thr Ile Gly Gly Thr Asp Tyr Thr Asn Val Gly Asp
945                 950                 955                 960

Ala Leu Ala Ala Ile Asn Thr Ser Phe Ser Thr Ser Leu Gly Asp Ala
                965                 970                 975

Leu Leu Trp Asp Ala Thr Ala Gly Lys Phe Ser Ala Lys His Gly Ile
            980                 985                 990

Asn Asn Ala Pro Ser Val Ile Thr Asp Val Ala Asn Gly Ala Val Ser
    995                 1000                1005

Ser Thr Ser Ser Asp Ala Ile Asn Gly Ser Gln Leu Tyr Gly Val Ser
    1010                1015                1020

Asp Tyr Ile Ala Asp Ala Leu Gly Gly Asn Ala Val Val Asn Thr Asp
1025                1030                1035                1040

Gly Ser Ile Thr Thr Pro Thr Tyr Ala Ile Ala Gly Gly Ser Tyr Asn
            1045                1050                1055

Asn Val Gly Asp Ala Leu Glu Ala Ile Asp Thr Thr Leu Asp Asp Ala
            1060                1065                1070

Leu Leu Trp Asp Thr Thr Ala Asn Gly Gly Asn Gly Ala Phe Ser Ala
    1075                1080                1085

Ala His Gly Lys Asp Lys Thr Ala Ser Val Ile Thr Asn Val Ala Asn
        1090                1095                1100

Gly Ala Val Ser Ala Thr Ser Asn Asp Ala Ile Asn Gly Ser Gln Leu
1105                1110                1115                1120

Tyr Ser Thr Asn Lys Tyr Ile Ala Asp Ala Leu Gly Gly Asp Ala Glu
```

-continued

```
                1125                1130                1135
Val Asn Ala Asp Gly Thr Ile Thr Ala Pro Thr Tyr Thr Ile Ala Asn
            1140                1145                1150

Thr Asp Tyr Asn Asn Val Gly Glu Ala Leu Asp Ala Leu Asp Asn Asn
            1155                1160                1165

Ala Leu Leu Trp Asp Glu Asp Ala Gly Ala Tyr Asn Ala Ser His Asp
        1170                1175                1180

Gly Asn Ala Ser Lys Ile Thr Asn Val Ala Ala Gly Asp Leu Ser Thr
1185                1190                1195                1200

Thr Ser Thr Asp Ala Val Asn Gly Ser Gln Leu Asn Ala Thr Asn Ile
            1205                1210                1215

Leu Val Thr Gln Asn Ser Gln Met Ile Asn Gln Leu Ala Gly Asn Thr
        1220                1225                1230

Ser Glu Thr Tyr Ile Glu Glu Asn Gly Ala Gly Ile Asn Tyr Val Arg
        1235                1240                1245

Thr Asn Asp Ser Gly Leu Ala Phe Asn Asp Ala Ser Ala Ser Gly Ile
        1250                1255                1260

Gly Ala Thr Ala Val Gly Tyr Asn Ala Val Ala Ser His Ala Ser Ser
1265                1270                1275                1280

Val Ala Ile Gly Gln Asp Ser Ile Ser Glu Val Asp Thr Gly Ile Ala
            1285                1290                1295

Leu Gly Ser Ser Ser Val Ser Ser Arg Val Ile Val Lys Gly Thr Arg
        1300                1305                1310

Asn Thr Ser Val Ser Glu Glu Gly Val Val Ile Gly Tyr Asp Thr Thr
        1315                1320                1325

Asp Gly Glu Leu Leu Gly Ala Leu Ser Ile Gly Asp Asp Gly Lys Tyr
        1330                1335                1340

Arg Gln Ile Ile Asn Val Ala Asp Gly Ser Glu Ala His Asp Ala Val
1345                1350                1355                1360

Thr Val Arg Gln Leu Gln Asn Ala Ile Gly Ala Val Ala Thr Thr Pro
            1365                1370                1375

Thr Lys Tyr Tyr His Ala Asn Ser Thr Ala Glu Asp Ser Leu Ala Val
        1380                1385                1390

Gly Glu Asp Ser Leu Ala Met Gly Ala Lys Thr Ile Val Asn Gly Asn
        1395                1400                1405

Ala Gly Ile Gly Ile Gly Leu Asn Thr Leu Val Leu Ala Asp Ala Ile
        1410                1415                1420

Asn Gly Ile Ala Ile Gly Ser Asn Ala Arg Ala Asn His Ala Asp Ser
1425                1430                1435                1440

Ile Ala Met Gly Asn Gly Ser Gln Thr Thr Arg Gly Ala Gln Thr Asn
            1445                1450                1455

Tyr Thr Ala Tyr Asn Met Asp Ala Pro Gln Asn Ser Val Gly Glu Phe
        1460                1465                1470

Ser Val Gly Ser Glu Asp Gly Gln Arg Gln Ile Thr Asn Val Ala Ala
        1475                1480                1485

Gly Ser Ala Asp Thr Asp Ala Val Asn Val Gly Gln Leu Lys Val Thr
        1490                1495                1500

Asp Ala Gln Val Ser Gln Asn Thr Gln Ser Ile Thr Asn Leu Asn Thr
1505                1510                1515                1520

Gln Val Thr Asn Leu Asp Thr Arg Val Thr Asn Ile Glu Asn Gly Ile
            1525                1530                1535

Gly Asp Ile Val Thr Thr Gly Ser Thr Lys Tyr Phe Lys Thr Asn Thr
        1540                1545                1550
```

-continued

```
Asp Gly Ala Asp Ala Asn Ala Gln Gly Lys Asp Ser Val Ala Ile Gly
            1555                1560                1565

Ser Gly Ser Ile Ala Ala Ala Asp Asn Ser Val Ala Leu Gly Thr Gly
        1570                1575                1580

Ser Val Ala Asp Glu Glu Asn Thr Ile Ser Val Gly Ser Ser Thr Asn
1585                1590                1595                1600

Gln Arg Arg Ile Thr Asn Val Ala Ala Gly Val Asn Ala Thr Asp Ala
                1605                1610                1615

Val Asn Val Ser Gln Leu Lys Ser Ser Glu Ala Gly Val Arg Tyr
            1620                1625                1630

Asp Thr Lys Ala Asp Gly Ser Ile Asp Tyr Ser Asn Ile Thr Leu Gly
        1635                1640                1645

Gly Gly Asn Ser Gly Thr Thr Arg Ile Ser Asn Val Ser Ala Gly Val
    1650                1655                1660

Asn Asn Asn Asp Ala Val Asn Tyr Ala Gln Leu Lys Gln Ser Val Gln
1665                1670                1675                1680

Glu Thr Lys Gln Tyr Thr Asp Gln Arg Met Val Glu Met Asp Asn Lys
                1685                1690                1695

Leu Ser Lys Thr Glu Ser Lys Leu Ser Gly Gly Ile Ala Ser Ala Met
            1700                1705                1710

Ala Met Thr Gly Leu Pro Gln Ala Tyr Thr Pro Gly Ala Ser Met Ala
        1715                1720                1725

Ser Ile Gly Gly Gly Thr Tyr Asn Gly Glu Ser Ala Val Ala Leu Gly
    1730                1735                1740

Val Ser Met Val Ser Ala Asn Gly Arg Trp Val Tyr Lys Leu Gln Gly
1745                1750                1755                1760

Ser Thr Asn Ser Gln Gly Glu Tyr Ser Ala Ala Leu Gly Ala Gly Ile
                1765                1770                1775

Gln Trp

<210> SEQ ID NO 52
<211> LENGTH: 990
<212> TYPE: PRT
<213> ORGANISM: Shigella flexneri

<400> SEQUENCE: 52

Met Thr Asn Leu Gly Glu Asp Ala Leu Lys Trp Asp Lys Asp Asn Gly
1               5                   10                  15

Val Phe Thr Ala Ala His Gly Thr Glu Thr Thr Ser Lys Ile Thr Asn
            20                  25                  30

Val Lys Asp Gly Asp Leu Thr Thr Gly Ser Thr Asp Ala Val Asn Gly
        35                  40                  45

Ser Gln Leu Lys Thr Thr Asn Asp Ala Val Ala Thr Asn Thr Thr Asn
    50                  55                  60

Ile Ala Thr Asn Thr Thr Asn Ile Ser Asn Leu Thr Glu Thr Val Thr
65                  70                  75                  80

Asn Leu Gly Glu Asp Ala Leu Lys Trp Asp Lys Asp Asn Gly Val Phe
                85                  90                  95

Thr Ala Ala His Gly Asn Asn Thr Ala Ser Lys Ile Thr Asn Ile Leu
            100                 105                 110

Asp Gly Thr Val Thr Ala Thr Ser Ser Asp Ala Ile Asn Gly Ser Gln
        115                 120                 125

Leu Tyr Asp Leu Ser Ser Asn Ile Ala Thr Tyr Phe Gly Gly Asn Ala
    130                 135                 140

Ser Val Asn Thr Asp Gly Val Phe Thr Gly Pro Thr Tyr Lys Ile Gly
```

```
            145                 150                 155                 160
Glu Thr Asn Tyr Tyr Asn Val Gly Asp Ala Leu Ala Ala Ile Asn Ser
                165                 170                 175

Ser Phe Ser Thr Ser Leu Gly Asp Ala Leu Leu Trp Asp Ala Thr Ala
            180                 185                 190

Gly Lys Phe Ser Ala Lys His Gly Thr Asn Gly Asp Ala Ser Val Ile
            195                 200                 205

Thr Asp Val Ala Asp Gly Glu Ile Ser Asp Ser Ser Asp Ala Val
210                 215                 220

Asn Gly Ser Gln Leu His Gly Val Ser Ser Tyr Val Val Asp Ala Leu
225                 230                 235                 240

Gly Gly Gly Ala Glu Val Asn Ala Asp Gly Thr Ile Thr Ala Pro Thr
            245                 250                 255

Tyr Thr Ile Ala Asn Ala Asp Tyr Asp Asn Val Gly Asp Ala Leu Asn
            260                 265                 270

Ala Ile Asp Thr Thr Pro Asp Asp Ala Leu Leu Trp Asp Ala Asp Ala
            275                 280                 285

Gly Glu Asn Gly Ala Phe Ser Ala Ala His Gly Lys Asp Lys Thr Ala
            290                 295                 300

Ser Val Ile Thr Asn Val Ala Asn Gly Ala Ile Ser Ala Ala Ser Ser
305                 310                 315                 320

Asp Ala Ile Asn Gly Ser Gln Leu Tyr Thr Thr Asn Lys Tyr Ile Ala
                325                 330                 335

Asp Ala Leu Gly Gly Asp Ala Glu Val Asn Ala Asp Gly Thr Ile Thr
            340                 345                 350

Ala Pro Thr Tyr Thr Ile Ala Asn Ala Glu Tyr Asn Asn Val Gly Asp
            355                 360                 365

Ala Leu Asp Ala Leu Asp Asp Asn Ala Leu Leu Trp Asp Lys Thr Ala
            370                 375                 380

Asn Gly Gly Ala Gly Ala Tyr Asn Ala Ser His Asp Gly Lys Ala Ser
385                 390                 395                 400

Ile Ile Thr Asn Val Ala Asn Gly Ser Ile Ser Glu Asp Ser Thr Asp
                405                 410                 415

Ala Val Asn Gly Ser Gln Leu Asn Ala Thr Asn Met Met Ile Glu Gln
            420                 425                 430

Asn Thr Gln Ile Ile Asn Gln Leu Ala Gly Asn Thr Asp Ala Thr Tyr
                435                 440                 445

Ile Glu Glu Asn Gly Ala Gly Ile Asn Tyr Val Arg Thr Asn Asp Asn
            450                 455                 460

Asp Leu Ala Phe Asn Asp Ala Ser Ala Ser Gly Val Gly Ala Thr Ala
465                 470                 475                 480

Val Gly Tyr Asn Ala Val Ala Ser Gly Ala Ser Ser Val Ala Ile Gly
            485                 490                 495

Gln Asn Ser Ser Ser Thr Val Asp Thr Gly Ile Ala Leu Gly Ser Ser
                500                 505                 510

Ser Val Ser Ser Arg Val Ile Ala Lys Gly Ser Arg Asp Thr Ser Val
            515                 520                 525

Thr Glu Asn Gly Val Val Ile Gly Tyr Asp Thr Thr Asp Gly Glu Leu
            530                 535                 540

Leu Gly Ala Leu Ser Ile Gly Asp Asp Gly Lys Tyr Arg Gln Ile Ile
545                 550                 555                 560

Asn Val Ala Asp Gly Ser Glu Ala His Asp Ala Val Thr Val Arg Gln
                565                 570                 575
```

```
Leu Gln Asn Ala Ile Gly Ala Val Ala Thr Thr Pro Thr Lys Tyr Phe
            580                 585                 590

His Ala Asn Ser Thr Ala Glu Asp Ser Leu Ala Val Gly Glu Asp Ser
            595                 600                 605

Leu Ala Met Gly Ala Lys Thr Val Val Asn Gly Asn Ala Gly Ile Gly
            610                 615                 620

Ile Gly Leu Asn Thr Leu Val Leu Ala Asp Ala Ile Asn Gly Ile Ala
625                 630                 635                 640

Ile Gly Ser Asn Ala Arg Ala Asn His Ala Asn Ser Ile Ala Met Gly
                645                 650                 655

Asn Gly Ser Gln Thr Thr Arg Gly Ala Gln Thr Gly Tyr Thr Ala Tyr
            660                 665                 670

Asn Met Asp Ala Pro Gln Asn Ser Val Gly Glu Phe Ser Val Gly Ser
            675                 680                 685

Glu Asp Gly Gln Arg Gln Ile Thr Asn Val Ala Ala Gly Ser Ala Asp
            690                 695                 700

Thr Asp Ala Val Asn Val Gly Gln Leu Lys Val Thr Asp Glu Arg Val
705                 710                 715                 720

Ala Gln Asn Thr Gln Ser Ile Thr Asn Leu Asn Asn Gln Val Thr Asn
                725                 730                 735

Leu Asp Thr Arg Val Thr Asn Ile Glu Asn Gly Ile Gly Asp Ile Val
            740                 745                 750

Thr Thr Gly Ser Thr Lys Tyr Phe Lys Thr Asn Thr Asp Gly Val Asp
            755                 760                 765

Ala Asn Ala Gln Gly Lys Asp Ser Val Ala Ile Gly Ser Gly Ser Ile
770                 775                 780

Ala Ala Ala Asp Asn Ser Val Ala Leu Gly Thr Gly Ser Val Ala Glu
785                 790                 795                 800

Glu Glu Asn Thr Ile Ser Val Gly Ser Ser Thr Asn Gln Arg Arg Ile
            805                 810                 815

Thr Asn Val Ala Ala Ser Val Asn Ala Thr Asp Ala Val Asn Val Ser
            820                 825                 830

Gln Leu Lys Ser Ser Glu Ala Gly Gly Val Arg Tyr Asp Thr Lys Ala
            835                 840                 845

Asp Gly Ser Ile Asp Tyr Ser Asn Ile Thr Leu Gly Gly Gly Asn Gly
850                 855                 860

Ser Thr Thr Arg Ile Ser Asn Val Ser Ala Gly Val Asn Asn Asn Asp
865                 870                 875                 880

Ala Val Asn Tyr Ala Gln Leu Lys Gln Ser Ala Gln Glu Thr Lys Gln
            885                 890                 895

Tyr Thr Asp Gln Arg Met Val Glu Met Asp Asn Lys Leu Ser Lys Thr
            900                 905                 910

Glu Ser Lys Leu Ser Gly Gly Ile Ala Ser Ala Met Ala Met Thr Gly
            915                 920                 925

Leu Pro Gln Ala Tyr Thr Pro Gly Ala Ser Met Ala Ser Ile Gly Gly
            930                 935                 940

Gly Thr Tyr Asn Gly Glu Ser Ala Val Ala Leu Gly Val Ser Met Val
945                 950                 955                 960

Ser Ala Asn Gly Arg Trp Val Tyr Lys Leu Gln Gly Ser Thr Asn Ser
                965                 970                 975

Gln Gly Glu Tyr Ser Ala Ala Leu Gly Ala Gly Ile Gln Trp
            980                 985                 990

<210> SEQ ID NO 53
```

<211> LENGTH: 227
<212> TYPE: PRT
<213> ORGANISM: Brucella melitensis

<400> SEQUENCE: 53

```
Met Ser Phe Phe Lys Lys Asn Ile Ser Ile Thr Ala Met Gly Gly Leu
1               5                   10                  15

Met Leu Ser Leu Ala Val Asp Ala Ala Lys Ala Glu Glu Asn Val Ser
            20                  25                  30

Gln Val Lys Leu Pro Pro Val Phe Val Phe Glu Leu Val Glu Asn Gln
        35                  40                  45

Gly Leu Ala Asn Ile Ala Leu Ile Arg Pro Arg Val Ile Ala Pro Asp
    50                  55                  60

Asn Asn Leu Arg Pro Gly Gly Ile Val Ser Gly Ile Ala Gly Leu Leu
65                  70                  75                  80

Thr Leu Gly Gln Glu Asn Arg Asn Leu Ile Ser Glu Asn Arg Gln Val
                85                  90                  95

Ile Asn Asn Asn Thr Thr Ala Ile Gly Gln Asn Arg Thr Ser Ile Ser
            100                 105                 110

Thr Asn Ala Lys Gly Val Ala Asp Asn Arg Ala Ala Ile Arg Gln Asn
        115                 120                 125

Ser Ala Ala Ile Ser Ala Leu Gly Gln Arg Val Asp Gly Leu Gln Gly
    130                 135                 140

Gln Ile Asn Ser Ala Arg Lys Glu Ala Arg Ala Gly Ala Ala Asn Ala
145                 150                 155                 160

Ala Ala Leu Ser Gly Leu Arg Tyr Asp Asn Arg Pro Gly Lys Val Ser
                165                 170                 175

Ile Ala Thr Gly Val Gly Gly Phe Lys Gly Ser Thr Ala Leu Ala Ala
            180                 185                 190

Gly Ile Gly Tyr Thr Ser Lys Asn Glu Asn Ala Arg Tyr Asn Val Ser
        195                 200                 205

Val Ala Tyr Asn Glu Ala Gly Thr Ser Trp Asn Ala Gly Ala Ser Phe
    210                 215                 220

Thr Leu Asn
225
```

<210> SEQ ID NO 54
<211> LENGTH: 311
<212> TYPE: PRT
<213> ORGANISM: Brucella suis

<400> SEQUENCE: 54

```
Met Ser Phe Phe Lys Lys Asn Ile Ser Ile Thr Ala Met Gly Gly Leu
1               5                   10                  15

Met Leu Ser Leu Ala Val Asp Ala Ala Lys Ala Glu Glu Asn Val Ser
            20                  25                  30

Gln Val Lys Leu Pro Pro Val Phe Val Phe Glu Leu Val Glu Asn Gln
        35                  40                  45

Gly Leu Ala Asn Ile Ala Leu Ile Arg Pro Arg Val Ile Ala Pro Asp
    50                  55                  60

Asn Asn Leu Arg Pro Gly Gly Ile Val Ser Gly Ile Ala Gly Leu Leu
65                  70                  75                  80

Thr Leu Gly Gln Glu Asn Arg Asn Leu Ile Ser Glu Asn Arg Gln Val
                85                  90                  95

Ile Asn Asn Asn Thr Thr Ala Ile Gly Gln Asn Ser Arg Ile Asp
            100                 105                 110
```

```
Ala Asn Ala Lys Gly Val Ala Asp Asn Arg Ala Ala Ile Gly Gln Asn
        115                 120                 125

Ser Gly Arg Ile Asp Ala Asn Ala Lys Gly Val Ala Asp Asn Lys Ala
    130                 135                 140

Ala Ile Gly Arg Asn Ser Gly Arg Ile Asp Ala Asn Ala Lys Gly Val
145                 150                 155                 160

Ala Asp Asn Lys Thr Ala Ile Gly Arg Asn Ser Gly Arg Ile Asp Thr
                165                 170                 175

Asn Ala Lys Gly Val Ala Asp Asn Arg Ala Ala Ile Ser Gln Asn Arg
            180                 185                 190

Gly Arg Ile Asn Ala Asn Ala Ala Gly Val Ala Ser Asn Arg Ala Ala
        195                 200                 205

Ile Arg Gln Asn Ser Ala Ala Ile Ser Ala Leu Gly Gln Arg Val Asp
    210                 215                 220

Gly Leu Gln Gly Gln Ile Asn Ser Ala Arg Lys Glu Ala Arg Ala Gly
225                 230                 235                 240

Ala Ala Asn Ala Ala Ala Leu Ser Gly Leu Arg Tyr Asp Asn Arg Pro
                245                 250                 255

Gly Lys Val Ser Ile Ala Thr Gly Val Gly Gly Phe Lys Gly Ser Thr
            260                 265                 270

Ala Leu Ala Ala Gly Ile Gly Tyr Thr Ser Lys Asn Glu Asn Ala Arg
        275                 280                 285

Tyr Asn Val Ser Val Ala Tyr Asn Glu Ala Gly Thr Ser Trp Asn Ala
    290                 295                 300

Gly Ala Ser Phe Thr Leu Asn
305                 310

<210> SEQ ID NO 55
<211> LENGTH: 1309
<212> TYPE: PRT
<213> ORGANISM: Ralstonia solanacearum

<400> SEQUENCE: 55

Met Val Phe Ser Ala Met Pro Gln Tyr Ala Cys Ala Glu Met Leu Leu
1               5                   10                  15

Gln Asn Asp Pro Gly Thr Asn Cys Gly Ser Val Gly Asp Ala Tyr Ala
            20                  25                  30

Trp Ala Arg Gly Asp Gly Tyr Ser Gly Cys Lys Val Gly Tyr Glu Ala
        35                  40                  45

Ala Lys Asn Leu Ala Lys Gly Thr Ala Phe Gly Asn Ser Leu Gly Gln
    50                  55                  60

Leu Ser Pro Gly Thr Asn Ile Leu Val Tyr Gly Ser Thr Leu Arg Ala
65                  70                  75                  80

Gly Met Asn Asp Glu Val Thr Pro Leu Asp Ser Met Asn Ile Gly Gly
                85                  90                  95

His Leu Asp Val Trp Gly Ala Ser Gly Phe His Gly Gly Val Asp Met
            100                 105                 110

Asn Asn Ser Ala Ile Lys Asn Leu Ala Asp Gly Thr Leu Ser Ala Thr
        115                 120                 125

Ser Thr Glu Ala Val Thr Gly Arg Gln Leu Asn Ala Thr Asn Thr Asn
    130                 135                 140

Ile Thr Asn Leu Gln Asn Ser Ile Lys Ser Ile Ser Ser Ser Ala Ser
145                 150                 155                 160

Leu Val Gln Gln Ser Ala Ala Gly Lys Asp Ile Thr Val Ala Lys Asp
                165                 170                 175
```

```
Leu Asp Gly Asp Ala Val Asp Phe Ser Gly Lys Lys Leu Ser Asp Ser
            180                 185                 190

Thr Thr Phe Ser Arg Lys Leu Thr Gly Val Ala Glu Gly Thr Leu Ser
        195                 200                 205

Ala Thr Ser Thr Asp Ala Val Ser Gly Lys Gln Leu Tyr Thr Thr Asn
        210                 215                 220

Gln Asn Leu Ser Thr Thr Asn Gln Asn Leu Ala Asp Thr Asn Lys Ser
225                 230                 235                 240

Leu Ala Glu Thr Asn Lys Asn Val Ser Ala Thr Thr Asn Ile Thr
                245                 250                 255

Asn Leu Gln Asn Thr Ile Lys Asn Ile Ser Gly Gly Ser Ala Gly Leu
            260                 265                 270

Val Gln Gln Ser Ala Ala Gly Lys Asp Ile Thr Val Ala Lys Asp Leu
        275                 280                 285

Asp Gly Glu Ala Val Asp Phe Ser Gly Lys Lys Leu Ser Asp Ser Thr
        290                 295                 300

Thr Phe Ser Arg Lys Leu Thr Gly Val Ala Glu Gly Thr Leu Ser Ala
305                 310                 315                 320

Thr Ser Thr Asp Ala Val Ser Gly Lys Gln Leu Tyr Thr Thr Asn Gln
                325                 330                 335

Asn Leu Ala Ser Thr Asn Lys Asp Leu Ala Asn Thr Asn Thr Arg Leu
            340                 345                 350

Thr Thr Ala Glu Gly Asn Leu Ser Ser Asn Thr Thr Ser Ile Thr Asn
        355                 360                 365

Leu Gln Asn Thr Ile Lys Asn Ile Ser Gly Gly Ser Ala Gly Leu Val
        370                 375                 380

Gln Gln Ser Ala Ala Gly Lys Asp Ile Thr Val Ala Lys Asp Leu Asp
385                 390                 395                 400

Gly Asp Ala Val Asp Phe Ser Gly Lys Lys Leu Ser Asp Ser Thr Thr
                405                 410                 415

Phe Ser Arg Lys Leu Thr Gly Val Ala Glu Gly Thr Leu Ser Ala Thr
            420                 425                 430

Ser Thr Asp Ala Val Ser Gly Arg Gln Leu Tyr Thr Thr Asn Gln Asn
        435                 440                 445

Leu Ser Thr Thr Asn Gln Asn Leu Ala Asp Thr Asn Lys Ser Leu Ala
        450                 455                 460

Glu Thr Asn Lys Asn Val Ser Ala Thr Thr Asn Ile Thr Asn Leu
465                 470                 475                 480

Gln Asn Thr Val Asn Asn Ile Ser Ser Gly Ser Ala Gly Leu Val Gln
                485                 490                 495

Gln Ser Ala Ala Gly Lys Asp Ile Thr Val Ala Lys Asp Leu Asp Gly
            500                 505                 510

Asp Ala Val Asp Phe Ser Gly Lys Lys Leu Ser Asp Ser Thr Thr Phe
        515                 520                 525

Ser Arg Lys Leu Thr Gly Val Ala Glu Gly Thr Leu Ser Ala Thr Ser
        530                 535                 540

Thr Asp Ala Val Ser Gly Lys Gln Leu Tyr Thr Thr Asn Gln Asn Leu
545                 550                 555                 560

Ser Thr Thr Asn Gln Asn Leu Ala Asp Thr Asn Lys Ser Leu Ala Glu
                565                 570                 575

Thr Asn Lys Asn Val Ser Ala Thr Thr Thr Asn Ile Thr Asn Leu Gln
            580                 585                 590

Asn Thr Val Asn Asn Ile Ser Ser Gly Ser Ala Gly Leu Val Gln Gln
        595                 600                 605
```

```
Ser Ala Ala Gly Lys Asp Ile Thr Val Ala Lys Asn Leu Asp Gly Asp
    610                 615                 620
Ala Val Asp Phe Ser Gly Lys Lys Leu Ser Asp Ser Thr Thr Phe Ser
625                 630                 635                 640
Arg Lys Leu Thr Gly Val Ala Glu Gly Thr Leu Ser Ala Thr Ser Thr
                645                 650                 655
Asp Ala Val Ser Gly Lys Gln Leu Tyr Thr Thr Asn Gln Asn Leu Ala
                660                 665                 670
Ser Thr Asn Lys Asp Leu Ala Asn Thr Asn Thr Arg Leu Thr Thr Ala
            675                 680                 685
Glu Gly Asn Leu Ser Ser Asn Thr Thr Ser Ile Thr Asn Leu Gln Asn
    690                 695                 700
Thr Ile Lys Asn Ile Ser Gly Gly Ser Ala Gly Leu Val Gln Gln Ser
705                 710                 715                 720
Ala Ala Gly Lys Asp Ile Thr Val Ala Lys Asp Leu Asp Gly Asp Ala
                725                 730                 735
Val Asp Phe Ser Gly Lys Asn Leu Ser Asp Ser Thr Thr Phe Ser Arg
                740                 745                 750
Lys Leu Thr Gly Val Ala Glu Gly Thr Leu Ser Ala Thr Ser Thr Asp
            755                 760                 765
Ala Val Ser Gly Lys Gln Leu Tyr Thr Thr Asn Gln Asn Leu Ser Thr
    770                 775                 780
Thr Asn Gln Asn Leu Ala Asp Thr Asn Lys Ser Leu Ala Lys Thr Asn
785                 790                 795                 800
Asn Asn Val Ser Ala Thr Thr Asn Ile Thr Asn Leu Gln Asn Thr
                805                 810                 815
Val Asn Asn Ile Ser Ser Gly Ser Ala Gly Leu Val Gln Gln Ser Ala
            820                 825                 830
Ala Gly Lys Asp Ile Thr Val Ala Lys Asp Leu Asp Gly Asp Ala Val
    835                 840                 845
Asp Phe Ser Gly Lys Lys Leu Ser Asp Ser Thr Thr Phe Ser Arg Lys
850                 855                 860
Leu Thr Gly Val Ala Glu Gly Thr Leu Ser Ala Thr Ser Thr Asp Ala
865                 870                 875                 880
Val Ser Gly Lys Gln Leu Tyr Ala Thr Asn Gln Asn Val Ser Lys Leu
                885                 890                 895
Ser Ala Asn Val Thr Asp Val Ser Asp Ser Val Thr Asn Ile Lys Asn
            900                 905                 910
Thr Met Asn Thr Ile Val Asn Gly Gly Gly Leu Lys Tyr Phe His Ala
    915                 920                 925
Asn Ser Thr Leu Asp Asp Ala Gln Ala Met Gly Leu Glu Ser Ile Ala
    930                 935                 940
Phe Gly Gly Ala Ala Val Ala Ala Gly Met Asn Ser Met Ala Met Gly
945                 950                 955                 960
Gly Asn Ala Arg Ala Val Ala Gly Asn Ala Val Ala Leu Gly Ala Gly
                965                 970                 975
Ser Val Ala Asp Arg Ala Asn Thr Val Ser Val Gly Ser Ala Gly Lys
            980                 985                 990
Glu Arg Gln Ile Thr Asn Val Ala Ala Gly Thr Ala Asp Thr Asp Ala
        995                 1000                1005
Val Asn Val Ala Gln Leu Lys Ala Ala Gly Ile Ile Asn Gly Ser Gly
        1010                1015                1020
Arg Thr Asn Ala Thr Val Thr Tyr Gly Thr Asn Ala Asp Gly Ser Ala
```

```
              1025                1030                1035                1040
Asp Tyr Gly Asn Val Thr Leu Gly Gly Gly Asn Ala Pro Ala Gly Thr
                1045                1050                1055

Ala Ile His Asn Val Ala Ala Gly Thr Ala Glu Thr Asp Ala Val Asn
                1060                1065                1070

Val Arg Gln Met Asn Ala Ala Ile Ala Ser Val Gln Lys Val Ser Asn
                1075                1080                1085

Thr Asn Asp Pro Met Phe Ala Ala Asp Gly Asp Arg Ala Val Lys Arg
                1090                1095                1100

Ala Ser Ala Lys Gly Thr His Ala Thr Ala Met Gly Ala Ala Ala Ser
1105                1110                1115                1120

Ala Gly Gly Asp Gln Ser Val Ala Thr Gly His Asn Ala Gln Ser Gly
                1125                1130                1135

Gly Asp Ser Ser Val Ala Met Gly Ala Asn Ala Lys Ala Thr Ala Asn
                1140                1145                1150

His Ala Val Ala Val Gly Ser Gly Ser Val Ala Asn Arg Ala Asn Thr
                1155                1160                1165

Met Ser Val Gly Ser Ala Gly Ser Glu Arg Gln Ile Thr Asn Val Ala
                1170                1175                1180

Ala Gly Val Gln Gly Thr Asp Ala Val Asn Val Ser Gln Leu Ser Gln
1185                1190                1195                1200

Ala Val Tyr Ala Ala Val Gly Asp Leu Pro Ala Gly Thr Ala Arg
                1205                1210                1215

Gln Tyr Thr Asp Glu Gln Ile Gly Met Val Arg Gln Gly Ile Ser Gln
                1220                1225                1230

Val Ala Arg Gly Ala Tyr Ser Gly Ile Ala Ala Thr Ala Leu Thr
                1235                1240                1245

Met Ile Pro Asp Val Asp Gln Gly Lys Ser Ile Ala Ile Gly Ile Gly
                1250                1255                1260

Ser Ala Thr Tyr Lys Gly Tyr Gln Ala Val Ala Leu Gly Ala Ser Ala
1265                1270                1275                1280

Arg Ile Ser His Asn Leu Lys Ala Lys Met Gly Val Gly Tyr Ser Ser
                1285                1290                1295

Glu Gly Thr Thr Val Gly Met Gly Ala Ser Tyr Gln Trp
                1300                1305

<210> SEQ ID NO 56
<211> LENGTH: 1291
<212> TYPE: PRT
<213> ORGANISM: Sinorhizobium meliloti

<400> SEQUENCE: 56

Met Ala Leu Gly Arg Gln Ser Val Ser Ala Gly Ser Gly Ser Leu Ala
1               5                   10                  15

Phe Gly Asn Gly Ser Tyr Ala Asn Ser Asn Gly Ser Val Ala Ile Gly
                20                  25                  30

Gln Ser Ala Tyr Ala Ala Asn Val Arg Ala Ile Ala Ile Gly Gly Asp
            35                  40                  45

Asp Ala Phe Ala Trp Arg Glu Ala Glu Gln Thr Lys Ala Gly Gly Ser
        50                  55                  60

Gln Ser Ile Ala Met Gly Val Arg Ala Arg Thr Lys Ser Leu Val Val
65                  70                  75                  80

Asp Asp Pro Asp Thr Val Ala Asn Glu Ala Asp Pro Gly Gly Ala Ser
                85                  90                  95

Asp Ala Ile Ala Ile Gly Thr Asp Ala Gln Ala Asn Gly Asp Arg Ser
```

```
                 100                 105                 110
Leu Ala Ile Gly Arg Gln Asn Gln Ala Gly Asn Glu Gln Ser Ile Gly
            115                 120                 125
Ile Gly Ala Gly Asn Thr Ala Thr Gly Lys Leu Ser Ile Gly Ile Gly
        130                 135                 140
Ser Ser Asn Val Ala Ser Gly Glu Gln Ser Leu Ser Leu Gly Ala Gly
145                 150                 155                 160
Asn Asn Ala Leu Gly Gln Gly Ser Ile Ser Ile Gly Thr Glu Thr Thr
                165                 170                 175
Ala Gly Gly Leu Arg Ser Ile Ala Phe Gly Val Arg Ala Ser Thr Lys
            180                 185                 190
Glu Ala Asn Leu Asp Ile Pro Asp Val Ala Ala Ile Asp Ala Ile
        195                 200                 205
Ala Ile Gly Thr Asn Thr Lys Ala Asn Gly Asp Arg Ser Val Ser Ile
        210                 215                 220
Gly Thr Gly Ser Gln Ala Ser Ser Gly Ala Val Ser Ile Gly Asp Ala
225                 230                 235                 240
Ala Lys Ala Val Gly Asp Lys Ser Val Ser Ile Gly Thr Glu Ser Trp
            245                 250                 255
Ala Asp Gly Asp Glu Ser Val Ser Ile Gly Leu Val Asn Asn Ala Gly
        260                 265                 270
Phe Glu Gly Asn Asp Arg Ile Lys Gly Gly Gln Thr Ser Val Ser Leu
            275                 280                 285
Gly Ala Phe Asn Gln Ser Pro Gly Ile Glu Ala Ile Ala Ile Gly Ala
        290                 295                 300
Arg Asn Glu Ala Asn Ala Asp Arg Ser Ile Ala Ile Gly Ser Arg Ala
305                 310                 315                 320
Lys Thr Lys Ala Ala Asp Pro Ala Gln Ala Asp Gly Gly Ala Arg Asp
            325                 330                 335
Ala Val Ala Ile Gly Thr Asp Ala Leu Ala Asn Asp Asp Arg Ser Ile
        340                 345                 350
Ser Ile Gly Trp Asn Ser Ser Thr Ser Leu Asn Asp Ser Ile Ser Ile
        355                 360                 365
Gly Thr Arg Ala Thr Ser Gly Ser Ala Gly Asp Ile Met Ile Gly Thr
        370                 375                 380
Gly Ser Gly Thr Gly Ser Thr Ser Gly Gln Asn Asn Val Ala Leu Gly
385                 390                 395                 400
Val Ala Ala Ser Gln Lys Val Lys Gly Ser Ser Asn Ile Ala Ile Gly
            405                 410                 415
Asp Ser Ala Gly Gly Ser Arg Glu Gly Asp Asn Asn Val Ala Ile Gly
        420                 425                 430
Thr Asn Ala Gly Ile Gln Phe Ser Glu Ser Glu His Glu Thr Ala Val
        435                 440                 445
Arg Ala Asp Leu Val Val Ser Asp Ala Val Ser Ile Gly Asn Glu Ala
        450                 455                 460
Leu Ala Ser Ala Asp Glu Ala Ile Ala Ile Gly Thr Gly Ala Val Ala
465                 470                 475                 480
Ser Gly Leu Lys Ser Ile Ser Ile Gly Val Gly Asn Thr Val Ser Gly
            485                 490                 495
Ala Ser Ser Gly Ala Ile Gly Asp Pro Thr Asp Ile Thr Gly Thr Gly
        500                 505                 510
Ser Tyr Ser Leu Gly Asn Asp Asn Thr Ile Ala Ala Asp Asn Ala Gly
        515                 520                 525
```

```
Thr Phe Gly Asn Asp Asn Thr Leu Ala Asp Ala Ala Asp Gly Ser Arg
            530                 535                 540

Val Ile Gly Asn Gly Asn Ile Asp Val Ser Asp Ala Phe Val Leu
545                 550                 555                 560

Gly Asn Gly Ala Asp Val Thr Glu Val Gly Val Ala Leu Gly Ser
                565                 570                 575

Gly Ser Val Ser Asp Thr Gly Ala Asp Val Ala Gly Tyr Val Pro Gly
            580                 585                 590

Gly Ala Ser Thr Ala Asp Gln Asn Ala Ile Glu Ala Thr Gln Ser Thr
            595                 600                 605

Arg Gly Ala Val Ala Val Gly Asn Pro Asp Ala Glu Thr Gly Val Tyr
            610                 615                 620

Arg Gln Ile Thr Gly Val Ala Ala Gly Thr Ala Asp Ser Asp Ala Ala
625                 630                 635                 640

Asn Val Ala Gln Leu Lys Ser Val Glu Thr Ile Ala Lys Thr Gly Trp
                645                 650                 655

Lys Leu Thr Thr Asp Ser Gly Ser Ile Asp Gly Ile Gly Pro Gly Asp
            660                 665                 670

Glu Leu Val Leu Lys Gly Gly Asp Gly Asn Ile Val Ile Ser Asn Gln
            675                 680                 685

Ile Leu Ser Asn Asp Val Ser Ile Asp Leu Ala Asp Glu Ile Glu Val
            690                 695                 700

Asn Arg Val Thr Ala Arg Asp Pro Asp Thr Gly Ala Ser Thr Val Leu
705                 710                 715                 720

Asp Glu Asn Gly Leu Ser Phe Thr Thr Gln Ala Asn Gly Glu Asp
                725                 730                 735

Thr Ala Leu Gly Pro Arg Val Thr Ala Ala Gly Ile Gln Ala Ala Gly
                740                 745                 750

Lys Ile Thr Asn Val Ala Ala Gly Glu Ala Asp Thr Asp Ala Val Asn
            755                 760                 765

Phe Ser Gln Leu Arg Gln Val Glu Thr Ala Ser Gly Asn Thr Asp Gln
            770                 775                 780

Arg Ala Val Lys Tyr Asp Trp Thr Asp Ala Asn Thr Asn Gly Val Ile
785                 790                 795                 800

Asp Glu Gly Glu Leu Asn Leu Asp Ser Val Thr Leu Ala Gly Gly Met
                805                 810                 815

Gly Gly Thr Arg Ile Ser Asn Leu Ala Pro Gly Ala Leu Ser Ala Ala
            820                 825                 830

Ser Thr Asp Ala Val Asn Gly Ser Gln Leu Phe Gly Leu Arg Ser Arg
            835                 840                 845

Val Ser Asn Val Ala Val Ala Leu Gly Gly Gly Ala Ala Tyr Asp Pro
            850                 855                 860

Val Lys Asp Glu Trp Ile Ala Pro Lys Tyr Thr Ile Gly Gly Thr Asp
865                 870                 875                 880

Tyr Ser Asn Val Gly Asp Ala Leu Ala Ala Val Gly Gly Thr Ala Gly
                885                 890                 895

Ala Gly Trp Ser Leu Ser Ala Gln Gly Ala Asn Ala Ser Asn Val Ala
                900                 905                 910

Pro Gly Glu Thr Val Asp Leu Arg Ser Gly Asp Gly Asn Ile Val Val
            915                 920                 925

Ser Lys Ala Glu Thr Gly Asp Thr Val Ser Phe Asp Leu Ala Asp Asp
            930                 935                 940

Leu Asp Val Ser Glu Ser Ile Thr Val Gly Ala Asp Pro Ala Asp Pro
945                 950                 955                 960
```

Asn Ala Pro Thr Thr Val Ile Thr Gly Gly Ser Ile Val Ile Gly Ser
                965                 970                 975

Thr Met Leu Gly Ser Asn Gly Leu Val Ile Thr Gly Gly Pro Ser Val
            980                 985                 990

Thr Thr Asp Gly Ile Asp Ala Gly Gly Met Lys Val Thr Asn Val Ala
        995                 1000                1005

Asn Gly Thr Val Ala Lys Asp Ser Lys Asp Ala Val Asn Gly Gly Gln
    1010                1015                1020

Leu Phe Asp Val Val Ala Asn Ala Thr Ala Asn Gly Val Gly Tyr Asp
1025                1030                1035                1040

Asp Lys Ser Lys Gly Thr Leu Thr Leu Glu Gly Ala Asn Gly Thr Lys
                1045                1050                1055

Ile Thr Asn Val Ala Ala Gly Asp Leu Asn Ala Asn Ser Thr Asp Ala
            1060                1065                1070

Val Asn Gly Ser Gln Leu Tyr Ala Thr Asn Val Lys Val Asp Arg Leu
        1075                1080                1085

Asp Thr Glu Val Lys Glu Ile Asp Ser Arg Val Thr Tyr Ile Glu Ser
    1090                1095                1100

Phe Gln Gly Asp Leu Glu Asn Ala Ala Val Tyr Asp Thr Asp Ala Ala
1105                1110                1115                1120

Gly Lys Arg Leu Asn Thr Leu Thr Leu Glu Gly Gly Asp Pro Asp Lys
                1125                1130                1135

Pro Val Leu Ile Ala Asn Val Ala Lys Gly Val Lys Ala Thr Asp Ala
            1140                1145                1150

Val Asn Val Gly Gln Leu Asp Glu Ser Val Ala Glu Ser Lys Ser Tyr
        1155                1160                1165

Thr Asp Glu Lys Thr Glu Trp Ala Ile Asp Gln Ala Ala Ile Tyr Thr
    1170                1175                1180

Asp Gln Val Ile Glu Thr Lys Val Ser Ala Val Asn Asn Tyr Ala Gln
1185                1190                1195                1200

Gln Arg Phe Ala Gln Leu Ser Gly Glu Ile Gly Gln Val Arg Ser Glu
                1205                1210                1215

Ala Arg Gln Ala Ala Ala Ile Gly Leu Ala Ala Ala Ser Leu Arg Phe
            1220                1225                1230

Asp Asn Glu Pro Gly Lys Leu Ser Val Ala Leu Gly Gly Phe Trp
        1235                1240                1245

Arg Ser Glu Gly Ala Leu Ala Phe Gly Ala Gly Tyr Thr Ser Glu Asp
    1250                1255                1260

Gly Arg Val Arg Ala Asn Leu Thr Gly Ala Ala Ala Gly Gly Asn Val
1265                1270                1275                1280

Gly Val Gly Ala Gly Leu Ser Ile Thr Leu Asn
                1285                1290

<210> SEQ ID NO 57
<211> LENGTH: 372
<212> TYPE: PRT
<213> ORGANISM: Bradorhizobium japonicum

<400> SEQUENCE: 57

Met Arg Ala Phe Gly Ser Gly Asn Ala Ile Asn Gly Thr Asn Tyr Ala
1               5                   10                  15

Ala Val Gly Ser Asn Asn Val Ala Gly Asn Asn Gly Ala Val Val
            20                  25                  30

Gly Ser Gly Asn Gly Val Thr Gly Asp Asn Thr Ala Ala Phe Gly Ser
        35                  40                  45

```
Ser Ile Gly Ile Ala Gly Gly Asn Asn Ala Ala Val Gly Ser Phe Ser
    50                  55                  60

Thr Val Thr Gly Ser Asn Ser Ala Ala Val Gly Ser Phe Asn Asn Val
65                  70                  75                  80

Ser Gly Asn Asn Ser Gly Ala Phe Gly Thr Gly Gln Asn Ile Arg Gly
                85                  90                  95

Asn Gly Thr Phe Ala Ile Gly Asp Pro Asn Ile Val Asn Gly Asn Asn
            100                 105                 110

Ser Leu Val Phe Gly Asp Asn Asn Thr Val Asn Gly Ser Asn Val Ala
        115                 120                 125

Gly Arg Gly Asp Asn Ile Gln Leu Val Gly Ser Asn Asn Thr Ile Ala
    130                 135                 140

Ala Thr Ser Ser Ala Ala Gly Ser Ser Val Phe Gly Ser Gly Asn Thr
145                 150                 155                 160

Val Asn Ala Thr Asn Ala Val Val Met Gly Asn Asn Ser Thr Val Ser
                165                 170                 175

Gly Ala Ser Ser Val Ala Ile Gly Asn Gly Thr Ala Val Thr Gly Ile
            180                 185                 190

Asn Ala Ile Ala Met Gly Thr Gly Ala Gly Ala Asn Phe Asp Asn Ser
        195                 200                 205

Val Ala Ile Gly Ser Gly Ala Thr Thr Thr Arg Ala Asn Gln Val Ala
    210                 215                 220

Val Gly Thr Ala Ser Ser Thr Tyr Thr Met Ser Gly Ile Thr Ser Ala
225                 230                 235                 240

Ala Ser Lys Ala Ala Gln Ser Gly Pro Thr Gln Leu Val Thr Ser Asp
                245                 250                 255

Ala Ala Gly Asn Leu Ala Thr Thr Ser Leu Ala Gly Leu Gly Leu Ala
            260                 265                 270

Ser Ala Gly Asp Ile Asn Gly Ile Asn Ser Gln Leu Ala Ala Leu Asn
        275                 280                 285

Gly Arg Val Asp Asn Leu Thr Arg Glu Ser Arg Gly Gly Val Ala Leu
    290                 295                 300

Ala Leu Ala Ala Ser Ser Leu Gln Phe Asp Pro Arg Pro Gly Lys Ile
305                 310                 315                 320

Ser Val Ser Gly Gly Phe Gly Asn Phe Gln Gly Gln Ser Gly Leu Ala
                325                 330                 335

Val Gly Leu Gly Tyr Ser Tyr Ser Asp Ala Met Arg Phe Asn Ala Ala
            340                 345                 350

Phe Thr Ala Ala Gln Gln Gly Ala Ile Gly Val Arg Ala Gly Ala Ser
        355                 360                 365

Trp Thr Leu Asn
    370
```

<210> SEQ ID NO 58
<211> LENGTH: 3399
<212> TYPE: PRT
<213> ORGANISM: Burkholderia fungorum
<220> FEATURE:
<221> NAME/KEY: Xaa
<222> LOCATION: 787
<223> OTHER INFORMATION: Xaa is any amino acid

<400> SEQUENCE: 58

```
Met Asn Lys Thr Tyr Arg Ser Val Trp Asn Glu Ser Thr Gly Thr Trp
1               5                   10                  15

Val Ala Ala Ser Glu His Ala Ser Ala Arg Gly Lys Lys Ser Ser Ala
```

```
                 20                  25                  30
Lys Thr Ser Ser Thr Lys Ala Val Gly Ala Leu Gly Leu Ala Ala
             35                  40                  45
Gly Leu Tyr Gly Ala Asp Ala Phe Ala Leu Gly Gly Leu Thr Leu
         50                  55                  60
Cys Pro Thr Thr Glu Gly Ser Ala Gly Tyr Thr Ala Gly Ser Ala Ser
 65                  70                  75                  80
Ser Ala Asn Gly Ala Tyr Cys Gly Ser Asp Tyr Gln Trp Gly Leu Phe
                 85                  90                  95
Ser Asn Thr Asn Ala Asp Gly Ser Lys Ser Gly Gln Pro Ile Gly Ala
            100                 105                 110
Ala Ile Glu Gly Met Asn Asp Gly Ser Leu Leu Leu Tyr Gly Pro Asn
            115                 120                 125
Asn Ile Val Met Lys Asn Leu Val Ser Met Ser Ser Asn Lys Ile Ile
145             130                 135                 140
Asn Leu Ala Pro Gly Thr Val Ser Ser Thr Ser Ala Asp Ala Val Asn
145                 150                 155                 160
Gly Ser Gln Leu Tyr Ala Thr Asn Gln Asn Val Ser Asn Ile Gly Asn
                165                 170                 175
Thr Val Asn Asn Ile Thr Thr Gly Ala Gly Ile Met Tyr Phe His Val
            180                 185                 190
Asn Ser Thr Leu Ala Asp Ser Thr Ala Asn Gly Val Asn Ser Ile Ala
            195                 200                 205
Ile Gly Gly Ala Thr Arg Thr Asp Ala Asn Asn Ser Ile Ser Ile Gly
    210                 215                 220
Thr Gly Leu Thr Gln Ala Ser Ser Asn Thr Gly Ala Ile Ala Ile Gly
225                 230                 235                 240
Gln Asn Ala Ser Ile Asn Val Tyr Gly Ala Asn Ser Ile Ala Ile Gly
                245                 250                 255
Thr Asn Ser Ala Thr Gly Gly Ile Gly Gly Ala Ile Ala Leu Gly Glu
            260                 265                 270
Asn Ala Phe Ala Thr Gly Gly Lys Met Leu Ala Leu Gly Ser Gly Ala
            275                 280                 285
Ser Ala Thr Thr Ala Asn Ser Val Ala Leu Gly Ser Gly Ser Thr Thr
    290                 295                 300
Thr Ala Asn Leu Thr Ala Ala Gly Tyr Asn Pro Gly Ser Gly Thr Leu
305                 310                 315                 320
Ala Gly Thr Ser Gln Ala Thr Asn Gly Glu Val Ser Val Gly Asn Ala
                325                 330                 335
Gly Ala Glu Arg Arg Ile Thr Asn Val Ala Ala Gly Ser Ala Ala Thr
            340                 345                 350
Asp Ala Val Asn Val Ser Gln Leu Gln Ser Glu Asp Ala Lys Val Asn
            355                 360                 365
Thr Ile Asn Asn Asn Val Asn Asn Leu Ser Gly Ser Val Thr Asn Ile
            370                 375                 380
Ser Ser Thr Val Asn Asn Ile Thr Asn Gly Gly Gly Ile Lys Tyr Phe
385                 390                 395                 400
His Ala Asn Ser Thr Gln Ala Asp Ser Ser Ala Thr Gly Thr Asp Ala
                405                 410                 415
Val Ala Ile Gly Gly Asn Ala Gln Ala Thr Ala Ala Asn Ser Val Ala
            420                 425                 430
Leu Gly Leu Asn Ser Thr Ser Lys Gly Thr Asn Ala Ile Ala Leu Gly
            435                 440                 445
```

```
Gly Ala Val Ala Gly Ser Tyr Ala Phe Ala Ala Gly Ser Leu Ala
        450                 455                 460
Leu Ala Ala Thr Thr Gly Asp Ile Ala Leu Gly Ser Ser Ala Thr Ala
465                 470                 475                 480
Ser Ser Ala Asn Ser Asn Ala Tyr Ala Thr Ala Leu Gly Thr Asn Ala
                485                 490                 495
Leu Ala Asn Ala Thr Asp Ala Thr Ala Ile Gly Glu Gly Ala Ser Ala
            500                 505                 510
Thr Ala Ala Ser Ser Val Ala Leu Gly Ala Arg Ser Lys Thr Thr Ala
        515                 520                 525
Asn Leu Ser Thr Ala Gly Tyr Asn Pro Gly Thr Gly Thr Leu Ser Gly
530                 535                 540
Thr Thr Pro Thr Gly Glu Val Ser Val Gly Ser Ala Gly Lys Glu Arg
545                 550                 555                 560
Arg Val Thr Asn Val Ala Ala Gly Ser Ala Ala Thr Asp Ala Val Asn
                565                 570                 575
Val Ser Gln Leu Met Ser Glu Asp Ala Lys Val Asn Thr Ile Asn Asn
            580                 585                 590
Asn Val Asn Asn Leu Ser Asn Asn Val Thr Asn Ile Ala Gly Asn Val
        595                 600                 605
Thr Asn Ile Ser Asn Thr Val Asn Asn Ile Thr Asn Gly Gly Gly Ile
    610                 615                 620
Lys Tyr Phe His Val Asn Ser Thr Leu Ala Asp Ser Ser Ala Gly Gly
625                 630                 635                 640
Thr Asn Ser Ile Ala Ile Gly Gly Ala Thr Thr Gly Asn Val Thr
                645                 650                 655
Ala Gly Thr Ser Asp Asn Ile Ser Ile Gly Thr Asn Ala Thr Thr Asn
            660                 665                 670
Tyr Gly Lys Asn Ile Ala Ile Gly Asn Ala Gln Ala Leu Gly Gly
        675                 680                 685
Ala Tyr Asp Gly Gly Tyr Asn Thr Ala Ile Gly Glu Asn Ala Ile Ala
    690                 695                 700
Lys Gly Asp Gly Ala Gly Gly Phe Gly Gly Gly Trp Gly Gln Thr
705                 710                 715                 720
Thr Ala Ile Gly Gly Gly Ser Gln Ala Leu His Asp Asn Thr Thr Ala
                725                 730                 735
Val Gly Ser Gly Ala Ile Ala Asn Val Ala Asn Ala Thr Ala Leu Gly
            740                 745                 750
Met Ser Ala Ser Ala Thr Ala Gly Ser Ala Ile Ala Leu Gly Gln Gly
        755                 760                 765
Ala Val Ala Ser Ala Ala Asn Ser Val Ala Leu Gly Ser Gly Ser Thr
    770                 775                 780
Thr Thr Xaa Asn Leu Ser Ala Ala Gly Tyr Asn Pro Gly Thr Gly Thr
785                 790                 795                 800
Leu Ser Gly Ile Ala Ser Val Ala Asn Gly Glu Val Ser Val Gly Ala
                805                 810                 815
Ala Gly Lys Glu Arg Arg Ile Thr Asn Val Ala Ala Gly Ser Ala Ala
            820                 825                 830
Thr Asp Ala Val Asn Val Ser Gln Leu Gln Ser Glu Asp Ala Lys Val
        835                 840                 845
Asn Thr Ile Asn Asn Asn Val Asn Asn Leu Ser Gly Ser Val Thr Asn
    850                 855                 860
Ile Ser Asn Thr Val Asn Asn Ile Thr Asn Gly Gly Gly Ile Lys Tyr
865                 870                 875                 880
```

```
Phe His Thr Lys Ser Thr Leu Ala Asp Ser Ser Ala Thr Gly Thr Asp
                885                 890                 895

Ala Val Ala Ile Gly Gly Asn Ala Gln Ala Thr Ala Ala Asn Ser Val
            900                 905                 910

Ala Leu Gly Ser Asn Ser Thr Thr Thr Ala Asn Leu Ser Ala Ala Gly
        915                 920                 925

Tyr Asn Pro Gly Thr Gly Ala Leu Ser Gly Ile Ala Ser Ala Ala Asn
    930                 935                 940

Gly Glu Val Ser Val Gly Ala Ala Gly Lys Glu Arg Arg Ile Thr Asn
945                 950                 955                 960

Val Ala Ala Gly Ser Ala Ala Thr Asp Ala Val Asn Val Ser Gln Leu
                965                 970                 975

Gln Ser Glu Asp Ala Lys Val Asn Thr Ile Ser Asn Asn Val Asn Asn
            980                 985                 990

Leu Ser Gly Ser Val Thr Asn Ile Ser Ser Thr Val Asn Asn Ile Thr
        995                 1000                1005

Asn Gly Gly Gly Ile Lys Tyr Phe His Thr Asn Ser Thr Leu Ala Asp
    1010                1015                1020

Ser Thr Ala Asn Gly Val Asn Ser Ile Ala Ile Gly Gly Ala Thr Arg
1025                1030                1035                1040

Thr Asp Ala Asn Asn Ser Ile Ser Ile Gly Thr Gly Leu Thr Gln Ala
                1045                1050                1055

Ser Ser Asn Thr Gly Ala Ile Ala Ile Gly Gln Asn Ala Ser Ile Asn
            1060                1065                1070

Val Tyr Gly Ala Asn Ser Ile Ala Ile Gly Thr Asn Ser Ala Thr Gly
        1075                1080                1085

Gly Ile Gly Gly Ala Ile Ala Leu Gly Glu Asn Ala Phe Ala Thr Gly
    1090                1095                1100

Gly Lys Met Leu Ala Leu Gly Ser Gly Ala Ser Ala Thr Thr Ala Asn
1105                1110                1115                1120

Ser Val Ala Leu Gly Ser Gly Ser Thr Thr Thr Ala Asn Leu Thr Ala
                1125                1130                1135

Ala Gly Tyr Asn Pro Gly Ser Gly Thr Leu Ala Gly Thr Ser Gln Ala
            1140                1145                1150

Thr Asn Gly Glu Val Ser Val Gly Asn Ala Gly Ala Glu Arg Arg Ile
        1155                1160                1165

Thr Asn Val Ala Ala Gly Ser Ala Ala Thr Asp Ala Val Asn Val Ser
    1170                1175                1180

Gln Leu Gln Ser Glu Asp Ala Lys Val Asn Thr Ile Asn Asn Asn Val
1185                1190                1195                1200

Asn Asn Leu Ser Asn Asn Val Thr Asn Ile Ala Gly Asn Val Thr Asn
                1205                1210                1215

Ile Ser Asn Thr Val Asn Asn Ile Thr Asn Gly Gly Gly Ile Lys Tyr
            1220                1225                1230

Phe His Thr Lys Ser Thr Leu Ala Asp Ser Ser Ala Thr Gly Thr Asp
        1235                1240                1245

Ala Val Ala Ile Gly Gly Asn Ala Gln Ala Thr Ala Ala Asn Ser Val
    1250                1255                1260

Ala Leu Gly Ser Asn Ser Thr Thr Thr Ala Asn Leu Ser Ala Ala Gly
1265                1270                1275                1280

Tyr Asn Pro Gly Thr Gly Thr Leu Ser Gly Thr Thr Pro Thr Gly Glu
                1285                1290                1295

Val Ser Val Gly Ser Ala Gly Lys Glu Arg Arg Val Thr Asn Val Ala
```

```
                1300                1305                1310
Ala Gly Ser Ala Ala Thr Asp Ala Val Asn Val Ser Gln Leu Gln Ser
        1315                1320                1325
Ala Ile Ile Gly Ser Thr Ala Asn Ala Val Ala Tyr Asp Asp Gly Thr
    1330                1335                1340
Lys Ala Thr Val Thr Leu Lys Gly Ala Ser Gly Thr Lys Ile Thr Asn
1345                1350                1355                1360
Leu Thr Ala Gly Asn Leu Ser Ala Thr Ser Thr Asp Ala Val Asn Gly
            1365                1370                1375
Ser Gln Leu Tyr Ala Thr Asn Gln Asn Val Ser Asn Ile Gly Asn Thr
            1380                1385                1390
Val Asn Asn Ile Thr Asn Gly Gly Gly Ile Lys Tyr Phe His Ala Asn
        1395                1400                1405
Ser Thr Gln Ala Asp Ser Ser Ala Thr Gly Ser Asn Ser Val Ala Val
    1410                1415                1420
Gly Asp Arg Ala Ser Ser Leu Gly Gly Ser Ser Val Ala Met Gly Asp
1425                1430                1435                1440
Gly Ala Thr Ala Val Gly Ala Ala Ser Ile Ala Ile Gly Asn Asn Ala
            1445                1450                1455
Gln Asn Val Thr Gly Ser Asn Asn Ser Val Ala Ile Gly Gly Asp Ser
        1460                1465                1470
Lys Ala Gly Asp Arg Ser Val Ser Leu Gly Asn Gly Ala Asp Thr Ser
    1475                1480                1485
Leu Ser Ser Trp Gly Val Ala Val Gly Thr Asn Ala Asn Val Ser Ala
        1490                1495                1500
Ala Leu Gly Thr Ala Ile Gly Ala Gly Ala Asn Val Ser Gly Ala Asn
1505                1510                1515                1520
Ser Thr Ala Ile Gly Ala Asn Ala Val Ala Ser Ala Thr Asn Ser Val
            1525                1530                1535
Ala Leu Gly Ser Asn Ser Thr Thr Thr Ala Asn Leu Ser Ala Ala Gly
            1540                1545                1550
Tyr Asn Pro Gly Thr Gly Thr Leu Ser Gly Ile Ala Ser Ala Ala Asn
            1555                1560                1565
Gly Glu Val Ser Val Gly Ala Ala Gly Lys Glu Arg Arg Val Thr Asn
        1570                1575                1580
Val Ala Ala Gly Ser Ala Ala Thr Asp Ala Val Asn Val Ser Gln Leu
1585                1590                1595                1600
Gln Ser Glu Asp Ala Lys Val Asn Thr Ile Asn Asn Asn Val Asn Asn
            1605                1610                1615
Leu Ser Gly Ser Val Thr Asn Ile Ser Ser Thr Val Asn Asn Ile Thr
            1620                1625                1630
Asn Gly Ser Gly Ile Lys Tyr Phe His Thr Asn Ser Thr Leu Ala Asp
        1635                1640                1645
Ser Ser Ala Gly Gly Ala Asn Ser Ile Ala Ile Gly Gly Gly Ala Ala
        1650                1655                1660
Thr Ser Ser Ser Ala Gly Leu Ser Asp Asn Met Ala Ile Gly Thr Asn
1665                1670                1675                1680
Ala Thr Ala Ser Tyr Gly Lys Asn Ile Ala Ile Gly Gly Gly Ala Gln
            1685                1690                1695
Ala Thr Gly Gly Thr Tyr Asp Gly Gly Tyr Asn Val Ala Leu Gly Glu
            1700                1705                1710
Asn Ala Asn Ala Thr Ala Gly Thr Asn Ala Trp Gly His Asn Thr Ala
        1715                1720                1725
```

-continued

```
Ile Gly Ala Asn Thr Val Ile Asn Gly Val Asn Ser Val Ala Leu Gly
            1730                1735                1740

Ile Ser Ala Thr Thr Ser Gly Ser Gly Ser Met Ala Phe Gly Ser Ala
1745                1750                1755                1760

Ala Gln Ala Ser Ala Asp Tyr Ala Ile Ala Ser Gly Ala Gly Ala Asn
            1765                1770                1775

Ala Ser Ala Val Asn Ser Val Ala Leu Gly Ser Asn Ser Thr Thr Thr
            1780                1785                1790

Ala Asn Leu Ser Ala Ala Gly Tyr Asn Pro Gly Thr Gly Thr Leu Ser
            1795                1800                1805

Gly Ile Ala Ser Val Ala Asn Gly Glu Val Ser Val Gly Ser Ala Gly
            1810                1815                1820

Lys Glu Arg Arg Val Thr Asn Val Ala Ala Gly Ser Ala Ala Thr Asp
1825                1830                1835                1840

Ala Val Asn Val Ser Gln Leu Gln Ser Glu Asp Ala Lys Val Asn Thr
            1845                1850                1855

Ile Asn Asn Asn Val Asn Asn Leu Ser Asn Asn Val Ser Asn Ile Ala
            1860                1865                1870

Gly Asn Val Thr Asn Ile Ser Asn Thr Val Asn Ile Thr Asn Gly
            1875                1880                1885

Gly Gly Gly Ile Lys Tyr Phe His Ala Asn Ser Thr Leu Ala Asp Ser
            1890                1895                1900

Ser Ala Thr Gly Thr Asp Ala Val Ala Ile Gly Gly Asn Ala Gln Ala
1905                1910                1915                1920

Thr Ala Ala Asn Ser Val Ala Leu Gly Ser Asn Ser Thr Thr Thr Ala
            1925                1930                1935

Asn Leu Ser Ala Ala Gly Tyr Asn Pro Gly Thr Gly Thr Leu Ser Gly
            1940                1945                1950

Thr Thr Pro Val Gly Glu Val Ser Val Gly Ser Ala Gly Lys Glu Arg
            1955                1960                1965

Arg Val Thr Asn Val Ala Ala Gly Ser Ala Ala Thr Asp Ala Val Asn
            1970                1975                1980

Val Ser Gln Leu Gln Ser Ala Ile Ile Gly Ser Thr Ala Asn Ala Val
1985                1990                1995                2000

Ala Tyr Asp Asp Gly Thr Lys Ala Thr Val Thr Leu Lys Gly Ala Ser
            2005                2010                2015

Gly Thr Lys Ile Thr Asn Leu Thr Ala Gly Asn Leu Ser Ala Thr Ser
            2020                2025                2030

Thr Asp Ala Val Asn Gly Ser Gln Leu Tyr Ala Thr Asn Gln Asn Val
            2035                2040                2045

Ser Asn Val Gly Asn Thr Val Ser Asn Leu Ser Asn Asn Val Thr Asn
            2050                2055                2060

Ile Ala Gly Asn Val Thr Asn Ile Ser Asn Thr Val Asn Asn Ile Thr
2065                2070                2075                2080

Asn Gly Gly Gly Ile Lys Tyr Phe His Ala Asn Ser Thr Leu Ala Asp
            2085                2090                2095

Ser Ser Ala Thr Gly Thr Asp Ala Val Ala Ile Gly Gly Asn Ala Gln
            2100                2105                2110

Ala Thr Ala Ala Asn Ser Val Ala Leu Gly Ser Asn Ser Thr Thr Thr
            2115                2120                2125

Ala Asn Leu Ser Ala Ala Gly Tyr Asn Pro Gly Thr Gly Ala Leu Ser
            2130                2135                2140

Ala Thr Thr Pro Val Gly Glu Val Ser Val Gly Ser Ala Gly Lys Glu
2145                2150                2155                2160
```

```
Arg Arg Val Thr Asn Val Ala Ala Gly Ser Ala Ala Thr Asp Ala Val
            2165                2170                2175
Asn Val Ser Gln Leu Met Ser Glu Asp Ala Lys Val Asn Thr Ile Asn
            2180                2185                2190
Asn Asn Val Asn Asn Leu Ser Asn Val Ser Asn Ile Ala Gly Asn
            2195                2200                2205
Val Thr Asn Ile Ser Asn Thr Val Asn Ile Thr Asn Gly Gly Ser
            2210                2215                2220
Gly Ile Lys Tyr Phe His Ala Asn Ser Thr Leu Ala Asp Ser Ser Ala
2225                2230                2235                2240
Thr Gly Val Asp Ala Val Ala Ile Gly Gly Asn Ala Gln Ala Thr Ala
            2245                2250                2255
Ala Asn Ser Val Ala Leu Gly Ser Asn Ser Thr Thr Ala Asn Leu
            2260                2265                2270
Ser Ala Ala Gly Tyr Asn Pro Gly Thr Gly Ala Leu Ser Gly Ile Ala
            2275                2280                2285
Ser Ala Ala Asn Gly Glu Val Ser Val Gly Ala Ala Gly Lys Glu Arg
            2290                2295                2300
Arg Ile Thr Asn Val Ala Ala Gly Ser Ala Ala Thr Asp Ala Val Asn
2305                2310                2315                2320
Val Ser Gln Leu Gln Ser Glu Asp Ala Lys Val Asn Thr Ile Asn Asn
            2325                2330                2335
Asn Val Asn Asn Leu Ser Asn Asn Val Ser Asn Ile Ala Gly Asn Val
            2340                2345                2350
Thr Asn Ile Ser Asn Thr Val Asn Asn Ile Thr Asn Gly Gly Ser Gly
            2355                2360                2365
Ile Lys Tyr Phe His Ala Asn Ser Thr Leu Ala Asp Ser Ser Ala Thr
            2370                2375                2380
Gly Thr Asp Ala Val Ala Ile Gly Gly Asn Ala Ser Ala Ser Ala Ala
2385                2390                2395                2400
Asn Ser Val Ala Leu Gly Ser Asn Ser Thr Thr Thr Ala Asn Leu Ser
            2405                2410                2415
Ala Ala Gly Tyr Asn Pro Gly Ser Ala Ala Leu Ser Gly Thr Ala Ser
            2420                2425                2430
Ala Ala Asn Gly Glu Val Ser Val Gly Ala Ala Gly Lys Glu Arg Arg
            2435                2440                2445
Ile Thr Asn Val Ala Ala Gly Ser Ala Ala Thr Asp Ala Val Asn Val
            2450                2455                2460
Ser Gln Leu Gln Ser Glu Asp Ala Lys Val Asn Ala Glu Gly Ala Ala
2465                2470                2475                2480
Thr Ala Ala Ala Leu Gly Gly Gly Ser Thr Tyr Asn Thr Thr Thr Gly
            2485                2490                2495
Ala Ile Thr Ser Pro Thr Tyr Ile Ala Gly Gly Lys Thr Phe Asn Asn
            2500                2505                2510
Val Gly Asp Val Val Thr Asn Ile Asp Gly Arg Val Thr Gln Asn Ser
            2515                2520                2525
Thr Asp Ile Thr Asn Leu Thr Thr Thr Ile Asp Asn Gly Thr Ile Gly
            2530                2535                2540
Leu Val Gln Gln Ala Thr Pro Thr Ser Thr Ile Thr Val Ala Lys Asp
2545                2550                2555                2560
Thr Gly Gly Ala Thr Val Asp Phe Arg Gly Thr Gly Asn Ala Thr Arg
            2565                2570                2575
Thr Leu Thr Gly Ile Thr Ala Gly Glu Leu Ser Ala Thr Ser Thr Asp
```

```
                    2580             2585             2590
Ala Val Asn Gly Ser Gln Leu Tyr Ala Thr Asn Gln Asn Val Ser Asn
            2595             2600             2605

Ile Asp Asn Thr Val Ser Asn Leu Ser Asn Asn Val Thr Asn Ile Ala
            2610             2615             2620

Gly Asn Val Thr Asn Ile Ser Asn Thr Val Asn Asn Ile Thr Asn Gly
2625             2630             2635             2640

Gly Gly Gly Ile Lys Tyr Phe His Ala Asn Ser Thr Leu Ala Asp Ser
            2645             2650             2655

Ser Ala Thr Gly Val Asp Ala Val Ala Ile Gly Gly Asn Ala Gln Ala
            2660             2665             2670

Thr Ala Ala Asn Ser Val Ala Leu Gly Ser Asn Ser Thr Thr Thr Ala
            2675             2680             2685

Asn Leu Ser Ala Ala Gly Tyr Asn Pro Gly Thr Gly Thr Leu Ser Gly
            2690             2695             2700

Ile Ala Ser Ala Ala Asn Gly Glu Val Ser Val Gly Ala Ala Gly Lys
2705             2710             2715             2720

Glu Arg Arg Val Thr Asn Val Ala Ala Gly Ser Ala Ala Thr Asp Ala
            2725             2730             2735

Val Asn Val Ser Gln Leu Gln Ser Glu Asp Ala Lys Val Asn Thr Ile
            2740             2745             2750

Asn Asn Asn Val Asn Asn Leu Ser Asn Asn Val Ser Asn Ile Ala Gly
            2755             2760             2765

Asn Val Thr Asn Ile Ser Asn Thr Val Asn Asn Ile Thr Asn Gly Gly
            2770             2775             2780

Gly Gly Ile Lys Tyr Phe His Ala Asn Ser Thr Leu Ala Asp Ser Ser
2785             2790             2795             2800

Ala Thr Gly Thr Asn Ser Leu Ala Ala Gly Pro Ala Ala Val Ala Ser
            2805             2810             2815

Ala Thr Asp Ala Val Ala Leu Gly Asn Gly Ala Lys Ala Thr Asn Ala
            2820             2825             2830

Gly Ala Val Ala Leu Gly Ala Gly Ser Thr Thr Thr Ala Val Ala
            2835             2840             2845

Thr Ser Gly Thr Thr Ile Gly Gly Ile Thr Tyr Thr Phe Ala Gly Val
            2850             2855             2860

Ala Pro Ser Ser Thr Val Ser Val Gly Ala Ala Gly Ser Glu Arg Thr
2865             2870             2875             2880

Ile Thr Asn Val Ala Ala Gly Arg Leu Ser Ala Thr Ser Thr Asp Ala
            2885             2890             2895

Val Asn Gly Ser Glu Leu Phe Ala Thr Asn Gln Gln Val Thr Arg Asn
            2900             2905             2910

Thr Ala Asp Ile Thr Asn Leu Thr Asn Asn Met Asn Ile Gly Ser Val
            2915             2920             2925

Gly Leu Val Gln Gln Asp Ala Thr Thr Arg Thr Ile Thr Val Ala Lys
            2930             2935             2940

Ala Thr Asp Gly Thr Arg Val Asp Phe Thr Gly Thr Gly Gly Ala Arg
2945             2950             2955             2960

Gln Leu Thr Gly Val Ala Ala Gly Ala Val Asn Ala Thr Ser Val Asp
            2965             2970             2975

Ala Val Asn Gly Ser Gln Leu Tyr Gly Val Ser Gln Ser Val Ala Asp
            2980             2985             2990

Ala Ile Gly Gly Gly Ser Thr Val Asn Thr Asp Gly Ser Ile Ser Ala
            2995             3000             3005
```

-continued

```
Pro Thr Tyr Val Val Asp Gly Thr Val His Asn Ala Gly Asp Ala
3010                3015                3020

Ile Ser Asn Leu Asp Asn Arg Val Thr Gln Asn Thr Thr Asp Ile Ser
3025                3030                3035                3040

Thr Ile Asn Asn Thr Leu Asn Ser Ile Thr Thr Gly Ala Gly Val Lys
            3045                3050                3055

Tyr Val His Val Asn Ser Thr Leu Ala Asp Ser Leu Ala Lys Gly Ala
        3060                3065                3070

Glu Ser Val Ala Ile Gly Gly Asn Ala Gln Ser Gln Ala Ala Asn Ser
        3075                3080                3085

Val Ala Leu Gly Ser Asn Ser Val Ala Asp Arg Ala Asn Thr Val Ser
        3090                3095                3100

Val Gly Ala Ala Gly Ala Glu Arg Gln Ile Thr Asn Val Ala Ala Gly
3105                3110                3115                3120

Thr Ala Asp Thr Asp Ala Val Asn Val Ala Gln Leu Lys Ala Ser Gly
            3125                3130                3135

Val Ile Asn Thr Asp Gly Thr Thr Asn Ala Ala Val Thr Tyr Asp His
        3140                3145                3150

Asn Ala Asp Gly Ser Ala Asn Tyr Asn Ser Val Thr Met Gly Asn Gly
        3155                3160                3165

Val Ala Gly Gly Thr Thr Ile His Asn Val Ala Ala Gly Ser Ala Ala
        3170                3175                3180

Asp Asp Ala Val Asn Val Ser Gln Met Asn Ala Ala Ile Ser Ser Val
3185                3190                3195                3200

Ser Asn Ile Ile Gly Ser Ala Gly Asn Pro Leu Phe Thr Ala Asp Gly
            3205                3210                3215

Asn Arg Asp Thr Glu Ala Ala Val Ala Ser Gly Thr His Ala Thr Ala
            3220                3225                3230

Met Gly Ala Asn Ala Lys Ala Ser Ala Ala Asn Ser Val Ala Leu Gly
            3235                3240                3245

Ala Asn Ser Val Ala Asp Arg Glu Asn Thr Val Ser Val Gly Ser Ala
        3250                3255                3260

Gly Asn Glu Arg Gln Val Thr Asn Val Ala Ala Gly Thr Ala Thr Thr
3265                3270                3275                3280

Asp Ala Val Asn Val Gly Gln Leu Asn Gln Ala Ile Gly Ala Ser Ile
            3285                3290                3295

Gly Asn Leu Pro Ala Gly Met Ser Ala Lys Asp Tyr Thr Asp Gln Gln
            3300                3305                3310

Ile Asn Ala Val Gln Asn Gly Val Asn Gln Val Ala Lys Asn Ala Tyr
        3315                3320                3325

Ala Gly Ile Ala Ala Ala Thr Ala Leu Thr Met Ile Pro Asp Val Asp
        3330                3335                3340

Gln Gly Lys Thr Ile Ala Val Gly Val Gly Gly Ser Tyr Lys Gly
3345                3350                3355                3360

Ser Gln Ala Val Ala Leu Gly Ile Ser Ala Arg Ile Thr Gln Asn Leu
            3365                3370                3375

Lys Met Lys Ala Gly Ala Gly Thr Ser Ser Gln Gly Thr Thr Val Gly
            3380                3385                3390

Leu Gly Ala Ser Tyr Gln Trp
        3395
```

POLYPEPTIDES FOR OLIGOMERIC ASSEMBLY OF ANTIGENS

RELATED APPLICATIONS

This application is the U.S. National Phase of International Application No. PCT/IB2005/002528, filed Jul. 22, 2005 and published in English, which claims priority to U.S. Provisional Application No. 60/590,648, filed Jul. 23, 2004. The teachings of the above applications are incorporated herein in their entirety by reference.

All documents cited herein are incorporated by reference in their entirety.

FIELD OF THE INVENTION

This invention is in the field of antigen presentation. More particularly, it concerns the modification of proteins to allow their expression in oligomeric form e.g. on the surface of a cell.

BACKGROUND OF THE INVENTION

Many polypeptides that are naturally immunogenic lose this property when expressed recombinantly. In some cases the native polypeptide has structural features which do not form during expression in a heterologous host e.g. post-translational modifications may be incorrect, intermolecular interactions which influence conformation may be lost, etc. A further cause of lost immunogenicity is where a polypeptide (e.g. a surface-exposed polypeptide) is naturally oligomeric, and where this quaternary structure is required for immunogenicity (e.g. where the polypeptide has epitopes that are displayed only when a specific quaternary oligomeric structure is present). Loss of oligomeric structure can mean that the monomeric protein is less immunogenic than its native oligomeric counterpart.

In other cases the native polypeptide may be a transmembrane polypeptide that is not amenable to expression in a recombinant host. These problems are often seen when eukaryotic polypeptides (including those of eukaryotic viruses) are to be expressed in prokaryotes. One way of improving expression of viral transmembrane polypeptides is to remove their transmembrane domains and express only the antigenic extracellular domains {1}. However, this "soluble receptor" technology again suffers from loss of quaternary structure. If a native receptor exists in an oligomeric form on the surface of a virus, and the oligomerisation arises from sequences in the transmembrane region, the soluble receptor will lose its ability to oligomerise, and this loss can have functional consequences e.g. loss of signalling or of avidity. Loss of binding avidity, even though binding affinity may be retained, is a particular problem for antigens e.g. those used in vaccines.

Techniques for oligomerising proteins have been disclosed in references 2 and 3.

It is an object of the invention to provide ways of improving the expression of polypeptides, and particularly of antigenic polypeptides e.g. to retain their oligomeric structure.

SUMMARY OF THE INVENTION

The invention is based on a system for expressing antigenic polypeptides in oligomeric form. The antigenic polypeptide is fused to an oligomerisation polypeptide such that the oligomerisation polypeptide can interact with other oligomerisation polypeptides and bring multiple copies of the antigenic polypeptide into close proximity in the form of an oligomer. Expressing the polypeptides in oligomeric form in this way can improve their immunogenicity compared to a monomeric form.

Thus the invention provides a method for expressing a polypeptide of interest in a recombinant oligomeric form, wherein the polypeptide of interest is fused to an oligomerisation polypeptide such that a plurality of oligomerisation domains can associate in order to present the polypeptide of interest in oligomeric form. In particular, the method can be applied (a) to present the oligomerised polypeptide on the surface of a membrane, but including a transmembrane sequence in the structure, and (b) to present the oligomerised polypeptide by using structural features of an adhesin, such as a bacterial adhesin e.g. the NadA adhesin {4} from *Neisseria meningitidis*.

The invention can be applied to any antigenic polypeptide, including viral and non-viral antigens. It is particularly suitable for expressing surface polypeptides in an oligomeric form, such as the extracellular portions of surface proteins that are naturally found in an oligomeric form. The polypeptide of interest may be the full-length polypeptide or, alternatively, it may be a fragment of a full-length polypeptide e.g. it may comprise one or more domains of the full-length polypeptide.

The invention provides a polypeptide comprising: (a) a antigenic domain; (b) an oligomerisation domain; and (c) a transmembrane domain, wherein domains (a), (b) and (c) are not all found together in the same polypeptide in nature (and, in particular, wherein domains (a) and (b) are not found together in the same polypeptide in nature). The domains are in the order (a)-(b)-(c), running either from C-terminus to N-terminus or from N-terminus to C-terminus. It is more usual to have the transmembrane domain at or near the C-terminus of the protein.

Inclusion of a transmembrane domain in the polypeptide allows a plurality of oligomerisation domains to associate in order to present the polypeptide in oligomeric form on the surface of a membrane. As well as associating via their oligomerisation domains, polypeptides may also associate via interaction of their transmembrane domains within a lipid bilayer, thereby maintaining oligomeric structure. The inclusion of transmembrane sequences can also help in the correct folding of some antigens. The multimers of reference 2 are designed to avoid the presence of transmembrane sequences.

The invention provides a polypeptide comprising: (a) an antigenic domain; and (b) an oligomerisation domain from an adhesin, wherein domains (a) and (b) are not all found together in the same polypeptide in nature. The domains are in the order (a)-(b), running either from C-terminus to N-terminus or from N-terminus to C-terminus. The polypeptide will generally include sequences in addition to (a) and (b). For surface display of antigenic polypeptides, for instance, the invention will generally involve the use of a transmembrane domain in addition to an oligomerisation domain, as described above. The adhesin is preferably a bacterial adhesin, more preferably an 'Oca' adhesin, and most preferably the NadA adhesin from *Neisseria meningitidis*.

DESCRIPTION OF THE DRAWINGS

Figure 1:
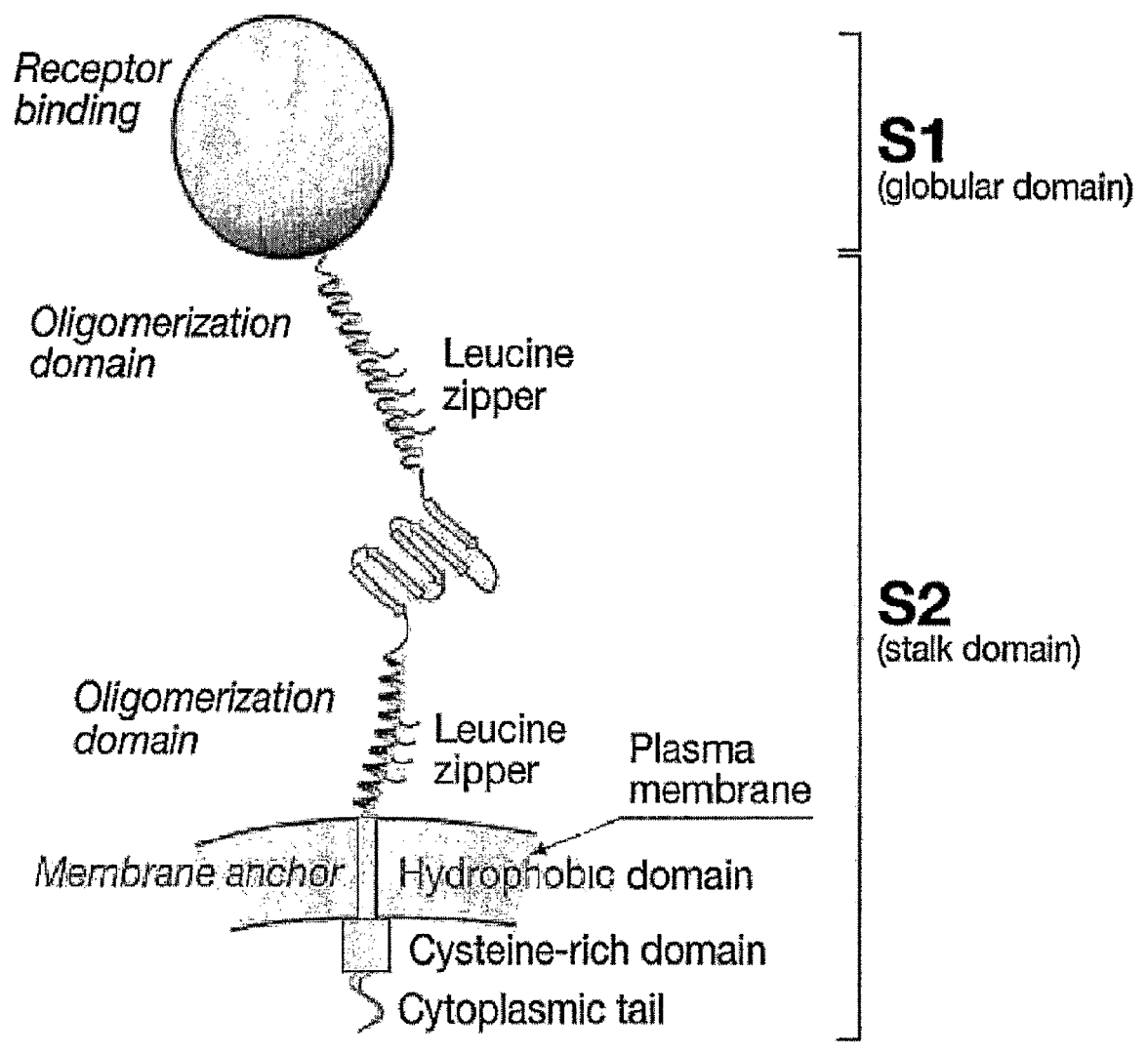

FIG. 1 illustrates the structure of a SARS coronavirus E2 monomer.

Figure 2:
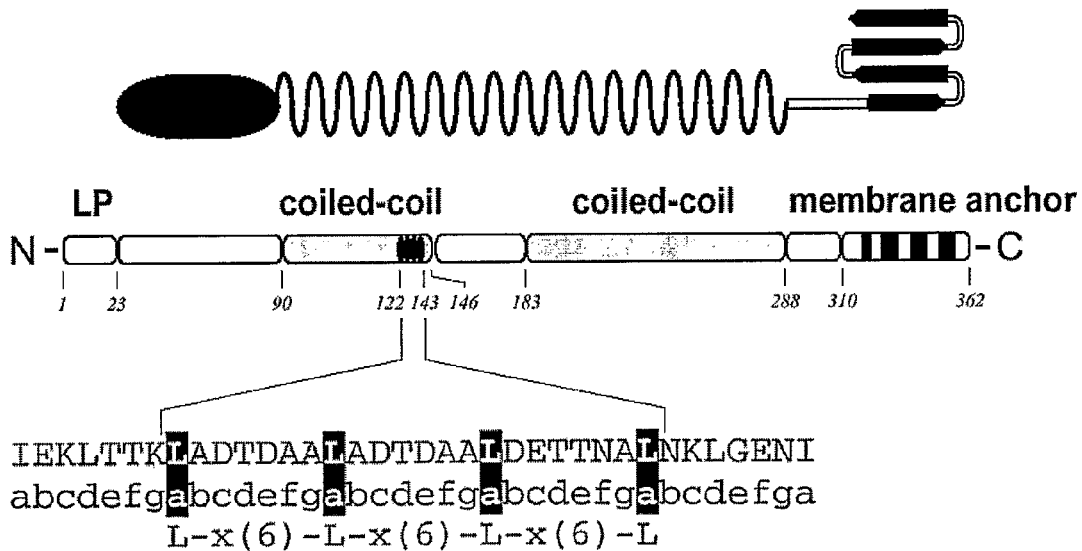
FIG. 2 illustrates the domains within meningococcal NadA protein {4}.
Figure 3:
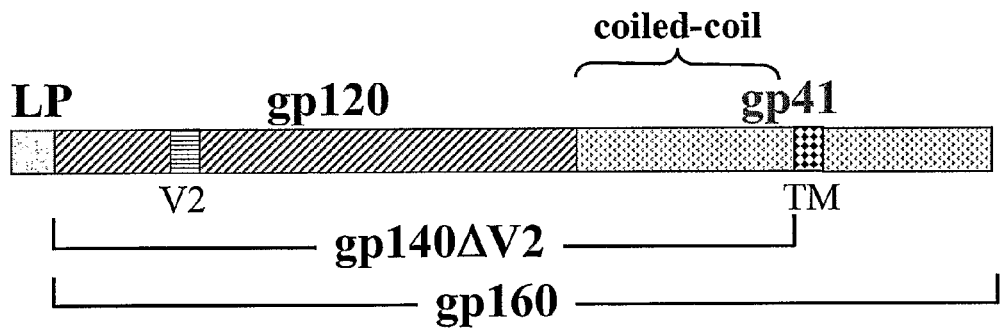
FIG. 3 illustrates the domains within HIV gp120 Env protein.
Figure 4:
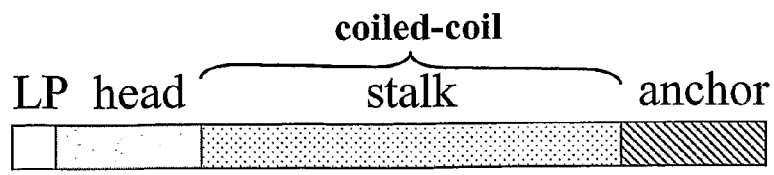
FIG. 4 illustrates domains within NadA.
Figure 5:
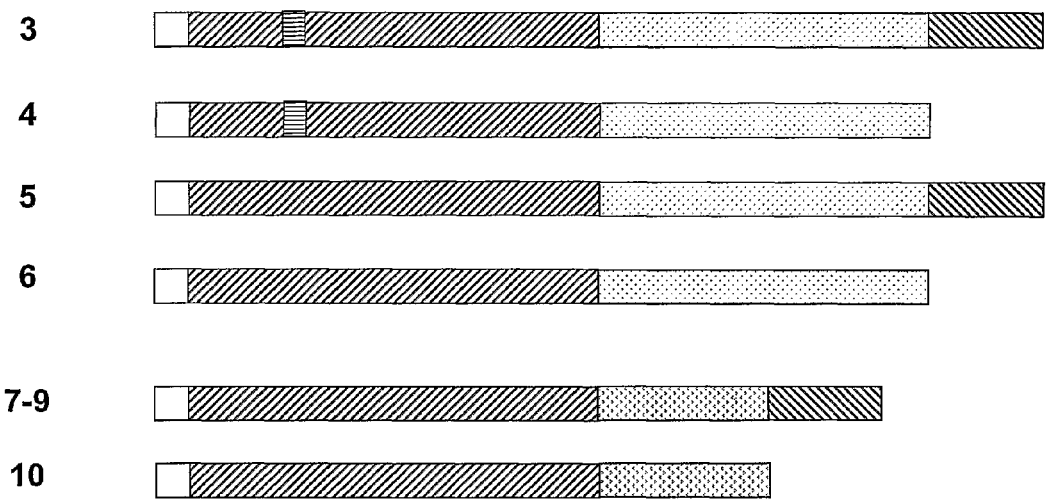
FIG. 5 shows hybrid proteins comprising regions from both Env and from NadA.
Figure 6:
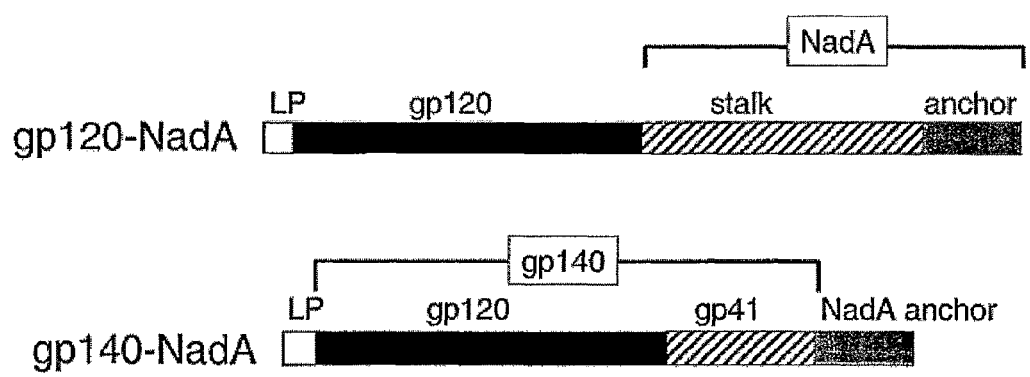
FIG. 6 shows the make-up of gp120-NadA (824aa) and gp140-NadA (741aa) constructs.

The envelope glycoproteins of rhabdoviridae. Rhabdoviridae include Rhabdoviruses, Vesiculoviruses, Lyssaviruses, Ephemeroviruses, Cytorhabdoviruses and Nucleorhabdoviruses. Viruses of interest include vesicular stomatitis virus, rabies virus, mokola virus, bovine ephemeral fever virus. The G proteins of rabies virus {32, 33}, lyssavirus {34} and mokola virus {34} form trimers on the viral surface and are of particular interest.

The envelope glycoproteins of togaviridae. Togaviridae include Alphaviruses and Rubiviruses. Viruses of interest include Sindbis virus, Eastern and Western encephalitis viruses, Semliki Forest virus, rubella virus, Aura virus, Babanki virus, Barmah Forest virus avis-A, bebaru virus, Buggy Creek virus, chikungunya virus, Everglades virus, Fort Morgan virus, getah virus, Highlands J virus, Kyzylagach virus, Mayaro virus, Middelburg virus, Mucambo virus, Ndumu virus, Ockelbo virus, o'nyong-nyong virus, Pixuna virus, Ross River virus, Sagiyama virus, Una virus, Venezuelan equine encephalitis virus, and Whataroa virus. The E1 spike protein of Semliki Forest virus forms trimeric coiled-coil structures {35} and is responsible for fusion, and is thus of particular interest.

The envelope ('E') glycoproteins of flaviviridae {36}. Flaviviridae include Flaviviruses, Pestiviruses and Hepaciviruses. Viruses of interest include dengue virus, hepatitis C virus, yellow fever virus, japanese encephalitis virus, west nile virus, St. Louis encephalitis virus, bovine diarrhea virus and tick-borne encephalitis (TBE) virus. The E proteins of west nile virus {37}, dengue virus {38}, yellow fever virus {38} and TBE virus {39} form trimeric structures on the viral surface and are of particular interest.

The envelope glycoproteins of bunyaviridae. Bunyaviridae include Bunyaviruses, Nairoviruses, Phleboviruses, Hantaviruses, and Tospoviruses. Viruses of interest include bunyavirus, Bunyamwera virus, california encephalitis virus, La Cross virus, Hantaan virus, Sin Nombre virus, Crimean-congo hemorrhagic fever virus, Sandfly fever Sicilian virus and Rift valley fever virus. The nucleocapsid proteins of hantaviruses form trimeric coiled coils {40} and is of particular interest.

The envelope glycoproteins of arenaviridae. Arenaviridae include lymphocytic choriomeningitis virus, ippy virus and lassa virus.

These proteins may be used in any known forms e.g. in native form, mutant form, truncated form, deleted form, etc. For example, various forms of HIV Env protein are known, including modified and domain-deleted proteins, and all of these various forms can be used with the invention.

Where a viral protein is naturally presented in a cleaved form (e.g. gp160 in HIV, cleaved to gp120/gp41; Spike protein in coronaviruses, cleaved to S1/S2; etc.), the invention preferably uses the N-terminus cleavage product, or the extracellular region, as the antigenic domain.

Within the group of viral surface proteins, a preferred sub-group is antigens which naturally form oligomers on the viral surface. Particularly preferred antigens are the viral fusion proteins (or spike proteins), which must usually be in oligomeric form in order to be fusogenically active {41}. The invention provides a way of presenting the antigenic portions of these proteins in a native oligomeric form. Preferred antigenic domains for use with the invention are thus the globular head domains of viral fusion proteins from enveloped viruses.

Viral fusion proteins are usually described in terms of a stalk domain and a globular head domain. The extraviral head domain contains the antigenic determinants, and the transmembrane stalk domain both anchors the protein to the virion envelope and mediates the native trimeric assembly via its coiled-coil motifs. In the native virion the stalk and head domains may be non-covalently or covalently associated. They may be formed by proteolytic cleavage of a precursor polypeptide, with the cleavage products remaining associated on the virion's surface.

The E2 spike protein of SARS coronavirus is a viral fusion polypeptide, and its S1 globular head domain can be used as an antigenic domain. Several genome sequences for the E2 protein are available, and SEQ ID NO: 1 herein is a preferred sequence. The globular head within SEQ ID NO: 1 is around residues 14 to 662 (SEQ ID NO: 2). Thus domain (a) in the polypeptide of the invention may comprise amino acid sequence SEQ ID NO:2 herein, or may comprise an amino acid sequence: (i) having at least m % identity to SEQ ID NO:2, where m is 50 or more (e.g. 60, 65, 70, 75, 80, 85, 90, 91, 92, 93, 94, 95, 96, 97, 98, 99, 99.5 or more); and/or (ii) which is a fragment of at least n consecutive amino acids of SEQ ID NO:2, wherein n is 7 or more (e.g. 8, 10, 12, 14, 16, 18, 20, 25, 30, 35, 40, 50, 60, 70, 80, 90, 100, 150, 200, 250 or more). These polypeptides include variants (e.g. allelic variants, homologs, orthologs, paralogs, mutants, etc.) of SEQ ID NO:2. Preferred fragments of (ii) comprise an epitope from SEQ ID NO:2, preferably a B-cell epitope. B-cell epitopes can be identified empirically or can be predicted algorithmically. Other preferred fragments of (ii) lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25, 45 or more) from the N-terminus of the relevant amino acid sequence from SEQ ID NO:2.

Within the amino acid sequence of a viral fusion polypeptide, the boundary of the globular head domain may not be known with absolute accuracy, but this is not a problem for practising the invention. The globular sequence can initially be identified approximately and then, if necessary, its boundaries can be determined by testing the antigenicity of the first approximation with and without neighbouring amino acid residues. Even so, the invention does not require the boundaries to be known with absolute precision, as the only basic requirement for the invention is that the sequence should function in a way which retains the relevant antigenic determinants of the viral protein without destroying the function of the other domains within the polypeptide. The inclusion of extraneous non-globular-head amino acids does not generally detract from this basic function.

Another preferred group of antigens is bacterial surface proteins. Specific bacteria whose surface proteins may be manipulated for oligomeric expression according to the invention are: *Neisseria meningitidis*, particularly serogroup B; *Neisseria gonorrhoeae; Streptococcus pneumoniae; Streptococcus pyogenes; Streptococcus agalactiae; Staphylococcus aureus; Haemophilus influenzae*, including type b and non-typeable strains; *Moraxella catarrhalis; Helicobacter pylori; Chlamydia trachomatis; Chlamydia pneumoniae; Corynebacterium diphtheriae; Clostridium tetani; Bor-*

*detella pertussis*; etc. The invention will generally use the extracellular antigenic region of a bacterial surface protein, with any bacterial transmembrane sequence being omitted. The transmembrane sequence of a bacterial surface protein can readily be identified (if present) based on pattern recognition, sequence analysis and homology.

Domain (a) in the polypeptide of the invention may comprise any of the following specific amino acid sequences, or may comprise an amino acid sequence: (i) having at least m % identity to one or more of the following amino acid sequences, where m is 50 or more (e.g. 60, 65, 70, 75, 80, 85, 90, 91, 92, 93, 94, 95, 96, 97, 98, 99, 99.5 or more); and/or (ii) which is a fragment of at least n consecutive amino acids of the following amino acid sequences, wherein n is 7 or more (e.g. 8, 10, 12, 14, 16, 18, 20, 25, 30, 35, 40, 50, 60, 70, 80, 90, 100, 150, 200, 250 or more):

Where the antigenic domain is derived from a *N. meningitidis* antigen, domain (a) may be based on an amino acid sequence selected from SEQ ID NO$^S$: 21 to 26.

Where the antigenic domain is derived from a *S. pneumoniae* antigen, domain (a) may be based on an amino acid sequence selected from PhtA, PhtD, PhtB, PhtE, SpsA, LytB, LytC, LytA, Sp125, Sp101, Sp128, Sp130 and Sp133, as disclosed in reference 42.

Where the antigenic domain is derived from a *S. pyogenes* or *S. agalactiae* antigen, domain (a) may be based on an amino acid sequence selected from the streptococcal amino acid sequences disclosed in reference 43.

Where the antigenic domain is derived from a *S. aureus* antigen, domain (a) may be based on an amino acid sequence selected from even-numbered SEQ ID NO$^S$: 2 to 5642 in ref. 44.

Where the antigenic domain is derived from a *H. influenzae* antigen, domain (a) may be based on an amino acid sequence selected from SEQ ID NOS: 2 to 5080 in reference 45.

Where the antigenic domain is derived from a *M. catarrhalis* antigen, domain (a) may be based on an amino acid sequence selected from the antigens disclosed in references 46 to 58.

These polypeptides include variants (e.g. allelic variants, homologs, orthologs, paralogs, mutants, etc.). Preferred fragments of (ii) comprise an epitope from said amino acid sequences, preferably a B-cell epitope. B-cell epitopes can be identified empirically or can be predicted algorithmically. Other preferred fragments of (ii) lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25, 45 or more) from the N-terminus of the amino acid sequences.

Within the amino acid sequence of a bacterial surface polypeptide, the boundary between an extracellular antigenic domain and a transmembrane domain may not be known with absolute accuracy, but this is not a problem for practising the invention. The antigenic sequence can initially be identified approximately and then, if necessary, its boundaries can be determined by testing the antigenicity of the first approximation with and without neighbouring amino acid residues. Even so, the invention does not require the boundaries to be known with absolute precision, as the only basic requirement for the invention is that the sequence should function in a way which retains the relevant antigenic determinants of the bacterial protein without destroying the function of the other domains within the polypeptide.

The Transmembrane Domain

Polypeptides of the invention will typically include a transmembrane domain that enables the polypeptide to be located within a lipid bilayer. Thousands of transmembrane sequences are available for use with the invention. In general terms, the transmembrane domain of one protein can be taken as a complete unit and substituted for the transmembrane domain of another protein, without disrupting the protein's membrane localisation.

When in situ within a lipid bilayer, the amino acid chain of the transmembrane domain will pass through the lipid bilayer at least once, but can pass through several times (single-pass or multi-pass). If it passes through the bilayer an odd number of times then the start of the transmembrane domain will be on the opposite side of the bilayer from the end of the transmembrane domain (and of the antigenic domain); if it passes through an even number of times then the start and end will be on the same side.

Transmembrane domains typically comprise α-helical sequences, although membrane-spanning β-stranded sequences are also known, as are α-helical sequences that include short pore-forming helices buried in the membrane.

One class of transmembrane domain which can be used with the invention is found in the seven-transmembrane-helix receptors (7-TMR family). As the name suggests, the transmembrane domain from these proteins crosses the lipid bilayer seven times. A comprehensive database of sequences of the human 7-TMR family is found in references 59 & 60.

More generally, the freely-available TMbase database {61, 62} includes details of transmembrane proteins and their helical membrane-spanning domains. In contrast, DB-NTMR {63} is a database of the non-transmembrane sequences of transmembrane proteins. TMPDB {64, 65} is a database of experimentally-characterised transmembrane topologies that have been determined by X-ray crystallography, NMR, gene-fusion technique, substituted cysteine accessibility method, N-linked glycosylation experiment and other biochemical methods.

Further transmembrane domains can be identified by subjecting amino acid sequences to the many transmembrane prediction algorithms that are available e.g. HMMTOP, TMHMM, TMPred, PHDhtm, DAS, TMFinder, SOSUI, TMAP, MEMSAT and TOPPred2 {66, 67}.

Within the amino acid sequence of a transmembrane protein, the boundary of the transmembrane domain may not be known with absolute accuracy (e.g. it may be unclear whether a particular amino acid residue should be classified as part of a transmembrane domain or as part of a cytoplasmic or extracellular domain), but this is not a problem for practising the invention. The transmembrane sequence can initially be identified approximately and then, if necessary, its boundaries can be determined by testing the sequence and truncated forms as fusions. Even so, the invention does not require the boundaries to be known with absolute precision, as the only basic requirement for the invention is that the sequence should function in a way which allows the polypeptide to be localised within a lipid bilayer without destroying the function of the other domains within the polypeptide. The inclusion of extraneous non-transmembrane amino acids on either or both sides of the membrane generally does not detract from this basic function of the transmembrane sequence.

Transmembrane domains can be taken from eukaryotic or prokaryotic polypeptides (e.g. from plants, animals, mammals, yeasts, Gram-negative bacteria, Gram-positive bacteria, viruses, etc.) or, alternatively, artificial transmembrane domains {e.g. 68} can be used.

Preferred transmembrane domains are those taken from bacterial transmembrane proteins. A preferred subset of transmembrane proteins is the adhesins. Specific transmembrane sequences for use with the invention are those from *Yersinia enterocolitica* adhesin YadA {69}, *Neisseria meningitidis* adhesin NadA {4}, *Moraxella catarrhalis* surface protein UspA2 {70} and other adhesins {71}, such as the transmembrane domains of SEQ ID NOS: 42-58. Thus domain (c) in the polypeptide of the invention may comprise one of NadA amino acid sequences SEQ ID NO$^S$: 15, 19, 20 or 40 herein, or may comprise an amino acid sequence: (i) having at least m % identity to one or more of SEQ ID NO$^S$: 15, 19, 20 or 40, where m is 50 or more (e.g. 60, 65, 70, 75, 80, 85, 90, 91, 92, 93, 94, 95, 96, 97, 98, 99, 99.5 or more); and/or (ii) which is a fragment of at least n consecutive amino acids of one or more of SEQ ID NO$^S$: 15, 19, 20 or 40 wherein n is 7 or more (e.g. 8, 10, 12, 14, 16, 18, 20, 25, 30, 35, 40, 50, 60, 70, 80, 90, 100, 150, 200, 250 or more). These polypeptides include variants (e.g. allelic variants, homologs, orthologs, paralogs, mutants, etc.) of SEQ ID NO$^S$: 15, 19, 20 & 40. Preferred fragments of (ii) comprise an epitope from one or more of SEQ ID NO$^S$: 15, 19, 20 & 40, preferably a B-cell epitope. B-cell epitopes can be identified empirically or can be predicted algorithmically. Other preferred fragments of (ii) lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25, 45 or more) from the N-terminus of the relevant amino acid sequence from SEQ ID NO$^S$: 15, 19, 20 & 40.

Other preferred transmembrane domains are those taken from the same protein as the antigenic domain. Thus domains (a) and (c) may be from the same protein, but with the oligomerisation domain being from a different protein. For example, if the antigenic domain is from the envelope protein of a virus (e.g. HIV) then the transmembrane domain may also be from that envelope protein.

Preferred Combinations of Domains (a), (b) and (c)

For domains (a), (b) and (c), it is preferred that at least one has a eukaryotic origin and at least one has a prokaryotic origin. Alternatively, at least one of (a), (b) and (c) may be an artificial domain that is not found in nature. A virus is considered to be a prokaryote or eukaryote based on its natural host e.g. HIV is a eukaryote, whereas a bacteriophage is a prokaryote.

The invention is particularly suitable for bacterial presentation of eukaryotic antigens. It is thus preferred that domain (c) is from a prokaryote, such as a bacterium, and that domain (a) is from a eukaryote, and more particularly from a eukaryotic virus. Domain (b) may be from a prokaryote or a eukaryote, but it is preferred to use a prokaryotic sequence.

In preferred embodiments, domains (b) and (c) are from the same prokaryotic protein. The domains are then certain to be compatible with each other and without the need for confirmation. Bacterial surface proteins are a preferred source for domains (b) and (c), with bacterial adhesins being useful. YadA, NadA, UspA2 the adhesins of reference 71 are suitable sources. The NadA adhesin is most preferred, and so domains (b) and (c) may together have an amino acid sequence such as SEQ ID NO: 41.

A particularly preferred polypeptide of the invention comprises: (a) an antigenic domain from the viral fusion protein of an enveloped eukaryotic virus; (b) a coiled-coil domain from a bacterial adhesin; and (c) a transmembrane domain from the same bacterial adhesin as (b). Examples of such proteins, having domains (b) and (c) from *N. meningitidis* NadA and domain (a) from HIV, are SEQ ID NOS: 3, 4, 5, 6, 32 and 33.

Further Sequences

As well as having domains (a), (b) and, optionally, (c), polypeptides of the invention may include further sequences.

Polypeptides may include a N-terminus leader or signal peptide to direct protein trafficking. These will be present in the nascent translated polypeptide, but will typically not be present in the mature form of the polypeptide e.g. when it is in situ within a lipid bilayer. Where a protein is to be displayed on the cell surface then a leader peptide that directs proteins to the membrane in the expression host is preferred. For expression in *E. coli* then the leader peptide of NadA can be conveniently used, but many other suitable leader peptides are available to the skilled person.

Polypeptides will typically include a cytoplasmic sequence which extends inwards from domain (c). This cytoplasmic sequence will typically be located at the C-terminus of domain (c), and at the C-terminus of the complete polypeptide. Suitable cytoplasmic tails are available from transmembrane proteins. For convenience, it is normal to use the cytoplasmic tail which is found in nature with domain (c), although modifications of the native tail sequence may, of course, be made. Thus the cytoplasmic sequence may comprise an amino acid sequence: (i) having at least m % identity to the natural cytoplasmic tail, where m is 50 or more (e.g. 60, 65, 70, 75, 80, 85, 90, 91, 92, 93, 94, 95, 96, 97, 98, 99, 99.5 or more); and/or (ii) which is a fragment of at least n consecutive amino acids of the cytoplasmic tail, wherein n is 7 or more (e.g. 8, 10, 12, 14, 16, 18, 20, 25, 30, 35, 40, 50, 60, 70, 80, 90, 100, 150, 200, 250 or more). Tails may influence protein trafficking.

Polypeptides may include amino acid sequences between these various domains. These can be artificial sequences (e.g. to assist in DNA manipulation or cloning, such as restriction sites) or can be taken from the same polypeptides as domains (a) to (c) e.g. the sequence already between a transmembrane domain and a coiled-coil sequence may be used. A useful artificial linker sequence is GSGGGG (SEQ ID NO:27), with the Gly-Ser dipeptide being formed from a BamHI restriction site, thus aiding cloning and manipulation, and the (Gly)$_4$ tetrapeptide being a typical poly-glycine linker for flexibility.

In general, therefore, polypeptides of the invention have the formula NH$_2$-A-B-C-D-E-F-G-H-COOH where: -A- is an optional leader sequence; -B- is an optional linker sequence; -C- is an antigenic sequence; -D- is an optional linker sequence; -E- is a coiled-coil sequence; -F- is an optional linker sequence; -G- is a transmembrane sequence; and -H- is an optional cytoplasmic tail.

Sequences -A-, -B-, -D-, -F- and -H- will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Short peptide can facilitate cloning or purification (e.g. histidine tags i.e. His$_h$ where h=3, 4, 5, 6, 7, 8, 9, 10 or more).

Polypeptides may include one or more protease recognition sequences, thereby allowing release of desired parts of the polypeptide (e.g. the extracellular portion) after it has been expressed e.g. such that a protein can be expressed conveniently on the cell surface, but then may be released for further use. A protease recognition sequence may be introduced at various positions e.g. between domains (e.g. together with a linker), or may be inserted within domains. A protease recognition sequence may be positioned between the coiled-coil domain and the antigenic domain, such that the protease releases the antigenic domain and disrupts oligomerisation, or it may be between the transmembrane domain and the coiled-coil domain, such that the protease releases the polypeptide in oligomeric form. Having the cleavage site within the coiled-coil domain will have various effects on oligomerisation depending on the site's position. Thus one or more of sequences -D-, -E- and/or -F- in the above formula may include a protease recognition site. It is preferred to include the site in sequence -F-.

The thrombin recognition sequence is LVPR/GS (SEQ ID NO: 38), and this can be inserted on its own or together with a linker (e.g. SEQ ID NO: 37). Other proteases and their recognition sequences are well known in the art.

Preparation of Nucleic Acid Vectors for Polypeptide Expression

Polypeptides of the invention can be prepared by various means (e.g. recombinant expression, purification from cell culture, chemical synthesis, etc.) and in various forms (e.g. native, with fusion partners, non-glycosylated, lipidated, etc.). They are preferably prepared in substantially pure form (i.e. substantially free from other bacterial or host cell proteins).

Use of a recombinant host is a preferred route for polypeptide expression according to the invention. The host will include a nucleic acid sequence encoding a polypeptide of the invention. Such nucleic acid sequences can be prepared by fusing, in frame, sequences encoding the separate domains of the protein. For example, nucleic acid fragments encoding an antigenic domain and an oligomerisation domain may be prepared by chemical synthesis, by amplification, or by digestion. After any necessary treatment to make the fragments compatible (e.g. blunt-ending, etc.) the fragments can be ligated such that their coding sequences are in-frame, to give a coding sequence for the polypeptide as a whole. The coding sequence can be placed into an expression vector downstream of a promoter and used for expression purposes.

Oligomers

Within the polypeptides of the invention, the coiled-coil domains confer the ability to assemble into oligomers e.g. dimers, trimers, tetramers or pentamers.

Thus the invention provides an oligomeric protein, comprising oligomerised polypeptides of the invention. The monomeric units of the oligomer may be the same or different e.g. for a dimeric protein, the invention provides both heterodimers and homodimers.

Hetero-oligomers can arise in several ways. For example: monomers may have the same transmembrane and coiled-coil domains, but different antigenic domains; monomers may have the same coiled-coil and antigenic domains, but different transmembrane domains; monomers may have the same transmembrane and antigenic domains, but different coiled-coil domains; monomers may share only one domain in common; etc. Formation of hetero-oligomeric coiled-coils is known {16}.

Preferred oligomers of the invention are trimers.

Hosts

The invention offers the convenience of expressing a eukaryotic polypeptide in a prokaryotic host, without losing the oligomeric assembly of the native eukaryotic polypeptide. The antigenic domain of the polypeptide will be extracellular when expressed. Thus the invention provides a host cell, wherein the host cell expresses a polypeptide of the invention. The polypeptide is preferably expressed on the surface of the host cell.

It is thus preferred to express the polypeptides of the invention in a prokaryotic host, such as a bacterium. *Escherichia coli* is a convenient host. Other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), *Shigella* spp., *Yersinia enterocolitica, Listeria monocytogenes*, yeasts, etc. These hosts may be manipulated to incorporate eukaryotic glycosylation pathways. In many cases, however, the lack of endogenous glycosylation pathways in bacterial hosts is an advantage, as glycosylation can mask immunogenically-important T- and B-cell epitopes.

Immunogens

The invention concerns expression of antigenic polypeptides. These are suitable for immunisation purposes, and the immunogen can take various forms.

For example, complete polypeptides may be purified for used as immunogens, either in monomeric or, preferably, in oligomeric form. Where a polypeptide includes a protease cleavage site, the polypeptides may be treated with protease and then the cleaved extracellular portions may be used as immunogens. Where a polypeptide is expressed in a cell, the cell itself may be used as an immunogen, with its surface exposed polypeptide giving immunogenic activity. As an alternative, outer membrane vesicles, or blebs, containing exposed polypeptides, may be used as immunogens.

Immunisation with cell membranes (either intact cells ('bacterial vector vaccines'), which may be live or killed, or membrane preparations derived from the cells) including the polypeptides of the invention is a preferred route. Host cells which contain nucleic acid of the invention and which express polypeptide of the invention may be used as delivery vehicles e.g. commensal bacteria {72}. This is particularly useful for delivery to mucosal surfaces, including oral administration, particularly if an intact cell's natural trophisms are exploited for in vivo delivery. Preferred bacterial hosts are genetically defined, attenuated and/or well-tolerated by a recipient animal or human. Preferred hosts for immunisation in this way include live oral *Salmonella* vector vaccines, *Yersinia enterocolitica, Shigella* spp., *Vibrio cholerae, Mycobacterium* strain BCG and *Listeria monocytogenes*.

Nucleic Acids

The invention also provides nucleic acid encoding the polypeptides of the invention. Furthermore, the invention provides nucleic acid which can hybridise to this nucleic acid, preferably under "high stringency" conditions (e.g. 65° C. in a 0.1×SSC, 0.5% SDS solution).

Nucleic acid according to the invention can be prepared in many ways (e.g. by chemical synthesis, from genomic or cDNA libraries, from the organism itself, etc.) and can take various forms (e.g. single stranded, double stranded, vectors, probes, etc.). They are preferably prepared in substantially pure form (i.e. substantially free from other bacterial or host cell nucleic acids).

The term "nucleic acid" includes DNA and RNA, and also their analogues, such as those containing modified backbones (e.g. phosphorothioates, etc.), and also peptide nucleic acids (PNA), etc. The invention includes nucleic acid comprising sequences complementary to those described above (e.g. for antisense or probing purposes).

Immunogenic Compositions and Medicaments

The invention provides a composition comprising a polypeptide and/or a nucleic acid of the invention. Compositions of the invention are preferably immunogenic compositions, and are more preferably vaccine compositions. Vaccines according to the invention may either be prophylactic (i.e. to prevent infection) or therapeutic (i.e. to treat infection), but will typically be prophylactic.

The pH of the composition is preferably between 6 and 8, preferably about 7. The pH may be maintained by the use of a buffer. The composition may be sterile and/or pyrogen-free. The composition may be isotonic with respect to humans.

The invention also provides a composition of the invention for use as a medicament. The medicament is preferably able to raise an immune response in a mammal (i.e. it is an immunogenic composition) and is more preferably a vaccine.

The invention also provides the use of one or more (e.g. 2, 3, 4, 5, 6) of the polypeptides of the invention in the manufacture of a medicament for raising an immune response in a mammal. The medicament is preferably a vaccine.

The invention also provides a method for raising an immune response in a mammal comprising the step of administering an effective amount of a composition of the invention. The immune response is preferably protective and preferably involves antibodies and/or cell-mediated immunity. The method may raise a booster response.

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

One way of checking efficacy of therapeutic treatment involves monitoring infections after administration of the composition of the invention. One way of checking efficacy of prophylactic treatment involves monitoring immune responses against the polypeptides after administration of the composition.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral (e.g. tablet, spray), vaginal, topical, transdermal {e.g. see ref. 73} or transcutaneous {e.g. see refs. 74 & 75}, intranasal {e.g. see ref. 76}, ocular, aural, pulmonary or other mucosal administration.

The invention may be used to elicit systemic and/or mucosal immunity.

Dosage treatment can be a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc.

Infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Further Components of the Composition

The composition of the invention will typically, in addition to the components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in reference 77.

Compositions of the invention may be administered in conjunction with immunoregulatory agents. In particular, compositions will usually include one or more adjuvants. Such adjuvants include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. {e.g. see chapters 8 & 9 of ref. 78}, or mixtures of different mineral compounds, with the compounds taking any suitable form (e.g. gel, crystalline, amorphous, etc.), and with adsorption being preferred. The mineral containing compositions may also be formulated as a particle of metal salt {79}.

B. Oil Emulsions

Oil emulsion compositions suitable for use as adjuvants in the invention include squalene-water emulsions, such as MF59 {Chapter 10 of ref. 78; see also ref. 80} (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations {Chapter 22 of Ref 78}

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 81. Saponin formulations may also comprise a sterol, such as cholesterol {82}.

Combinations of saponins and cholesterols can be used to form unique particles called immunostimulating complexes (ISCOMs) {chapter 23 of ref. 78}. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 82-84. Optionally, the ISCOMS may be devoid of additional detergent {85}.

A review of the development of saponin based adjuvants can be found in refs. 86 & 87.

D. Virosomes and Virus-Like Particles

Virosomes and virus-like particles (VLPS) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 88-93. Virosomes are discussed further in, for example, ref. 94

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 95. Such "small particles" of 3dMPL are small enough to be sterile filtered through a 0.22 µm membrane {95}. Other non-toxic LPS derivatives include monophosphoryl lipid A mimics, such as aminoalkyl glucosaminide phosphate derivatives e.g. RC-529 {96, 97}.

Lipid A derivatives include derivatives of lipid A from *Escherichia coli* such as OM-174. OM-174 is described for example in refs. 98 & 99.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 100, 101 and 102 disclose possible analog substitutions e.g. replacement of guanosine with 2'-deoxy-7-deazaguanosine. The adjuvant effect of CpG oligonucleotides is further discussed in refs. 103-108.

The CpG sequence may be directed to TLR9, such as the motif GTCGTT or TTCGTT {109}. The CpG sequence may be specific for inducing a Th1 immune response, such as a CpG-A ODN, or it may be more specific for inducing a B cell response, such a CpG-B ODN. CpG-A and CpG-B ODNs are discussed in refs. 110-112. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 109 & 113-115.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 116 and as parenteral adjuvants in ref. 117. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivaties thereof, particularly LT-K63 and LT-R72, as adjuvants can be found in refs. 118-125. Numerical reference for amino acid substitutions is preferably based on the alignments of the A and B subunits of ADP-ribosylating toxins set forth in ref. 126, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 {127}, etc.) {128}, interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres {129} or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention {130}.

H. Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref 78)

Examples of liposome formulations suitable for use as adjuvants are described in refs. 131-133.

J. Polyoxyethylene Ether and Polyoxyethylene Ester Formulations

Adjuvants suitable for use in the invention include polyoxyethylene ethers and polyoxyethylene esters {134}. Such formulations further include polyoxyethylene sorbitan ester surfactants in combination with an octoxynol {135} as well as polyoxyethylene alkyl ethers or ester surfactants in combination with at least one additional non-ionic surfactant such as an octoxynol {136}. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 137 and 138.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 139 and 140.

The invention may also comprise combinations of aspects of one or more of the adjuvants identified above. For example, the following adjuvant compositions may be used in the invention: (1) a saponin and an oil-in-water emulsion {141}; (2) a saponin (e.g. QS21)+a non-toxic LPS derivative (e.g. 3dMPL) {142}; (3) a saponin (e.g. QS21)+a non-toxic LPS derivative (e.g. 3dMPL)+a cholesterol; (4) a saponin (e.g. QS21)+3dMPL+IL-12 (optionally+a sterol) {143}; (5) combinations of 3dMPL with, for example, QS21 and/or oil-in-water emulsions {144}; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 78.

Further Antigens

As well as containing polypeptides of the invention, the compositions of the invention may also include one or more further antigens. Further antigens for inclusion may be, for example:

antigens from *Helicobacter pylori* such as CagA {145 to 148}, VacA {149, 150}, NAP {151, 152, 153}, HopX {e.g. 154}, HopY {e.g. 154} and/or urease.

a protein antigen from *N. meningitidis* serogroup B, such as those in refs. 155 to 161.

an outer-membrane vesicle (OMV) preparation from *N. meningitidis* serogroup B, such as those disclosed in refs. 162 to 165, etc.

a saccharide antigen from *N. meningitidis* serogroup C, such as the oligosaccharide disclosed in ref. 166 from serogroup C {see also ref. 167}.

a saccharide antigen from *Streptococcus pneumoniae* {e.g. 168, 169, 170}.

an antigen from hepatitis A virus, such as inactivated virus {e.g. 171, 172}.

an antigen from hepatitis B virus, such as the surface and/or core antigens {e.g. 172, 173}.

an antigen from hepatitis C virus {e.g. 174}.

a diphtheria antigen, such as a diphtheria toxoid {e.g. chapter 3 of ref. 175} e.g. the CRM$_{197}$ mutant {e.g. 176}.

a tetanus antigen, such as a tetanus toxoid {e.g. chapter 4 of ref. 175}.

an antigen from *Bordetella pertussis*, such as pertussis holotoxin (PT) and filamentous haemagglutinin (FHA) from *B. pertussis*, optionally also in combination with pertactin and/or agglutinogens 2 and 3 {e.g. refs. 177 & 178}.

a cellular pertussis antigen.

a saccharide antigen from *Haemophilus influenzae* B {e.g. 167}.

an antigen from *N. gonorrhoeae* {e.g. 155, 156, 157}.

an antigen from *Chlamydia pneumoniae* {e.g. 179, 180, 181, 182, 183, 184, 185}.

an antigen from *Chlamydia trachomatis* {e.g. 186}.

an antigen from *Porphyromonas gingivalis* {e.g. 187}.

polio antigen(s) {e.g. 188, 189} such as IPV or OPV.

rabies antigen(s) {e.g. 190} such as lyophilised inactivated virus {e.g. 191, RabAvert™}.

measles, mumps and/or rubella antigens {e.g. chapters 9, 10 & 11 of ref. 175}.

antigen(s) from influenza virus {e.g. chapter 19 of ref. 175}, such as the haemagglutinin and/or neuraminidase surface proteins antigen(s) from a paarmyxovirus such as respiratory syncytial virus (RSV {192, 193}) and/or parainfluenza virus (PIV3 {194}).

an antigen from *Moraxella catarrhalis* {e.g. 195}.

an antigen from *Streptococcus agalactiae* (group B *streptococcus*) {e.g. 196, 197}.

an antigen from *Streptococcus pyogenes* (group A *streptococcus*) {e.g. 197, 198, 199}.

an antigen from *Staphylococcus aureus* {e.g. 200}.

an antigen from *Bacillus anthracis* {e.g. 201, 202, 203}.

an antigen from a virus in the flaviviridae family (genus flavivirus), such as from yellow fever virus, Japanese encephalitis virus, four serotypes of Dengue viruses, tick-borne encephalitis virus, West Nile virus.

a pestivirus antigen, such as from classical porcine fever virus, bovine viral diarrhoea virus, and/or border disease virus.

a parvovirus antigen e.g. from parvovirus B19.

a prion protein (e.g. the CJD prion protein)

an amyloid protein, such as a beta peptide {204} a cancer antigen, such as those listed in Table 1 of ref. 205 or in tables 3 & 4 of ref. 206.

The composition may comprise one or more of these further antigens. It is preferred that combinations of antigens should be based on shared characteristics e.g. antigens associated with respiratory diseases, antigens associated with enteric diseases, antigens associated with sexually-transmitted diseases, etc.

Where a saccharide or carbohydrate antigen is used, it is preferably conjugated to a carrier protein in order to enhance immunogenicity {e.g. refs. 207 to 216}. Preferred carrier proteins are bacterial toxins or toxoids, such as diphtheria or tetanus toxoids. The CRM$_{197}$ diphtheria toxoid is particularly preferred {217}. Other carrier polypeptides include the *N. meningitidis* outer membrane protein {218}, synthetic peptides {219, 220}, heat shock proteins {221, 222}, pertussis proteins {223, 224}, protein D from *H. influenzae* {225}, cytokines {226}, lymphokines {226}, hormones {226}, growth factors {226}, toxin A or B from *C. difficile* {227}, iron-uptake proteins {228}, etc. Different saccharides can be conjugated to the same or different type of carrier protein. Any suitable conjugation reaction can be used, with any suitable linker where necessary.

As an alternative to using protein antigens in the composition of the invention, nucleic acid encoding the antigen may be used {e.g. refs. 229 to 237}. Protein components of the compositions of the invention may thus be replaced by nucleic acid (preferably DNA e.g. in the form of a plasmid) that encodes the protein.

Processes

The invention also provides a process for producing a polypeptide of the invention, comprising the step of culturing a host cell transformed with nucleic acid of the invention under conditions which induce polypeptide expression.

The invention provides a process for producing a polypeptide of the invention, comprising the step of synthesising at least part of the polypeptide by chemical means.

The invention provides a process for producing nucleic acid of the invention, comprising the step of amplifying nucleic acid using a primer-based amplification method (e.g. PCR).

The invention provides a process for producing nucleic acid of the invention, comprising the step of synthesising at least part of the nucleic acid by chemical means.

General

The term "comprising" encompasses "including" as well as "consisting of" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 238. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in reference 239.

In certain embodiments, the invention does not encompass a polypeptide in which: (a) the oligomerisation domain is the NadA adhesin from *N. meningitidis*, or a fragment thereof; and (b) the antigenic domain is the SARS coronavirus S1 protein, or a fragment thereof. Similarly, in certain embodiments the invention does not encompass nucleic acid encoding such a polypeptide. These polypeptides and nucleic acids are disclosed in reference 240 and are thus disclaimed from certain embodiments of the present invention.

MODES FOR CARRYING OUT THE INVENTION

Identification of Bacterial Adhesins

Virulence-associated antigens involved in adhesion have been identified in several bacteria {71}, and the stalk domains of these antigens can be used with heterologous antigenic sequences according to the invention.

Antigens have been identified in: *Haemophilus influenzae* biogroup *aegyptius* ('HadA', SEQ ID NO: 29); *Escherichia coli* K1 (SEQ ID NOS: 42 & 43) and also in EHEC strain EDL933; *Actinobacillus actinomycetemcomitans* (SEQ ID NO: 44); *Haemophilus somnus* (SEQ ID NO: 45); *Haemophilus ducreyi* (SEQ ID NO: 46); EPEC *E. coli* strain E2348/69 (SEQ ID NOS: 47 & 48); EAEC *E. coli* strain O42 (SEQ ID NOS: 49 & 50); uropathogenic *E. coli* (SEQ ID NO: 51); *Shigella flexneri* (SEQ ID NO: 52); *Brucella melitensis* (SEQ ID NO: 53); *Brucella suis* (SEQ ID NO: 54); *Ralstonia solanacearum* (SEQ ID NO: 55); *Sinorhizobium meliloti* (SEQ ID NO: 56); *Bradorhizobium japonicum* (SEQ ID NO: 57); and *Burkholderia fungorum* (SEQ ID NO: 58).

The positions of these features in SEQ ID NO$^S$: 29 & 42-58 are as follows:

| SEQ ID | Organism | Length | Leader | Head | Coiled-coil | Anchor |
|---|---|---|---|---|---|---|
| 29 | H. aegyptius | 256 | 1-26 | 27-55 | 56-184 | 185-256 |
| 42 | EHEC | 338 | 1-23 | 24-207 | 208-266 | 267-338 |
| 43 |  | 1588 | 1-53 | 54-1515 * |  | 1516-1588 |
| 44 | A. actinomycetemcomitans | 295 | 1-25 | 26-150 | 151-222 | 223-295 |
| 45 | H. somnus | 452 | 1-26 | 27-158 | 159-378 | 379-452 |
| 46 | H. ducreyi | 273 | 1-21 | 22-198 * |  | 199-273 |
| 47 | EPEC | 338 | 1-24 | 25-209 | 210-266 | 267-338 |
| 48 |  | 577 |  | 1-504 * |  | 505-577 |
| 49 | EAEC | 717 | 1-23 | 24-109 | 110-645 | 646-717 |
| 50 |  | 1743 | 1-53 | 54-1670 * |  | 1671-1743 |
| 51 | UPEC | 1778 | 1-53 | 54-1705 * |  | 1706-1778 |
| 52 | S. flexneri | 990 |  | 1-917 * |  | 918-990 |
| 53 | B. melitensis | 227 | 1-27 | 28-122 | 123-154 | 155-227 |
| 54 | B. suis | 311 | 1-27 | 28-206 | 207-238 | 239-311 |
| 55 | R. solanacearum | 1309 |  | 1-230* |  | 231-708 | 1239-1309 |
| 56 | S. meliloti | 1291 |  | 1-1219 * |  | 1220-1291 |
| 57 | B. japonicum | 372 | 1-72 | 73-300 * |  | 301-372 |
| 58 | B. fungorum | 3399 | 1-57 | 58-3328 * |  | 3329-3399 |

* The boundary between domains is less distinct for some of these adhesins

SARS Coronavirus Spike Protein

The E2 spike protein of the SARS coronavirus has been reported. An amino acid sequence of this protein is given herein as SEQ ID NO:1. A secondary structure prediction is given below, where C represents a coil, H represents a helix and E represents an extended sequence:

```
         10        20        30        40        50        60        70
          |         |         |         |         |         |         |
MFIFLLFLTLTSGSDLDRCTTFDDVQAPNYTQHTSSMRGVYYPDEIFRSDTLYLTQDLFLPFYSNVTGFH
CeEEEEEEccCCCcceeeeCCCCCCCCCCCCceEEEEEeCCcEEEEEEEEceEEEEEEeceEEcCeEe TINHTFGNPVIPFKDGIYFAATEKSNVVRGWVFGSTMNNKSQSVIIINNSTNVVIRACNFELCDNPFFAV
ceeeeCCCceeeEeCCccecCCCCCCceEEEEEEEEccCCCcEEEEEeCCCEEEEEEEEEeccCCCCCCC SKPMGTQTHTMIFDNAFNCTFEYISDAFSLDVSEKSGNFKHLREFVFKNKDGFLYVYKGYQPIDVVRDLP
CCCCCCeEEEEEEEcCCCCcEEEEEeeeEEEcCCCCCChhHHheEEEEeCCCEEEEEEcCCCCCCcCCCC SGFNTLKPIFKLPLGINITNFRAILTAFSPAQDIWGTSAAAYFVGYLKPTTFMLKYDENGTITDAVDCSQ
CCCccccccceEEEeeeceeeeEEEeccCcCCCcCCcchHHhhhcccceEEEEEcCCCCEEEEeccCCC
```

-continued

```
NPLAELKCSVKSFEIDKGIYQTSNFRVVPSGDVVRFPNITNLCPFGEVFNATKFPSVYAWERKKISNCVA
CCCceEEeCceEeeeCCcEEEeCCeEEEeeCCEEEEeCCCCCCCcccceecCCCCCCccHHHhHHHhhcch DYSVLYNSTFFSTFKCYGVSATKLNDLCFSNVYADSFVVKGDDVRQIAPGQTGVIADYNYKLPDDFMGCV
hHHHHHHHhhceEEeeeeceeecceccccceeeEeEeeEEEcCCCeeecccCCCceEeeccceeCCcceEE LAWNTRNIDATSTGNYNYKYRYLRHGKLRPFERDISNVPFSPDGKPCTPPALNCYWPLNDYGFYTTTGIG
EEEeCCCCCcCCCCCCCCceccccCccCcccCCCCCCCCCCCCCCCCCCCCCCCCCCCCCceeccCCcc YQPYRVVVLSFELLNAPATVCGPKLSTDLIKNQCVNFNFNGLTGTGVLTPSSKRFQPFQQFGRDVSDFTD
eeEEEEEEEEEeCCCCCcccCCCCcCCCceEEeeeeEEEEeeccceeeeHHHHHHHhhHHHhheccCCCcc SVRDPKTSEILDISPCSFGGVSVITPGTNASSEVAVLYQDVNCTDVSTAIHADQLTPAWRIYSTGNNVFQ
ccccccCCCcEEEEEEccCceEEEEEeCCCCCCCceEEeeecceEEEeCCCCcccCCCCcccCCCCcHHH TQAGCLIGAEHVDTSYECDIPIGAGICASYHTVSLLRSTSQKSIVAYTMSLGADSSIAYSNNTIAIPTNF
hhccceeeccCCCCCCCCCccCCCcceeEEeecceeeeeecCeEEEEEecCCCCCcccCCCCeEEeeCcc SISITTEVMPVSMAKTSVDCNMYICGDSTECANLLLQYGSFCTQLNRALSGIAAEQDRNTREVFAQVKQM
EcccceEEEEEeCCceeecccccccCChHHHHHHHHHhHHHHHHHHHHHHHHHHhchHHHHHHHHHhC YKTPTLKYFGGFNFSQILPDPLKPTKRSFIEDLLFNKVTLADAGFMKQYGECLGDINARDLICAQKFNGL
CeeeEEecCCceeccccCCCCCCCcCChHHHHHHHhcccCeeeeccccecccccCCCcccccEEEEEEcCCc TVLPPLLTDDMIAAYTAALVSGTATAGWTFGAGAALQIPFAMQMAYRFNGIGVTQNVLYENQKQIANQFN
EeccCCCCcHHHHHHHHHHHhhhcCCCchhHhhHHHhccceeEeEhhhcCCcchhhHHHHHHHHHHHHH KAISQIQESLTTTSTALGKLQDVVNQNAQALNTLVKQLSSNFGAISSVLNDILSRLDKVEAEVQIDRLIT
HHHHHHHHhhHhHHHHHHHHHHHHHHHHHHHHHHHHHHHHHhcchHHHHHHHHHHHHHHHHHHHHHH GRLQSLQTYVTQQLIRAAEIRASANLAATKMSECVLGQSKRVDFCGKGYHLMSFPQAAPHGVVFLHVTYV
HHHHHHHHHHHHHHhHHHHHHHHHHHHHHHHHHHHHHhccccecccccchhHhheeeccCCCcEEEEEEEE PSQERNFTTAPAICHEGKAYFPREGVFVFNGTSWFITQRNFFSPQIITTDNTFVSGNCDVVIGIINNTVY
ECceeeeeccCCeeeeeeeeccCcEEEecCCEEEEcCCCCccCCCcccCCCEEEEEEEEEEeCCceecC DPLQPELDSFKEELDKYFKNHTSPDVDFGDISGINASVVNIQKEIDRLNEVAKNLNESLIDLQELGKYEQ
cCCCCCCcHHHHHHHHHHhCCCCCCCCCcCcceeEeeeccHHHHHHHHHHHHHhcchhhHHhCCCeEEE YIKWPWYVWLGFIAGLIAIVMVTILLCCMTSCCSCLKGACSCGSCCKFDEDDSEPVLKGVKLHYT
EecchHHHHHHHHHHHhheeEEEEEEEeCCCCcceecCCCCCCCcccCCCCCCeEEcccEEEcC
```

HIV Envelope Protein

The HIV envelope glycoprotein is expressed as gp160 from the HIV genome, and is cleaved post-translationally to give gp120 and gp41, which remain associated. The gp120 protein is the extracellular domain of the envelope, and the gp41 protein is the transmembrane protein of the envelope. The associated proteins form trimers on the virion surface, but recombinantly-expressed gp120 is monomeric. To increase the immunogenicity of the envelope protein, it has been expressed in E. coli as a non-glycosylated trimer by using the NadA oligomerisation structures.

The sequence of the Envelope protein up

| SEQ ID NO: | Length | Description of polypeptide |
|---|---|---|
| 32 | 824 | aa 1-29: leader of NadA (SEQ ID NO: 11)<br>aa 30-504: gp120 (SEQ ID NO: 36)<br>aa 505-506: Gly-Ser dipeptide (SEQ ID NO: 14)<br>aa 507-824: NadA stalk & anchor<br>(SEQ ID NO: 13 + SEQ ID NO: 15) |
| 33 | 837 | aa 1-29: leader of NadA (SEQ ID NO: 11)<br>aa 30-504: gp120 (SEQ ID NO: 36)<br>aa 505-506: Gly-Ser dipeptide (SEQ ID NO: 14)<br>aa 507-734 & 748-837: NadA stalk & anchor<br>(SEQ ID NOs: 13 + 15)<br>aa 735-747: thrombin cleavage sequence<br>(SEQ ID NO: 37) |
| 34 | 741 | aa 1-29: leader of NadA (SEQ ID NO: 11)<br>aa 30-665: gp140 (mut3-5) (SEQ ID NO: 39)<br>aa 666-667: Lys-Leu dipeptide (SEQ ID NO: 18)<br>aa 668-741: NadA anchor (SEQ ID NO: 19) |
| 35 | 768 | aa 1-29: leader of NadA (SEQ ID NO: 11)<br>aa 30-665: gp140 (mut3-5) (SEQ ID NO: 39)<br>aa 666-678: thrombin cleavage sequence<br>(SEQ ID NO: 37)<br>aa 679-768: NadA anchor (SEQ ID NO: 40) |

Figure 7:
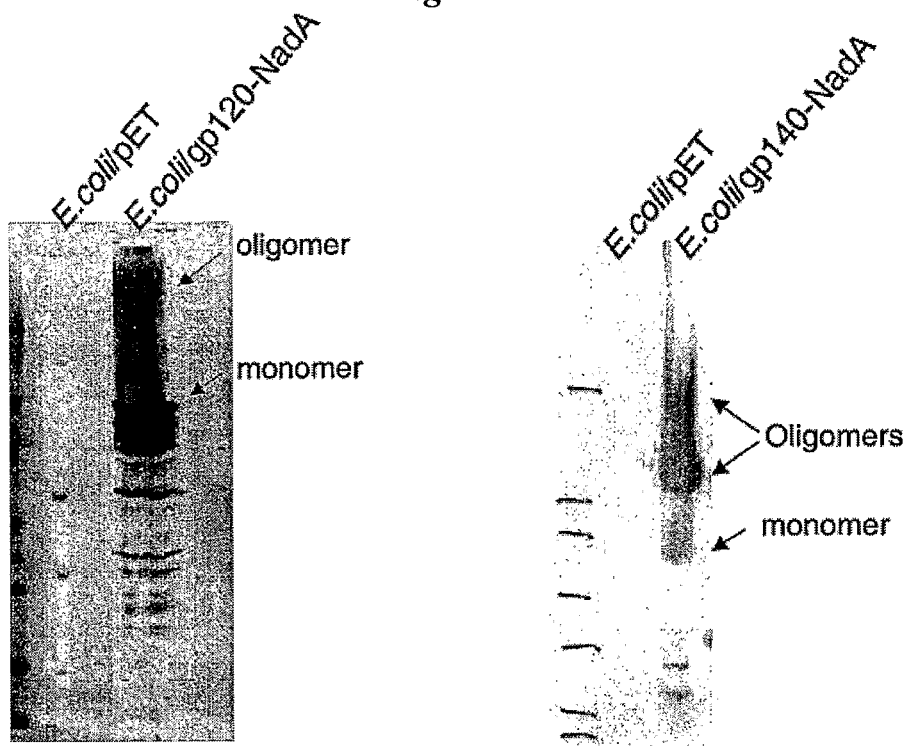
FIG. 7 shows western blots of *E. coli* expressing gp120-NadA and gp140-NadA.
Figure 8:
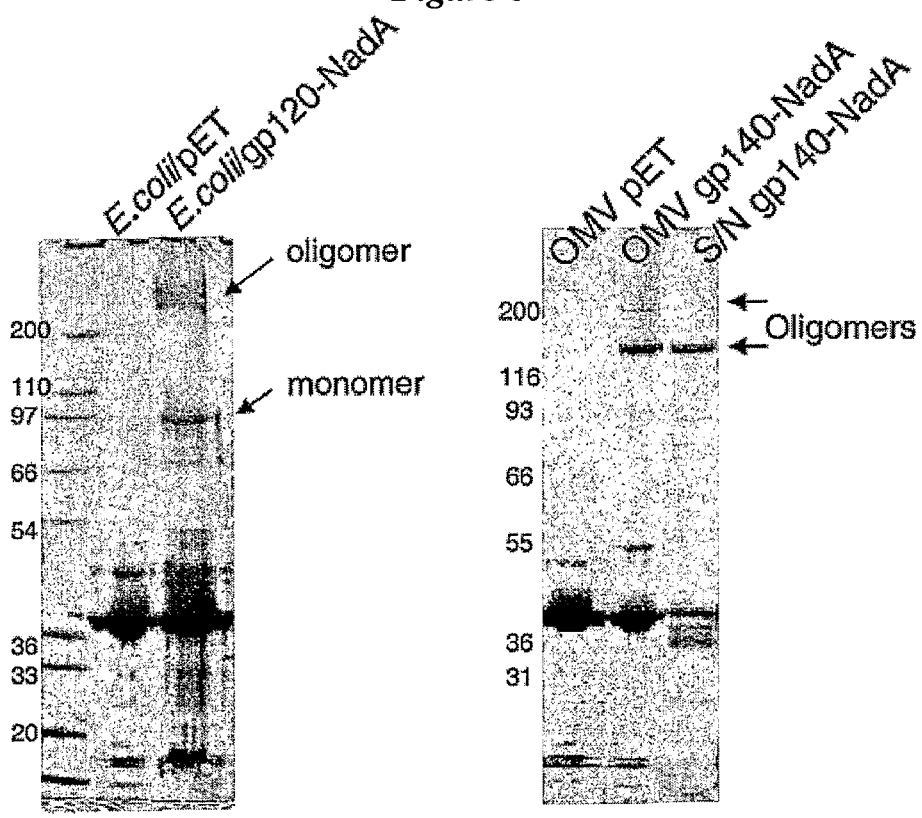
FIG. 8 shows SDS-PAGE of *E. coli* expressing gp120-NadA and gp140-NadA brane sequences for use with the invention are those from *Yersinia enterocolitica* adhesin YadA {69; e.g. SEQ ID N The spike glycoproteins of coronaviridae. Coronaviridae include coronaviruses and toroviruses. Viruses of interest include the human coronaviruses, Avian infectious bronchitis virus, Feline infectious peritonitis virus, Murine hepatitis virus, Porcine epidemic diarrhea virus, Porcine hemagglutinating encephalomyelitis virus, Porcine transmissible gastroenteritis virus, and Berne virus. The spike (E2) protein of human SARS coronavirus is a class I viral fusion protein {31} which is believed to form trimers, may be of interest.

The gp120-NadA and gp140-NadA polypeptides were expressed in *E. coli* BL21(DE3) using the pET system. Expression and localisation in *E. coli* were assayed by SDS-PAGE and western blot analysis on total cell lysate and on outer membrane vesicles. As shown in FIG. 7, a western blot of total cell lysate using anti-NadA antibody reveals expression of the protein in monomeric and oligomeric forms. Moreover, the proteins are also seen in SDS-PAGE of outer membrane vesicles, showing that the proteins are efficiently transported to the *E. coli* surface (FIG. 8). The gp140-NadA protein was also seen in the culture supernatant.

Figure 9:
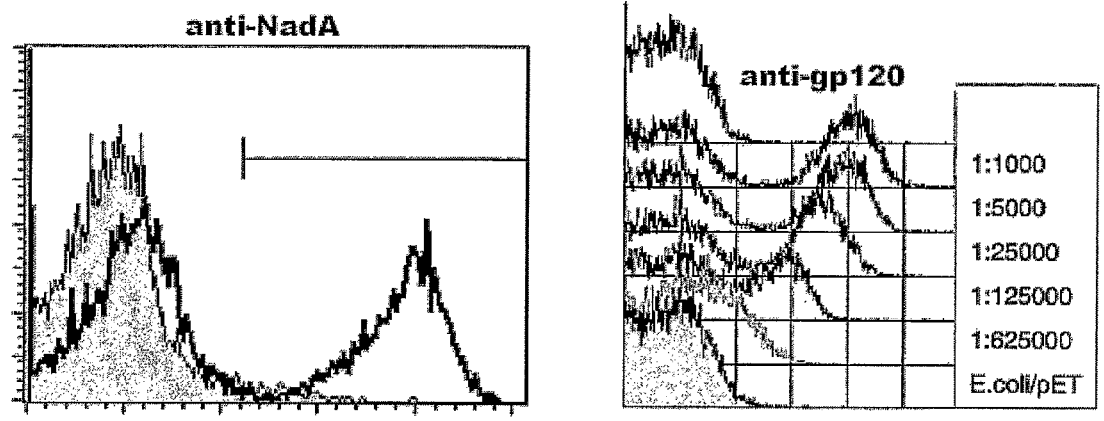
Figure 10:
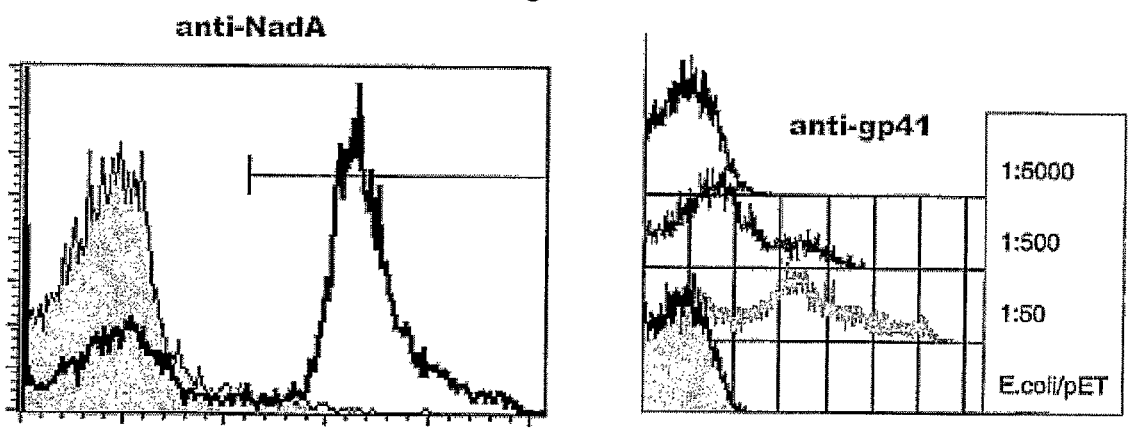
Figure 11:
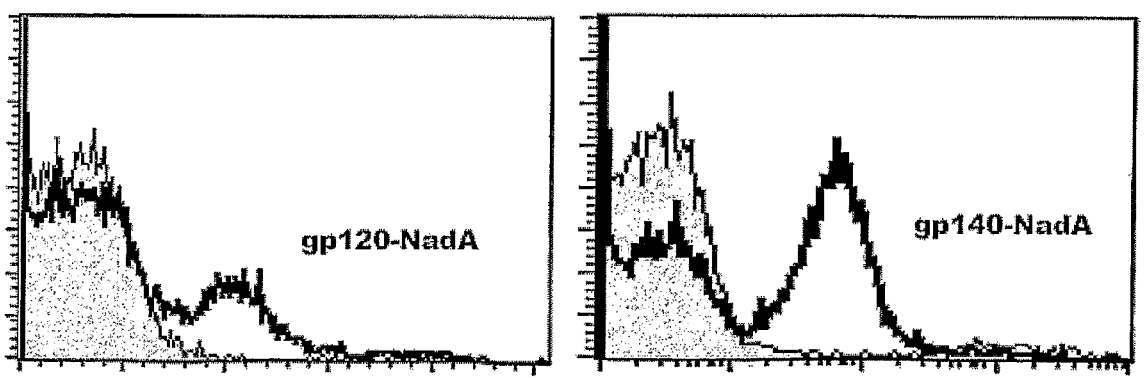
Figure 12:
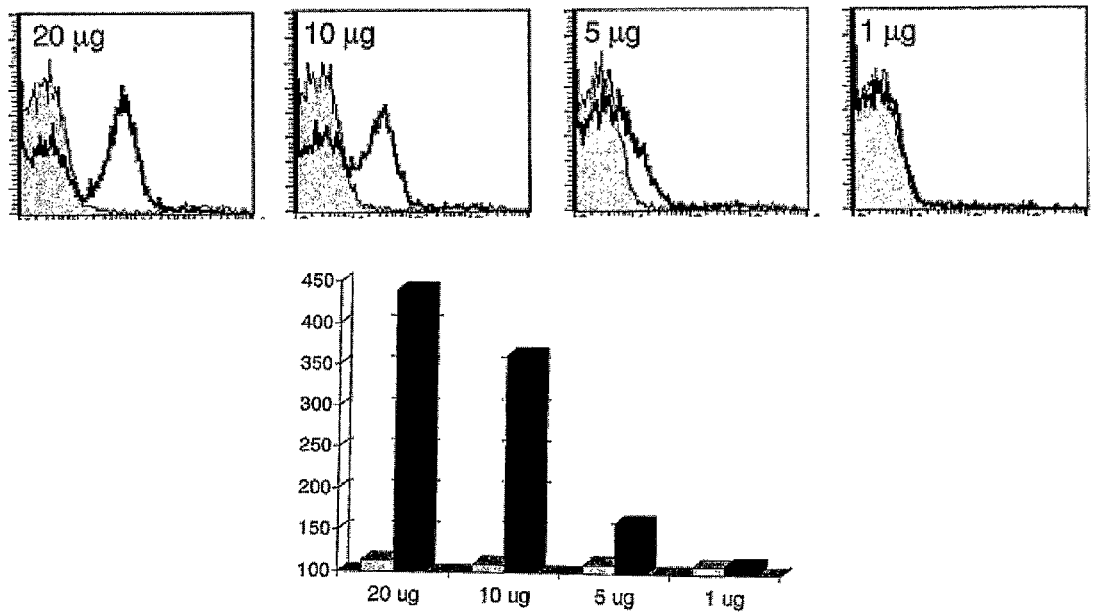
Figure 13:
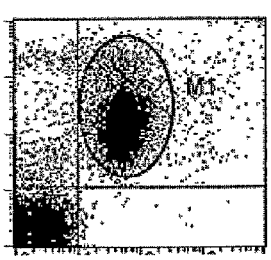
Figure 14:
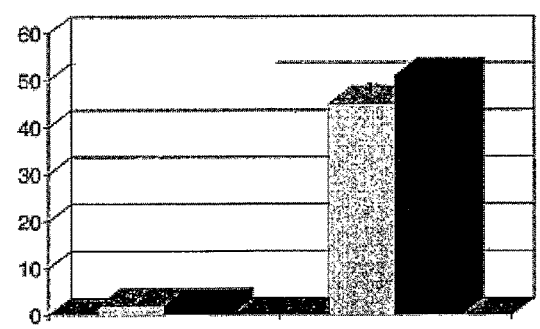
Figure 15:
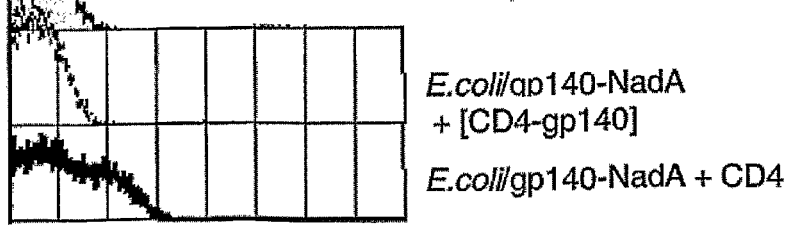
Figure 16:
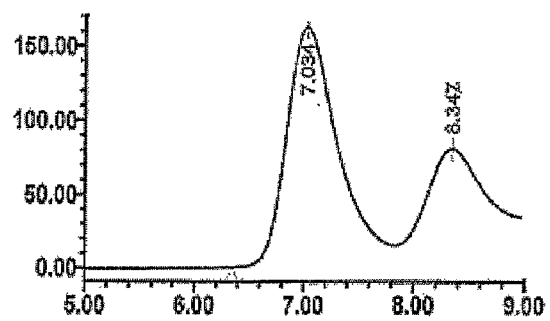
Figure 17:
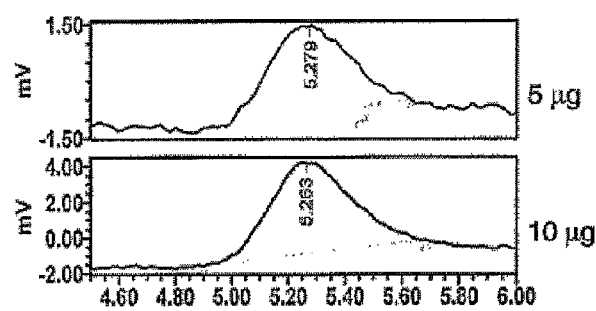
Figure 18:
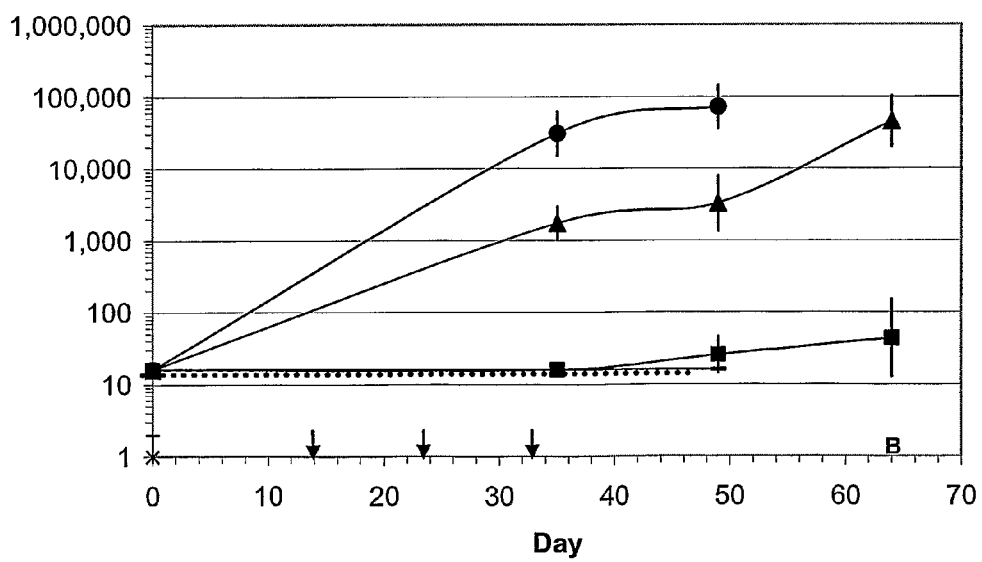

To confirm cell-surface exposure of the proteins, the *E. coli* were analysed by FACS on whole cell bacteria. Antibodies against NadA (polyclonal) and against the C4 conserved epitope of gp120 (monoclonal) were used for the gp120-NadA protein and, as shown in FIG. 9, surface expression was confirmed. Antibodies against NadA (polyclonal) and against a gp41 epitope (monoclonal 2F5) were used for the gp140-NadA protein, and surface expression was confirmed (FIG. 10).

To investigate folding, the CD4 affinity of the proteins was measured. The *E. coli* were incubated with soluble CD4 for 1 hour at 37° C., and binding was detected by FACS using a monoclonal anti-CD4 antibody. FIGS. 13 and 14 show the percentage of gp140-NadA *E. coli* that are able to bind to CD4. As shown in FIG. 11, *E. coli* expressing either of the proteins was able to bind to CD4. Dose-dependent binding was also seen, as shown in FIG. 12 for gp140-NadA. Moreover, pre-incubation of the CD4 with glycosylated gp140 inhibits the binding (FIG. 15).

Confirmation of the interaction between CD4 and gp140-NadA was obtained using a HPLC-based receptor binding assay with fluorescent-labelled CD4 (CD4-FITC). A positive control experiment (FIG. 16) showed that CD4-FITC alone has a retention time of 8.3 minutes, which is reduced to 7.0 minutes in the presence of purified glycosylated HIV gp120. As shown in FIG. 17, incubation of the CD4 with the culture supernatant of gp140-NadA (FIG. 8, right-hand column) resulted in the retention time of CD4 being reduced to 5.2 minutes, indicating formation of a complex between gp140-NadA and CD4.

To confirm that the Env domains maintain immunogenic properties, outer membrane preparations enriched with the recombinant Env-NadA proteins were used to immunize animals using a prime-boost strategy. Two or three rabbits per group were primed on days 0, 21, 35 and 49 with outer membrane vesicle preparations from *E. coli*/gp120-NadA, *E. coli*/gp140-NadA and *E. coli*/pET (negative control), using an aluminium hydroxide adjuvant. Glycosylated gp140 (purified from human cells) was used as positive control in combination with a MF59 adjuvant.

The group immunised with gp120-NadA was boosted at day 49 with complete glycosylated Env ectodomain (gp140ΔV2) to select antibodies that can bind to the native viral spike. Sera were analyzed at day 35 (post-two), 49 (post-three) and 64 (bleed out) by ELISA and neutralization assay.

Results showed that immunization with OMV gp120-NadA induced antibodies able to recognise the glycosylated gp140ΔV2 in ELISA (FIG. 18). These sera were tested for their ability to neutralize HIV-1 isolates. Titres at which the serum dilution reduced relative luminescence units by 50% compared to virus control wells were as follows:

| Antigen | | Sera post-three (day 49) | Sera bleed out (day 64) |
|---|---|---|---|
| | #7 | — | 1:34 |
| OMV/gp120-NadA | #8 | 1:80 | 1:950 |
| | #9 | — | 1:185 |
| Gp140deltaV2 | #17 | 1:2154 | nd |
| | #18 | 1:3590 | nd |

The sera against gp120-NadA OMV were able to neutralize homologous HIV-1 isolate SF162 at considerable dilution. In contrast, immunization with OMV gp140-NadA produced lower antibody titers, and these antibodies were not neutralizing antibodies against the homologous strain.

Thus the use of oligomerisation and transmembrane domains from NadA permits cell surface expression of the HIV envelope protein in *E. coli* in non-glycosylated CD4-binding oligomeric form.

It will be understood that the invention has been described by way of example only and modifications may be made whilst remaining within the scope and spirit of the invention.

REFERENCES (THE CONTENTS OF WHICH ARE HEREBY INCORPORATED BY REFERENCE)

{1} EP-A-0139417.
{2} US patent application 2003/0053984.
{3} Terskikh et al. (1997) *PNAS USA* 94:1663-1668.
{4} Comanducci et al. (2002) *J Exp Med* 195:1445-1454.
{5} Campbell & Downing (1994) *Trends Biotechnol* 12:168-172.
{6} Baron et al. (1991) *Trends Biochem Sci* 16:13-17.
{7} Burkhard et al. (2001) *Trends Cell Biol* 11:82-88.
{8} Section 5.5.2 of *Proteins* by Creighton (ISBN 0-7167-2317-4).
{9} Yu (2002) *Adv Drug Deliv Rev* 54:1113-1129.
{10} Muller et al. (2000) *Methods Enzymol* 328:261-282.
{11} Beck & Brodsky (1998) *J Struct Biol* 122:17-29.
{12} Lupas (1996) *Trends Biochem Sci* 21:375-382.
{13} Adamson et al. (1993) *Curr Opin Biotechnol* 4:428-347.
{14} Kammerer (1997) *Matrix Biol* 15:555-568.
{15} Chao et al. (1998) *J Chromatog B Biomed Sci Appl* 715:307-329.
{16} Arndt et al. (2002) *Structure* 10:1235-1248.
{17} Liu & Lu (2002) *J Biol Chem* 277:48708-48713.

{18} WO 03/010194
{19} U.S. Pat. No. 6,310,190.
{20} Section 5.5.3 of *Proteins* by Creighton (ISBN 0-7167-2317-4).
{21} Zhang & Chen (1999) *J Biol Chem* 274:22409-22413.
{22} Sanders et al. (2002) *J Virol* 76:8875-8889.
{23} Lamb et al. (1999) *Mol Membr Biol* 16:11-19.
{24} Zhu et al. (2002) *Biochem Biophys Res Commun* 299:897-902.
{25} Matthews et al. (2000) *J Virol* 74:5911-5920.
{26} Lawless et al. (2000) *Biochemistry* 39:11684-95.
{27} Zhao et al. (2000) *PNAS USA* 97:14172-7.
{28} Malashkevich et al. (1999) *PNAS USA* 96:2662-7.
{29} Weis et al. (1988) *Nature* 333:426-431.
{30} Yu et al. (1994) *Science* 266:274-6.
{31} Bosch et al. (2003) *J Virol* 77:8801-8811.
{32} Langevin et al. (2002) *J Biol Chem* 277:37655-37662.
{33} Gaudin et al. (1992) *Virology* 187:627-32.
{34} Desmezieres et al. (2003) *Virus Res* 91:181-7.
{35} Gibbons et al. (2000) *J Virol* 74:7772-7780.
{36} Heinz et al. (1994) *Arch Virol* 9:339-348.
{37} Wengler et al. (1987) *Virology* 160:210-219.
{38} Zhang et al. (2003) *EMBO J* 22:2604-13.
{39} Stiasny et al. (2002) *J Virol* 76:3784-90.
{40} Alfadhli et al. (2001) *J Virol* 75:2019-23
{41} Dutch et al. (2000) *Biosci Rep* 20:597-612.
{42} WO02/22167.
{43} WO02/34771.
{44} WO02/094868.
{45} United Kingdom patent application 0410866.8.
{46} WO00/78968.
{47} WO99/58562.
{48} WO99/58682.
{49} WO99/55871.
{50} WO99/57277.
{51} WO99/58684.
{52} WO99/64602.
{53} WO00/09694.
{54} WO99/63093.
{55} WO99/58685 & U.S. Pat. No. 6,706,494.
{56} WO99/64448.
{57} WO00/15802 & U.S. Pat. No. 6,600,013.
{58} WO00/52042.
{59} Suwa et al. (2002) *Genome Informatics* 13: 511-512.
{60} http://sevens.cbrc.jp/
{61} Hofmann & Stoffel (1993) *Biol. Chem. Hoppe-Seyler* 374:166.
{62} http://www.ch.embnet.org/software/tmbase/TMBASE_doc.html
{63} http://biophysics.biol.uoa.gr/DB-NTMR/
{64} Ikeda et al. (2003) *Nucleic Acids Res.* 31:406-409.
{65} http://bioinfo.si.hirosaki-u.ac.jp/~TMPDB/
{66} Bertaccini & Trudell (2002) *Protein Eng* 15:443-54.
{67} Ikeda et al. (2002) *In Silico Biol* 2:19-33.
{68} Shimaoka et al. (2000) *Nature Struct Biol* 7:674-678.
{69} Cornelis et al. (1998) *Microbiol Mol Biol Rev* 62:1315-1352.
{70} Chen et al. (1999) *Infect Immun* 67:1310-1316.
{71} International patent application PCT/IB2004/002351, filed 25 Jun. 2004, claiming priority from United Kingdom patent application 0315022.4.
{72} Beninati et al. (2000) *Nature Biotechnology* 18:1060-1064.
{73} WO99/27961.
{74} WO02/074244.
{75} WO02/064162.
{76} WO03/028760.
{77} Gennaro (2000) *Remington: The Science and Practice of Pharmacy.* 20$^{th}$ ed., ISBN: 0683306472.
{78} *Vaccine Design . . .* (1995) eds. Powell & Newman. ISBN: 030644867X. Plenum.
{79} WO00/23105.
{80} WO90/14837.
{81} U.S. Pat. No. 5,057,540.
{82} WO96/33739.
{83} EP-A-0109942.
{84} WO96/11711.
{85} WO00/07621.
{86} Barr et al. (1998) *Advanced Drug Delivery Reviews* 32:247-271.
{87} Sjolanderet et al. (1998) *Advanced Drug Delivery Reviews* 32:321-338.
{88} Niikura et al. (2002) *Virology* 293:273-280.
{89} Lenz et al. (2001) *J Immunol* 166:5346-5355.
{90} Pinto et al. (2003) *J Infect Dis* 188:327-338.
{91} Gerber et al. (2001) *Virol* 75:4752-4760.
{92} WO03/024480
{93} WO03/024481
{94} Gluck et al. (2002) *Vaccine* 20:B10-B16.
{95} EP-A-0689454.
{96} Johnson et al. (1999) *Bioorg Med Chem Lett* 9:2273-2278.
{97} Evans et al. (2003) *Expert Rev Vaccines* 2:219-229.
{98} Meraldi et al. (2003) *Vaccine* 21:2485-2491.
{99} Pajak et al. (2003) *Vaccine* 21:836-842.
{100} Kandimalla et al. (2003) *Nucleic Acids Research* 31:2393-2400.
{101} WO02/26757.
{102} WO99/62923.
{103} Krieg (2003) *Nature Medicine* 9:831-835.
{104} McCluskie et al. (2002) *FEMS Immunology and Medical Microbiology* 32:179-185.
{105} WO98/40100.
{106} U.S. Pat. No. 6,207,646.
{107} U.S. Pat. No. 6,239,116.
{108} U.S. Pat. No. 6,429,199.
{109} Kandimalla et al. (2003) *Biochemical Society Transactions* 31 (part 3):654-658.
{110} Blackwell et al. (2003) *J Immunol* 170:4061-4068.
{111} Krieg (2002) *Trends Immunol* 23:64-65.
{112} WO01/95935.
{113} Kandimalla et al. (2003) *BBRC* 306:948-953.
{114} Bhagat et al. (2003) *BBRC* 300:853-861.
{115} WO03/035836.
{116} WO95/17211.
{117} WO98/42375.
{118} Beignon et al. (2002) *Infect Immun* 70:3012-3019.
{119} Pizza et al. (2001) *Vaccine* 19:2534-2541.
{120} Pizza et al. (2000) *Int J Med Microbiol* 290:455-461.
{121} Scharton-Kersten et al. (2000) *Infect Immun* 68:5306-5313.
{122} Ryan et al. (1999) *Infect Immun* 67:6270-6280.
{123} Partidos et al. (1999) *Immunol Lett* 67:209-216.
{124} Peppoloni et al. (2003) *Expert Rev Vaccines* 2:285-293.
{125} Pine et al. (2002) *J Control Release* 85:263-270.
{126} Domenighini et al. (1995) *Mol Microbiol* 15:1165-1167.
{127} WO99/40936.
{128} WO99/44636.
{129} Singh et al} (2001) *J Cont Release* 70:267-276.
{130} WO99/27960.
{131} U.S. Pat. No. 6,090,406
{132} U.S. Pat. No. 5,916,588

{133} EP-A-0626169.
{134} WO99/52549.
{135} WO01/21207.
{136} WO01/21152.
{137} Andrianov et al. (1998) *Biomaterials* 19:109-115.
{138} Payne et al. (1998) *Adv Drug Delivery Review* 31:185-196.
{139} Stanley (2002) *Clin Exp Dermatol* 27:571-577.
{140} Jones (2003) *Curr Opin Investig Drugs* 4:214-218.
{141} WO99/11241.
{142} WO94/00153.
{143} WO98/57659.
{144} European patent applications 0835318, 0735898 and 0761231.
{145} Covacci & Rappuoli (2000) *J. Exp. Med.* 19:587-592.
{146} WO93/18150.
{147} Covacci et al. (1993) *Proc. Natl. Acad. Sci. USA* 90: 5791-5795.
{148} Tummuru et al. (1994) *Infect. Immun.* 61:1799-1809.
{149} Marchetti et al. (1998) *Vaccine* 16:33-37.
{150} Telford et al. (1994) *J. Exp. Med.* 179:1653-1658.
{151} Evans et al. (1995) *Gene* 153:123-127.
{152} WO96/01272 & WO96/01273, especially SEQ ID NO:6.
{153} WO97/25429.
{154} WO98/04702.
{155} WO99/24578.
{156} WO99/36544.
{157} WO99/57280.
{158} WO00/22430.
{159} Tettelin et al. (2000) *Science* 287:1809-1815.
{160} WO96/29412.
{161} Pizza et al. (2000) *Science* 287:1816-1820.
{162} WO01/52885.
{163} Bjune et al. (1991) *Lancet* 338(8775):1093-1096.
{164} Fukasawa et al. (1999) *Vaccine* 17:2951-2958.
{165} Rosenqvist et al. (1998) *Dev. Biol. Stand.* 92:323-333.
{166} Costantino et al. (1992) *Vaccine* 10:691-698.
{167} Costantino et al. (1999) *Vaccine* 17:1251-1263.
{168} Watson (2000) *Pediatr Infect Dis J* 19:331-332.
{169} Rubin (2000) *Pediatr Clin North Am* 47:269-285, v.
{170} Jedrzejas (2001) *Microbiol Mol Biol Rev* 65:187-207.
{171} Bell (2000) *Pediatr Infect Dis J* 19:1187-1188.
{172} Iwarson (1995) *APMIS* 103:321-326.
{173} Gerlich et al. (1990) *Vaccine* 8 Suppl:S63-68 & 79-80.
{174} Hsu et al. (1999) *Clin Liver Dis* 3:901-915.
{175} *Vaccines* (1988) eds. Plotkin & Mortimer. ISBN 0-7216-1946-0.
{176} Del Guidice et al. (1998) *Molecular Aspects of Medicine* 19:1-70.
{177} Gustafsson et al. (1996) *N. Engl. J. Med.* 334:349-355.
{178} Rappuoli et al. (1991) *TIBTECH* 9:232-238.
{179} WO02/02606.
{180} Kalman et al. (1999) *Nature Genetics* 21:385-389.
{181} Read et al. (2000) *Nucleic Acids Res* 28:1397-1406.
{182} Shirai et al. (2000) *J. Infect. Dis.* 181(Suppl 3):S524-S527.
{183} WO99/27105.
{184} WO00/27994.
{185} WO00/37494.
{186} WO99/28475.
{187} Ross et al. (2001) *Vaccine* 19:4135-4142.
{188} Sutter et al. (2000) *Pediatr Clin North Am* 47:287-308.
{189} Zimmerman & Spann (1999) *Am Fam Physician* 59:113-118, 125-126.
{190} Dreesen (1997) *Vaccine* 15 Suppl:S2-6.
{191} *MMWR Morb Mortal Wkly Rep* 1998 Jan. 16; 47(1):12, 19.
{192} Anderson (2000) *Vaccine* 19 Suppl 1:S59-65.
{193} Kahn (2000) *Curr Opin Pediatr* 12:257-262.
{194} Crowe (1995) *Vaccine* 13:415-421.
{195} McMichael (2000) *Vaccine* 19 Suppl 1:S101-107.
{196} Schuchat (1999) *Lancet* 353(9146):51-6.
{197} WO02/34771.
{198} Dale (1999) *Infect Dis Clin North Am* 13:227-43, viii.
{199} Ferrefti et al. (2001) *PNAS USA* 98: 4658-4663.
{200} Kuroda et al. (2001) *Lancet* 357(9264):1225-1240; see also page
{201} *J Toxicol Clin Toxicol* (2001) 39:85-100.
{202} Demicheli et al. (1998) *Vaccine* 16:880-884.
{203} Stepanov et al. (1996) *J Biotechno* 44:155-160.
{204} Ingram (2001) *Trends Neurosci* 24:305-307.
{205} Rosenberg (2001) *Nature* 411:380-384.
{206} Moingeon (2001) *Vaccine* 19:1305-1326.
{207} Ramsay et al. (2001) *Lancet* 357(9251):195-196.
{208} Lindberg (1999) *Vaccine* 17 Suppl 2:S28-36.
{209} Buttery & Moxon (2000) *J R Coll Physicians Lond* 34:163-168.
{210} Ahmad & Chapnick (1999) *Infect Dis Clin North Am* 13:113-133, vii.
{211} Goldblatt (1998) *J. Med. Microbiol.* 47:563-567.
{212} European patent 0 477 508.
{213} U.S. Pat. No. 5,306,492.
{214} International patent application WO98142721.
{215} *Conjugate Vaccines* (eds. Cruse et al.) ISBN 3805549326, particularly vol. 10:48-114.
{216} Hermanson (1996) *Bioconjugate Techniques* ISBN: 0123423368 or 012342335X.
{217} *Research Disclosure*, 453077 (January 2002)
{218} EP-A-0372501
{219} EP-A-0378881
{220} EP-A-0427347
{221} WO93/17712
{222} WO94/03208
{223} WO98/58668
{224} EP-A-0471177
{225} WO00/56360
{226} WO91/01146
{227} WO00/61761
{228} WO01/72337
{229} Robinson & Torres (1997) *Seminars in Immunology* 9:271-283.
{230} Donnelly et al. (1997) *Annu Rev Immunol* 15:617-648.
{231} Scott-Taylor & Dalgleish (2000) *Expert Opin Investig Drugs* 9:471-480.
{232} Apostolopoulos & Plebanski (2000) *Curr Opin Mol Ther* 2:441-447.
{233} Ilan (1999) *Curr Opin Mol Ther* 1:116-120.
{234} Dubensky et al. (2000) *Mol Med* 6:723-732.
{235} Robinson & Pertmer (2000) *Adv Virus Res* 55:1-74.
{236} Donnelly et al. (2000) *Am J Respir Crit Care Med* 162(4 Pt 2):S190-193.
{237} Davis (1999) *Mt. Sinai J. Med.* 66:84-90.
{238} *Current Protocols in Molecular Biology* (F. M. Ausubel et al., eds., 1987) Supplement 30.
{239} Smith & Waterman (1981) *Adv. Appl. Math.* 2: 482-489.
{240} International patent application PCT/US2004/011710.
{241} Srivastava et al. (2003) *J Virol* 77:11244-11259.

The invention claimed is:

1. A polypeptide comprising: (a) an antigenic domain; (b) an oligomerisation domain; and (c) a transmembrane domain, wherein domains (a), (b) and (c) are not all found together in the same polypeptide in nature and wherein at least one of (a), (b) and (c) has a eukaryotic or eukaryotic viral origin and at least one other of (a), (b) and (c) has a prokaryotic origin.

2. The polypeptide of claim 1, wherein the oligomerisation domain allows the polypeptide to form trimers.

3. The polypeptide of claim 1, wherein the oligomerisation domain is a coiled-coil domain.

4. The polypeptide of claim 3, wherein the coiled-coil domain is from a bacterial transmembrane protein.

5. The polypeptide of claim 4, wherein the transmembrane protein is an adhesin.

6. The polypeptide of claim 5, wherein the adhesin is *Yersinia enterocolitica* adhesin YadA, *Neisseria meningitidis* adhesin NadA or *Moraxella catarrhalis* surface protein UspA2.

7. The polypeptide of claim 1, wherein the antigenic domain is a surface antigen from a bacterium or virus.

8. The polypeptide of claim 7, wherein the antigenic domain comprises the extraviral domain of a viral fusion protein.

9. The polypeptide of claim 8, wherein the fusion protein is selected from the group consisting of: the Env protein of a retrovirus; the F protein of a paramyxovirus; the Gp protein of Ebola virus; the hemagglutinin protein of influenza virus; the spike proteins of a coronavirus; the Rabies virus glycoprotein (RVG); the fusion protein of an arbovirus; the fusion proteins of a togaviridae; the fusion protein of a flaviviridae; the fusion protein of an alphavirus; the E protein of dengue virus; the E protein of hepatitis C virus; the E protein of yellow fever virus; the E protein of japanese encephalitis virus; the E protein of west nile virus; the E protein of tick-borne encephalitis (TBE) virus; the fusion protein of measles virus; the E1 spike protein of Semliki Forest virus; the fusion protein of a bunyaviridae; and the fusion protein of an arenavndae.

10. The polypeptide of claim 9, wherein the Env protein of a retrovirus is the HIV envelope protein.

11. The polypeptide of claim 9, wherein the antigenic domain is from the N-terminus cleavage product of the fusion polypeptide.

12. The polypeptide of claim 7, wherein the antigenic domain is from a surface protein from a bacterium selected from the group consisting of: *Neisseria meningitidis; Neisseria gonorrhoeae; Streptococcus pneumoniae; Streptococcus pyogenes; Streptococcus agalactiae; Staphylococcus aureus; Haemophilus influenzae; Moraxella catarrhalis; Helicobacter pylori; Chlamydia trachomatis*; and *Chlamydia pneumoniae.*

13. The polypeptide of claim 1, wherein the transmembrane domain is from a bacterial transmembrane protein.

14. The polypeptide of claim 1, wherein domains (b) and (c) are from the same protein.

15. The polypeptide of claim 14, wherein domain (c) is from a prokaryote and domain (a) is from a eukaryotic virus.

16. A polypeptide comprising: (a) an antigenic domain from the viral fusion protein of an enveloped eukaryotic virus; (b) a coiled-coil domain from a bacterial adhesin; and (c) a transmembrane domain from the same bacterial adhesin as (b).

17. A polypeptide of formula NH2-A-B-C-D-E-F-G-H-COOH where:

A is an optional leader sequence; B is an optional linker sequence; C is an antigenic sequence; D is an optional linker sequence; E is a coiled-coil sequence; F is an optional linker sequence; G is a transmembrane sequence; and H is an optional I cytoplasmic tail, wherein the antigenic sequence is from a surface protein from a bacterium selected from the group consisting of: *Neisseria meningitidis; Neisseria gonorrhoeae; Streptococcus pneumoniae; Streptococcus pyogenes; Streptococcus agalactiae; Staphylococcus aureus; Haemophilus influenzae; Moraxella catarrhalis; Helicobacter pylori; Chlamydia trachomatis*; and *Chlamydia pneumoniae.*

18. An oligomeric protein, comprising oligomerised polypeptides of any one of claims 2 to 14 and 15 to 17.

19. The oligomeric protein of claim 18, which is a trimer.

20. A pharmaceutical composition comprising the polypeptide of any one of claims 1 to 14 and 15 to 17.

21. A pharmaceutical composition comprising the protein of claim 18.

22. A pharmaceutical composition comprising the protein of claim 19.

23. A method for raising an immune response in a mammal comprising the step of administering an effective amount of the composition of claim 20 to the mammal thereby raising an immune response in the mammal.

* * * * *